(12) United States Patent
Henry

(10) Patent No.: US 7,643,949 B2
(45) Date of Patent: *Jan. 5, 2010

(54) CORIOLIS MODE PROCESSING TECHNIQUES

(75) Inventor: Manus P. Henry, Oxford (GB)

(73) Assignee: Invensys Systems, Inc., Foxboro, MA (US)

( * ) Notice: Subject to any disclaimer, the term of this patent is extended or adjusted under 35 U.S.C. 154(b) by 0 days.

This patent is subject to a terminal disclaimer.

(21) Appl. No.: 12/036,797

(22) Filed: Feb. 25, 2008

(65) Prior Publication Data

US 2008/0262756 A1 Oct. 23, 2008

Related U.S. Application Data

(63) Continuation of application No. 11/456,473, filed on Jul. 10, 2006, now Pat. No. 7,343,253.

(60) Provisional application No. 60/697,574, filed on Jul. 11, 2005.

(51) Int. Cl.
*G01F 23/00* (2006.01)

(52) U.S. Cl. ..................... 702/54

(58) Field of Classification Search .............. 702/54
See application file for complete search history.

(56) References Cited

U.S. PATENT DOCUMENTS

| 4,760,739 | A |   | 8/1988  | Ichino |
| 5,027,662 | A |   | 7/1991  | Titlow et al. |
| 5,549,000 | A | * | 8/1996  | Brown et al. ............ 73/587 |
| 5,827,979 | A |   | 10/1998 | Schott |
| 5,975,747 | A |   | 11/1999 | Flaherty |
| 5,996,650 | A |   | 12/1999 | Phallen |
| 6,092,429 | A |   | 7/2000  | Cunningham |
| 6,173,214 | B1 |  | 1/2001  | Neelay |
| 6,507,791 | B2 |  | 1/2003  | Henry |
| 6,758,102 | B2 |  | 7/2004  | Henry |
| 6,769,301 | B2 |  | 8/2004  | Barger |
| 7,313,488 | B2 |  | 12/2007 | Henry |
| 2002/0183951 | A1 | * | 12/2002 | Cunningham et al. ....... 702/106 |
| 2003/0154804 | A1 |   | 8/2003  | Henry |
| 2003/0191598 | A1 |   | 10/2003 | Normen |
| 2004/0031328 | A1 |   | 2/2004  | Henry |
| 2008/0092667 | A1 | * | 4/2008  | Shelly et al. ........... 73/861.355 |

OTHER PUBLICATIONS

English language translation of the Text of the First Office Action from Chinese Patent Application No. 200480038060.7 mailed Dec. 28, 2007 (5 pages).
M. Henry et al., The Dynamic Response of Coriolis Mass Flow Meters: Theory and Applications, The Instrumentation, Systems and Automation Society, 2004, 12 pages.
International Search Report and Written Opinion for International Application No. PCT/US06/27011, mailed Jul. 3, 2008, 12 pages.

(Continued)

*Primary Examiner*—Bryan Bui
*Assistant Examiner*—Jonathan Teixeira Moffat
(74) *Attorney, Agent, or Firm*—Fish & Richardson P.C.

(57) ABSTRACT

Flowmeters are described in which a sensor signal received from a sensor that is attached to vibratable flowtube, so as to determine properties of a fluid within the flowtube, contains a drive signal component and a coriolis mode component. The flowmeters are operable to determine drive parameters of the drive signal component, as well as coriolis parameters of the coriolis mode component. By analyzing the sensor signal based on the drive signal parameters, and not on the coriolis signal parameters, the flowmeters are able to provide stable and accurate determinations of the properties of the fluid.

36 Claims, 22 Drawing Sheets

OTHER PUBLICATIONS

Office Action dated Feb. 27, 2007 in U.S. Appl. No. 11/456,461.
Notice of Allowance dated Aug. 13, 2007 in U.S. Appl. No. 11/456,461.
Behhadj, A., et al "The Simulation of Coriolis Meter Response to Pulsating Flow Using a General Purpose F.E. Code," *Journal of Fluids and Structures* (2000), vol. 14, pp. 613-634.
Cheesewright, Robert, et al. "Effect of Mechanical Vibrations on Coriolis Mass Flow Meters," *Journal of Dynamic Systems, Measurement and Control* (Mar. 2003), vol. 125, pp. 103-113.
Cheesewright, R., et al. "The Dynamic Response of Coriolis Massflow Meters," *Proceedings of FLUCOME '2000*, Sherbrook, Canada, Aug. 2000, 6 pgs.
Cheesewright, R., et al. "The Effect of Flow Pulsations on Coriolis Mass Flow Meters," *Journal of Fluids and Structures* (1998), vol. 12, pp, 1025-1039.
Cheesewright, it., et al. "Understanding the Experimental Response of Coriolis Massflow Meters to Flow Pulsations," *Flow Measurement and Instrumentation* (1999), vol. 10, pp. 207-215.
Clark, C,, et al. "The Influence Upon Coriolis Mass Flow Meters of External Vibrations at Selected Frequencies," *Flow Measurement and Instrumentation* (2003), vol. 14, pp. 33-42.
Clough, Ray, et al. *Dynamics of Structures* (1975), New York: McGraw Hill.
Cunningham, T.J., et al. "Zero Shifts in Coriolis Sensors Due to Imbalance," *AIAA Technical Paper*, AIAA-94-1621-CP, pp. 2409-2418.
Hulbert, G.M., et al, "Numerical and Experimental Analysis of Coriolis Mass Flowmeters," *AIAA Technical Paper*, AIAA-95/1384-CP, pp. 1889-1893.
Paldoussis, M.P., et al. "Dynamic Stability of Pipes Conveying Fluid," *Journal of Sound and Vibration* (1974), vol. 33, No. 3, pp. 267-294.
Raszillier, H, et al. "Coriolis-Effect in Mass Flow Metering," *Archive of Applied Mechanics* (1991), vol. 61, pp. 192-214.
Raszillier, H., et al. "Mode Mixing in Coriolis Flowmeters," Archive of Applied Mechanics (1993), vol. 63, pp. 219-227.
Stack, C.F., et al., "A Finite Element for the Vibration Analysis of a Fluid-Conveying Timoshenko Beam," *AIAA Technical Paper, 34th AIAA/ASME Adaptive Structures Forum*, Apr. 19-22, 1993, La Jolla, California, AIAA-93-1552-CP, pp. 2120-2129.
Wiklund, David et al. "Quantifying and Specifying the Dynamic Response of Flowmeters," *ISA 2002 Technology Update, Proceedings of ISA2002 Technical Conference*, Oct. 21-23, 2002, Chicago, Illinois, vol. 422, pp. 463-475.
Office Action for U.S. Appl. No. 11/953,773, mailed Mar. 20, 2009.

* cited by examiner

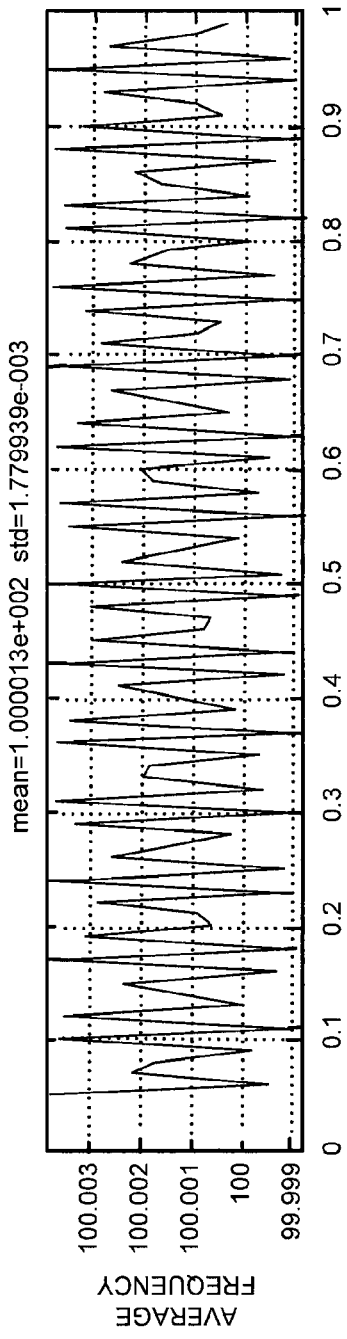
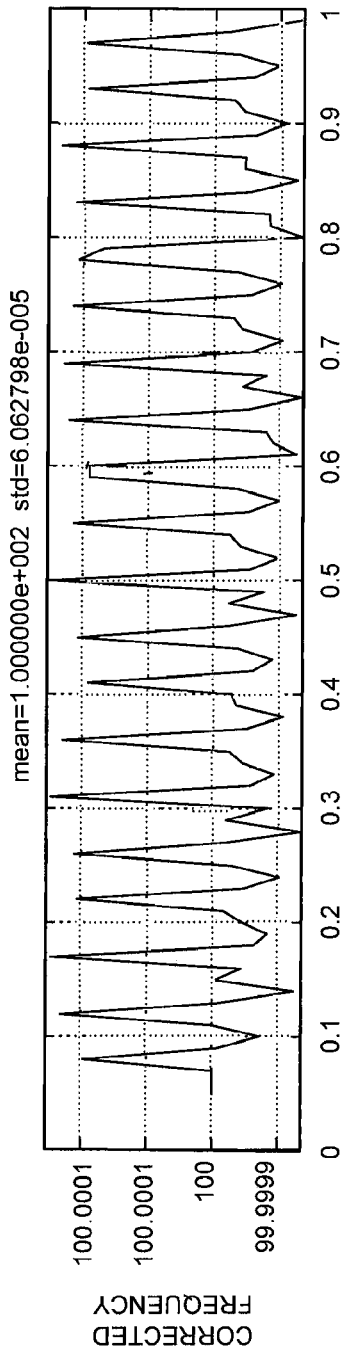
FIG. 17A
FIG. 17B

CORIOLIS MODE PROCESSING TECHNIQUES

CROSS-REFERENCE TO RELATED APPLICATIONS

This application is a continuation of U.S. application Ser. No. 11/456,473, filed Jul. 10, 2006, titled CORIOLIS MODE PROCESSING TECHNIQUES, which claims priority to U.S. Provisional Application No. 60/697,574, filed on Jul. 11, 2005, titled CORIOLIS MODE PROCESSING FOR FLOWMETERS, both of which are hereby incorporated by reference in their entirety.

TECHNICAL FIELD

This description relates to flowmeters.

BACKGROUND

Flowmeters provide information about materials being transferred through a conduit. For example, mass flowmeters provide a measurement of the mass of material being transferred through a conduit. Similarly, density flowmeters, or densitometers, provide a measurement of the density of material flowing through a conduit. Mass flowmeters also may provide a measurement of the density of the material.

For example, Coriolis-type mass flowmeters are based on the Coriolis effect, in which material flowing through a conduit becomes a mass that is affected by a Coriolis force and therefore experiences an acceleration. Many Coriolis-type mass flowmeters induce a Coriolis force by sinusoidally oscillating a conduit about a pivot axis orthogonal to the length of the conduit. In such mass flowmeters, the Coriolis reaction force experienced by the traveling fluid mass is transferred to the conduit itself and is manifested as a deflection or offset of the conduit in the direction of the Coriolis force vector in the plane of rotation.

SUMMARY

According to one general aspect, a method includes receiving a sensor signal from a sensor that is operable to detect a vibration of a flowtube having a fluid flowing therethrough, the sensor signal including a major signal component having a major amplitude and a minor signal component having a minor amplitude, the major amplitude being larger than the minor amplitude. The method also includes performing a signal analysis of the sensor signal over a time period that is defined with respect to a period of oscillation of the minor signal component, and identifying a value of the major amplitude, based on the signal analysis.

Implementations may include one or more of the following features. For example, the major signal component may be related to a drive mode signal applied to the flowtube to maintain oscillation thereof, and the minor signal component may be related to a coriolis mode signal that is present in the sensor signal. The method may further include identifying a timing offset between a first zero-crossing of the drive mode signal and a corresponding, second zero-crossing of the sensor signal, the offset caused at least in part by a presence of the coriolis mode signal within the sensor signal. Performing the signal analysis may include determining a first estimate of a major frequency of the major signal component, and determining a second estimate of a minor frequency of the minor signal component. The method may further include revising the first estimate and the second estimate, based on consecutive offsets of consecutive cycles of the sensor signal.

In other implementations, the method may further include identifying the minor amplitude based on the signal analysis, and identifying a phase of the coriolis mode signal, based on the major amplitude and the timing offset. The method may also include determining revised values for the major amplitude and the timing offset, based on the minor amplitude and the phase of the coriolis mode signal.

Performing the signal analysis may include performing a first calculation to obtain a drive-emphasized characterization of the sensor signal, in which parameters of the drive mode signal are maximized relative to parameters of the coriolis mode signal, and performing a second calculation to obtain a coriolis-emphasized characterization of the sensor signal, in which parameters of the coriolis mode signal are maximized relative to parameters of the drive mode signal. Performing the first calculation may be based on a value that is twice a frequency of the coriolis mode signal, and performing the second calculation may be based on a value that is equal to the frequency of the coriolis mode signal. The first calculation and the second calculation may include a first integration and a second integration, respectively, that are defined with respect to the frequency of the coriolis mode signal.

Performing the signal analysis may include performing the signal analysis based on an offset between an actual period of the major signal component and an observed period of the sensor signal. Performing the signal analysis may further include selecting the offset such that the signal analysis is performed with respect to a sampling of the sensor signal by an analog-to-digital converter, and such that limits of the time period coincide with samples of the sampling. In another implementation, performing the signal analysis may include removing harmonics of the drive mode signal that are present within the sensor signal.

According to another general aspect, a system includes a signal analyzer that is operable to receive a sensor signal from a sensor that detects a vibration of a flowtube having a fluid flowing therethrough, the sensor signal including a major signal component having a major amplitude and a minor signal component having a minor amplitude, the major amplitude being larger than the minor amplitude. A mode maximizer is operable to perform a first analysis of the sensor signal to obtain a first characterization of the sensor signal in which the major signal component is emphasized relative to the minor signal component, and operable to perform a second analysis of the sensor signal to obtain a second characterization of the sensor signal in which the minor signal component is emphasized relative to the major signal component. A signal identifier is operable to receive the first characterization from the mode maximizer and obtain the major amplitude therefrom, based on the first characterization.

Implementations may include one or more of the following features. For example, the signal identifier may be further operable to receive the second characterization of the sensor signal from the mode maximizer and obtain the minor amplitude therefrom, based on the second characterization, major amplitude, and a timing offset between a zero-crossing of the major signal component and a corresponding zero-crossing of the sensor signal. The signal identifier may be further operable to receive the second characterization of the sensor signal from the mode maximizer and obtain the minor amplitude and a phase of the minor signal component therefrom, based on the second characterization, the major amplitude, and the timing offset. The signal identifier may be operable to determine a revised value of the major amplitude and the timing offset, based on the minor amplitude and the phase of the minor signal. In another example, the signal analyzer may be operable to perform the first analysis and the second analysis with respect to a time window that is defined in relation to a period of oscillation of the minor signal component.

The major signal component may be related to a drive mode signal applied to the flowtube to maintain oscillation thereof, and the minor signal component may be related to a coriolis mode signal that is present in the sensor signal.

The signal identifier may be operable to identify a timing offset between a first zero-crossing of the drive mode signal and a corresponding, second zero-crossing of the sensor signal, the offset caused at least in part by a presence of the coriolis mode signal within the sensor signal.

The signal analyzer may be operable to determine a first frequency associated with the major signal component and a second frequency associated with the minor signal component, for use in the first calculation and the second calculation, respectively.

The signal analyzer may be operable to perform the first analysis based on a value that is twice a frequency of the minor signal component, and is operable to perform the second analysis based on a value that is equal to the frequency of the minor signal component.

According to another general aspect, an apparatus includes a storage medium having instructions stored thereon, the instructions including a first code segment for receiving a sensor signal from a sensor that is attached to a vibratable flowtube, a second code segment for determining a drive parameter related to a drive signal component of the sensor signal, based on a first analysis of the sensor signal that is defined with respect to a period of oscillation of a coriolis signal component of the sensor signal, and a third code segment for determining a coriolis parameter related to the coriolis signal component, based on a second analysis of the sensor signal and on the drive parameter.

Implementations may include one or more of the following features. For example, the apparatus may include a fourth code segment for determining a revised estimate of the drive parameter, based on the coriolis parameter.

The first analysis may provide a first characterization of the sensor signal in which parameters of the drive signal component are emphasized relative to the coriolis signal component, and the second analysis may provide a second characterization of the sensor signal in which parameters of the coriolis signal component are emphasized relative to the drive signal component.

The details of one or more implementations are set forth in the accompanying drawings and the description below. Other features will be apparent from the description and drawings, and from the claims.

DESCRIPTION OF DRAWINGS

FIGS. 17A and 17B are graphs illustrating an average frequency and a corrected frequency.

DETAILED DESCRIPTION

Types of flowmeters include digital flowmeters. For example, U.S. Pat. No. 6,311,136, which is hereby incorporated by reference, discloses the use of a digital flowmeter and related technology including signal processing and measurement techniques. Such digital flowmeters may be very precise in their measurements, with little or negligible noise, and may be capable of enabling a wide range of positive and negative gains at the driver circuitry for driving the conduit. Such digital flowmeters are thus advantageous in a variety of settings. For example, commonly-assigned U.S. Pat. No. 6,505,519, which is incorporated by reference, discloses the use of a wide gain range, and/or the use of negative gain, to prevent stalling and to more accurately exercise control of the flowtube, even during difficult conditions such as two-phase flow.

Analog flowmeters also exist. Although such analog flowmeters may be prone to typical shortcomings of analog circuitry, e.g., low precision and high noise measurements relative to digital flowmeters, they also may be compatible with the various techniques and implementations discussed herein. Thus, in the following discussion, the term "flowmeter" or "meter" is used to refer to any type of device and/or system in which a flowmeter system, such as, for example, a Coriolis flowmeter system uses various control systems and related elements to measure a mass flow, density, and/or other parameters of a material(s) moving through a flowtube or other conduit.

Figure 1A:
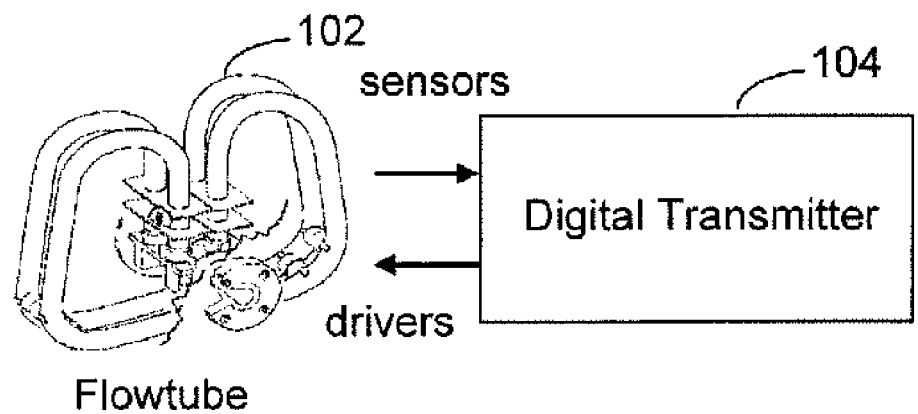
FIG. 1A is an illustration of a flowmeter using a bent flowtube.

FIG. 1A is an illustration of a flowmeter using a bent flowtube 102. Specifically, the bent flowtube 102 may be used to measure one or more physical characteristics of, for example, a (traveling) fluid, such as, for example, density, as referred to above. In FIG. 1A, a digital transmitter 104 exchanges sensor and drive signals with the bent flowtube 102, so as to both sense an oscillation of the bent flowtube 102, and to drive the oscillation of the bent flowtube 102 accordingly. By quickly and accurately determining the sensor and drive signals, the digital transmitter 104, as referred to above, provides for fast and accurate operation of the bent flowtube 102. Examples of the transmitter 104 being used with a bent flowtube are provided in, for example, commonly-assigned U.S. Pat. No. 6,311,136.

Figure 1B:
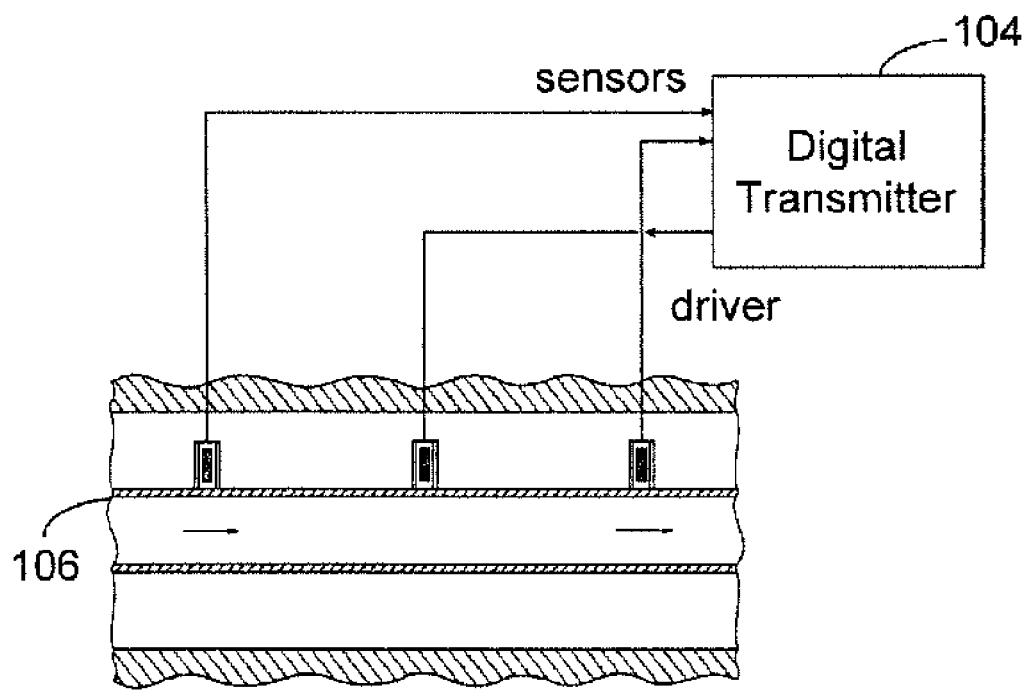
FIG. 1B is an illustration of a flowmeter using a straight flowtube.

FIG. 1B is an illustration of a flowmeter using a straight flowtube 106. More specifically, in FIG. 1B, the straight flowtube 106 interacts with the digital transmitter 104. Such a straight flowtube operates similarly to the bent flowtube 102 on a conceptual level, and has various advantages/disadvantages relative to the bent flowtube 102. For example, the straight flowtube 106 may be easier to (completely) fill and empty than the bent flowtube 102, simply due to the geometry of its construction. In operation, the bent flowtube 102 may operate at a frequency of, for example, 50-110 Hz, while the straight flowtube 106 may operate at a frequency of, for example, 300-1,000 Hz.

Figure 2:
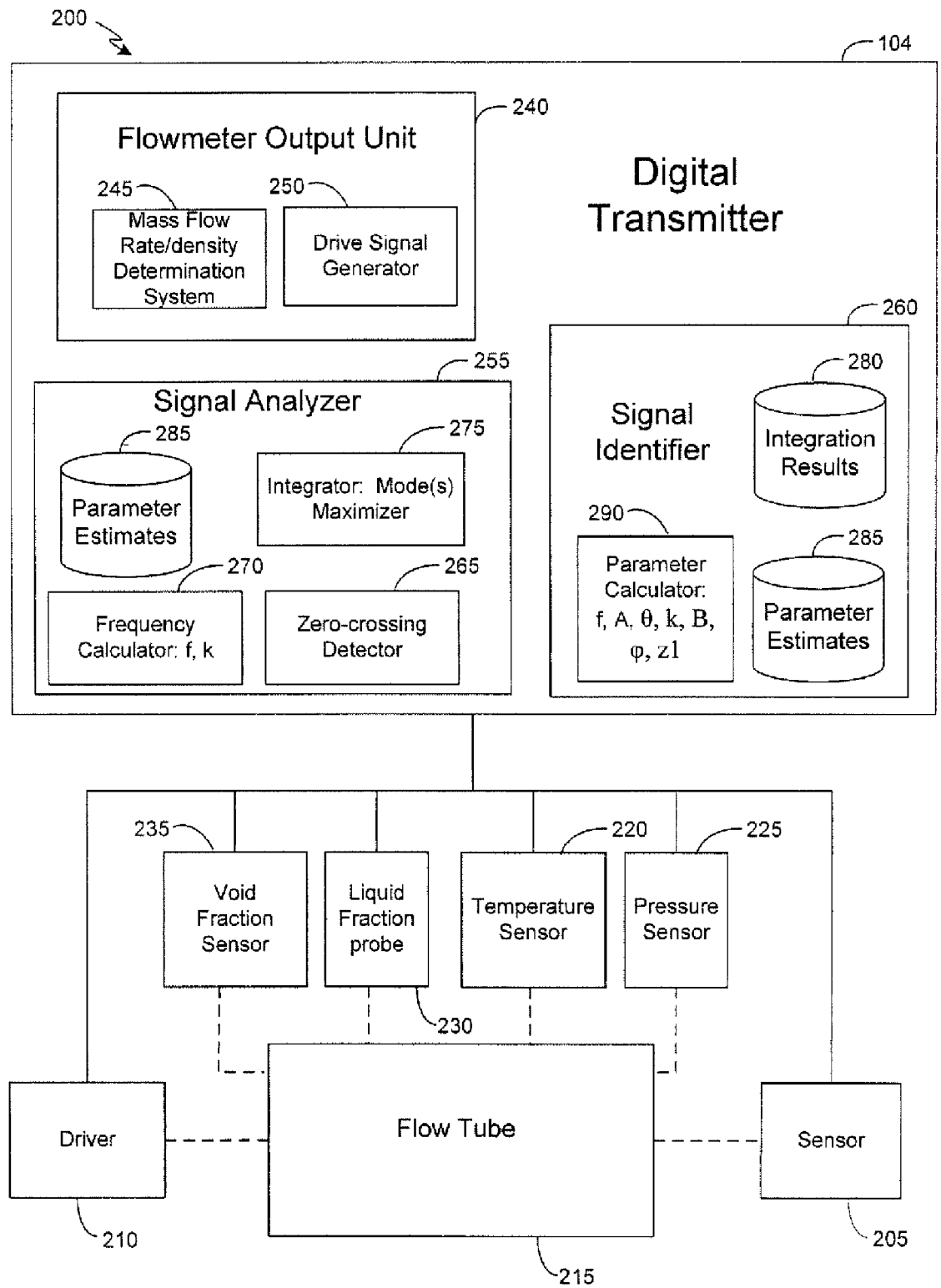
FIG. 2 is a block diagram of a flowmeter using Coriolis mode processing techniques.

FIG. 2 is a block diagram of a flowmeter using Coriolis mode processing techniques. In FIG. 2, a digital mass flowmeter 200 includes the digital transmitter 104, one or more motion sensors 205, one or more drivers 210, a flowtube 215 (which also may be referred to as a conduit, and which may represent either the bent flowtube 102, the straight flowtube 106, or some other type of flowtube), and a pressure sensor 220. The digital transmitter 104 may be implemented using one or more of, for example, a processor, a Digital Signal Processor (DSP), a field-programmable gate array (FPGA), an ASIC, other programmable logic or gate arrays, or programmable logic with a processor core.

The digital transmitter 104 generates a measurement of, for example, density and/or mass flow of a material flowing through the flowtube 215, based at least on signals received from the motion sensors 205. The digital transmitter 104 also controls the drivers 210 to induce motion in the flowtube 215. This motion is sensed by the motion sensors 205.

Density measurements of the material flowing through the flowtube are related to, for example, the frequency of the motion of the flowtube 215 that is induced in the flowtube 215 by a driving force supplied by the drivers 210, and/or to the temperature of the flowtube 215. Similarly, mass flow through the flowtube 215 is related to the phase and frequency of the motion of the flowtube 215, as well as to the temperature of the flowtube 215. The flowmeter 200 may be configures to measure only density, and thereby to operate as a densitometer.

The temperature in the flowtube 215, which is measured using the temperature sensor 220, affects certain properties of the flowtube, such as its stiffness and dimensions. Also in FIG. 2, a pressure sensor 225 is illustrated that is in communication with the transmitter 104, and is connected to the flowtube 215 so as to be operable to sense a pressure of a material flowing through the flowtube 215. More particularly, pressure measurements may relate to an absolute pressure measurement of the fluid within the flowtube 215, or to a differential pressure drop across a portion of the flowtube.

FIG. 2 also illustrates a liquid fraction probe 230 that is operable to measure an amount of a particular liquid within the flow tube 215 when the flow tube 215 contains a mixed fluid having more than one fluid component, such as, for example, oil and water. Somewhat similarly, a void fraction sensor 235 measures a percentage of gas within a fluid inner flow tube 215 that contains at least one liquid and at least one gas component. Although not specifically illustrated in FIG. 2, various other components may be used to measure or determine properties of the fluid within the flow tube 215.

The digital transmitter 104 includes a flow meter output unit 240 that is operable to determine information related to an operation of the flow meter 200. In particular, the flow meter output unit 240 includes a mass flow rate/density determination system 245 that is operable to determine either a mass flow rate and/or a density of a fluid within the flow tube 215. The flow meter output unit 240 also includes a drive signal generator 250 that is operable to output drive signal characteristics to the drivers 210, so as to maintain oscillation of the flow tube 215.

The flow meter output unit 240 performs the above-described functions based on the sensor signals received from the sensors 205. For example, the flow meter output unit 240 may analyze sensor signals from the sensors 205 to determine a frequency of the sensor signals, and/or phase differences between the sensor signals from different ones of sensors 205.

In theory, these sensor signals reflect the form, parameters, and characteristics of the vibration of the flowtube at the drive frequency applied by the drivers 210, and contain, either within themselves or in relation to one another, information regarding the mass flow rate, density, or other parameters of the fluid flow within the flowtube 215. For example, if the drive signal is simplified and applied as a pure sinusoidal signal, then the sensor signal detected by the sensors 205 also should be, in theory, essentially a pure sinusoid. In practice, a number of contaminants are present within the sensor signals that may alter the characteristics of the sensor signals in an undesirable way. Thus, measurements output by the flow meter output unit 240 may be less accurate as a result of the presence of these contaminants within the sensor signal.

One example of a contaminant within the sensor signal includes harmonics of the drive frequency that may be within the sensor signals. Such harmonics may be caused by, for example, non-linearities within the sensors 205, and do not represent actual vibrations within the flow tube 215. If the drive frequency is designated as the first harmonic, then typical second, third and fourth harmonic amplitudes may be at, for example, 1%, 0.5%, 0.5% and 0.1%, respectively, of the amplitude of the first harmonic. Furthermore, ten or more higher harmonics may be observed within the sensor signal in a given circumstance.

Another source of contaminant of the sensor signal includes other modes of vibration of the flow tube 215 besides the desired driven mode that results from application of the drive signals. For example, external vibrations, sudden changes in flow rate, or various other factors may result in the presence of additional modes of vibration of the flow tubes 215.

One example of the modes of vibration that may be present within the flow meter 200 is known as the coriolis mode of vibration. The coriolis mode is typically the mode nearest to the driven mode, and is referred to as the coriolis mode because the coriolis force associated with mass flow measurements of the flow meter 200 operate in this mode of vibration.

Perhaps confusingly, the coriolis force manifests at the drive frequency, and, therefore, the frequency and/or phase of the drive mode may be analyzed to determine, for example, the mass flow rate of the fluid within the flow tube 215. That is, as just referenced, the flowtube 215, as it vibrates, may include at least two modes of vibration, where one mode corresponds to a vibration of the flowtube 215 in the drive or driven mode, and a second mode corresponds to a vibration of the flowtube 215 in the coriolis mode. These two modes may have different mode shapes corresponding to the movements (e.g., twisting) of the flowtube 215. A mass flow of fluid within the flowtube 215 causes the coriolis mode shape to oscillate, but at the drive frequency, while, simultaneously, the coriolis mode shape has its own natural frequency that is readily excited by external vibration or other factors.

In other words, there are two aspects to the coriolis mode: its oscillation at the drive frequency (associated with a measurement principle of the flow meter 200), and the free vibration of the coriolis mode at its own frequency (i.e., the coriolis frequency). It is the latter aspect of the coriolis mode that results from, for example, external vibration and other factors. As explained in more detail below, the flow meter 200 is designed to characterize, identify, and/or minimize the effect of this coriolis mode.

Figure 3:
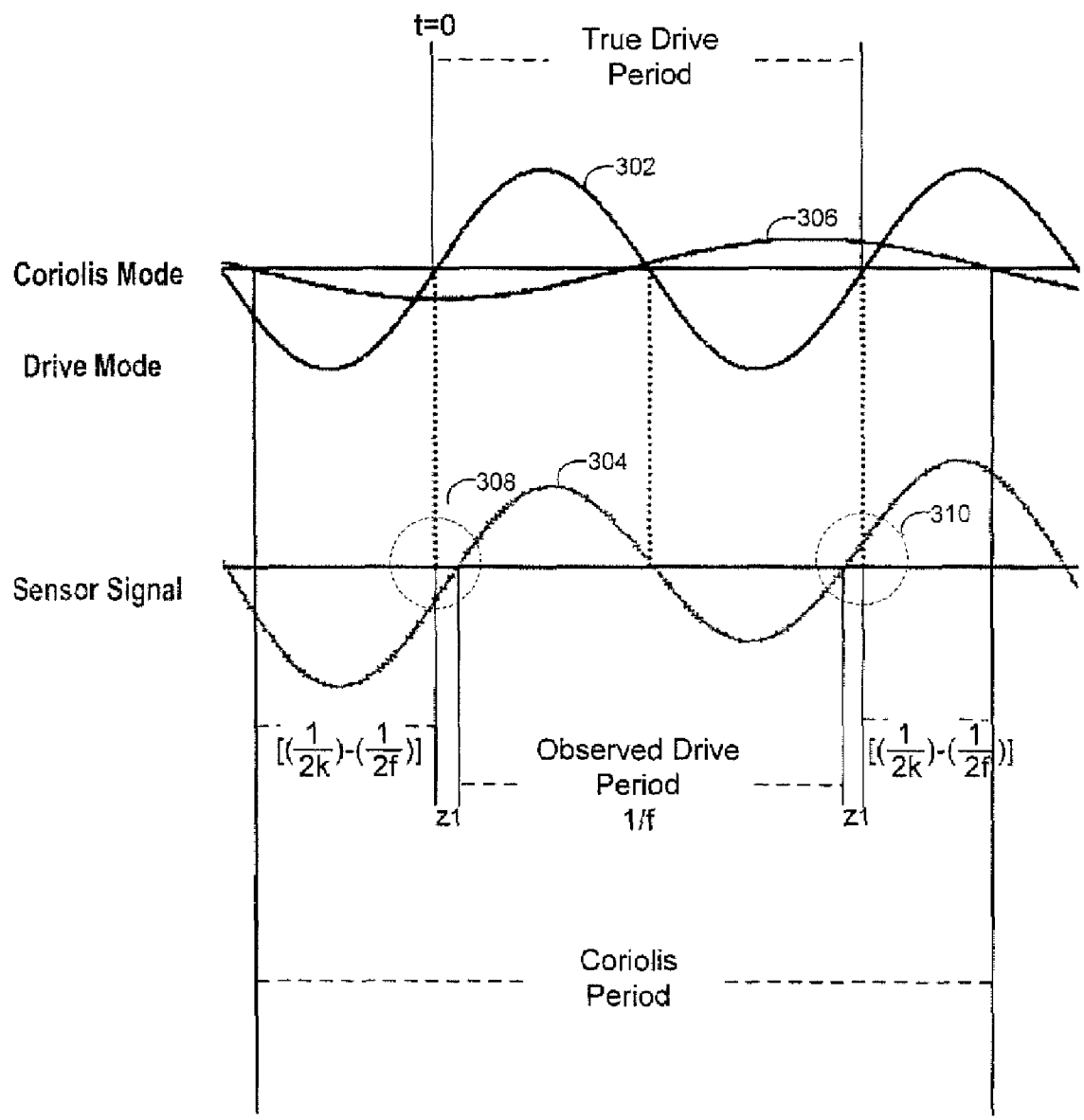
FIG. 3 is a first timing diagram of a sensor signal having a drive mode signal component and a coriolis mode signal component.

Referring briefly to FIG. 3 for illustration of the above-described concepts, a signal 302 reflects the above-described drive mode signal, that is, a signal corresponding to a movement (e.g., velocity) of the flowtube 215, related to a drive signal applied by the driver 210 to the flow tube 215. The drive signal from the driver 210 and the resulting flowtube movement (velocity) should, ideally, be in phase with one another, but are different quantities, and, in particular, the former is generally represented in mA and the latter in mV. Therefore, it should be understood that in the following description, the signal 302 does not represent the drive signal that is output by the driver 210, but, rather, represents a drive mode signal that corresponds to a driven mode of vibration of the flowtube 215 that is excited by the action of the drive signal from the driver 210 on the flowtube 215.

A signal 304 represents a sensor signal that is detected by sensors 205 as a result of the vibration of the flow tube 215. A coriolis mode signal 306, or coriolis signal 306, illustrates the coriolis mode contaminant just referred to. Thus, the sensor signal 304 is composed of at least two modes of vibration: the drive mode signal 302 and the coriolis mode signal 306. The drive mode signal 302 and the coriolis mode signal 306 also may be referred to as the drive frequency signal 302 and the coriolis frequency signal 306, or the drive signal component 302 and the coriolis signal component 306, or the drive frequency component 302 and the coriolis frequency component 306, all respectively, or by similar terminology.

In the example FIG. 3, it may be seen that a frequency of the coriolis mode signal 306 is less than a frequency of the drive mode signal 302 (i.e., the period of the coriolis mode signal 306 is greater than that of the drive mode signal 302). In general, however, the coriolis mode signal 306 may have a frequency that is either less than or greater than that of the drive mode signal 302. Moreover, there may be multiple coriolis mode signals 306, where a first one of the coriolis mode signal may have a frequency less than that of the drive mode signal 302, and a second coriolis mode signal may have a frequency greater than that of the drive mode signal 302. Generally, the coriolis mode signal 306 is a mode of vibration that is generally adjacent to a mode of vibration of the drive mode signal 306. However, the coriolis mode signal 306 need not be particularly close to the drive mode signal 302 in terms of frequency. For example, in the straight flowtube of FIG. 1B, when using the lowest mode of vibration as the drive mode, the next (coriolis) mode of vibration may be two or more times higher, and therefore may be filtered out.

Generally, though, separation (e.g., filtering) or characterization of the coriolis mode signal 306 with respect to the drive mode signal 302 within the sensor signal 304 may be difficult or impossible. Moreover, a response time of the meter 200 may be improved when the coriolis mode signal 306 is as close as possible to the drive mode signal in terms of frequency (thus reducing an efficacy or possibility of filtering), since the coriolis force may then be more easily manifested within the drive mode.

When the drive mode signal 302 corresponds to a lowest mode of vibration of flow tube 215, the coriolis mode signal 306 may be the next highest resident mode above the drive mode signal 302. However, when the drive mode is a relatively high mode of vibration, as just referred to, the coriolis mode signal 306 may be the next lowest resident mode, so that it may be necessary to consider two adjacent modes (both above and below the drive mode). These may be referred to as the upper and lower coriolis mode. In the example of FIGS. 2 and 3, for simplicity's sake, only one coriolis mode is considered. However, it should be understood that the analysis described herein is valid whether a frequency of the coriolis mode signal 306 is lower and/or higher than that of the drive mode signal 302.

Also in FIG. 3, an area 308 and an area 310 are designated as regions of interest for the following discussion. The area 308 includes a time t=0 at which a zero-crossing of the drive mode signal 302 occurs, as well as a zero-crossing of the sensor signal 304 itself. As shown, a time difference or offset z1 exists between these two zero-crossings, which is due to, for example, the presence of the coriolis signal 306 within the sensor signal 304. As referred to above, detection of zero-crossings may be important, for example, in the operations of the flowmeter output unit 240 in determining a frequency of the sensor signal 304, so as to thereby deduce a density of the fluid(s) within the flowtube 215. Thus, the offset z1 may lead to reduced accuracy or complete failure, or reduced efficiency, of the flowmeter output unit 240.

The area 310 also includes the offset z1. As described in more detail below, an additional offset, referred to below as z2, may be present within the sensor signal 304 that is not illustrated for the purposes of discussion of FIGS. 2-6.

In part by characterizing, accounting for, and/or identifying the offset z1, the flowmeter 200 is able to determine characteristics and parameters of the coriolis mode signal 306. Put another way, the flowmeter 200 is able to determine characteristics and parameters of the sensor signal 304 that are related to the drive mode signal 302, and that are not related to the coriolis mode signal 306. Thus, the flowmeter 200 accounts for the causes or reasons for the presence of the coriolis mode signal 306 (e.g., external vibrations, increased flow rate, or a changed percentage of gas within the fluid flow), and outputs mass flow rate and/or density measurements (as well as subsequent drive signals) that are highly accurate, and that are resistant to the causes and effects of the coriolis mode signal 306.

Referring back to FIG. 2, components, operations, and analyses of the flowmeter 200 are illustrated that are used to obtain such accurate and stable operation of the flowmeter 200. For example, the digital transmitter 104 includes a signal analyzer 255 that is operable to receive the sensor signals from the sensors 205 and output at least two characterizations of the sensor signals.

In particular, the signal analyzer 255 outputs a first characterization of the sensor signal(s) 304 in which an influence of the drive mode signal 302 is maximized or emphasized relative to information within the sensor signal 304 that is related to the coriolis signal 306. Further, the signal analyzer 255 outputs a second characterization of the sensor signal(s) 304, in which an influence of the coriolis mode signal 306 parameters are maximized relative to a presence of the drive mode signal 302. In so doing, the first characterization, i.e., the drive-emphasized characterization, may be output to a signal identifier 260 for identification of parameters of the drive mode signal 302. Similarly, but conversely, the signal analyzer 255 outputs the second characterization, i.e., the coriolis-emphasized characterization, of the sensor signals to the signal identifier 260 for identification of the coriolis mode signal 306 parameters.

This general process, as well as various sub-processes, may be iteratively repeated, until a desired level of accuracy is reached with respect to characteristics of the sensor signals 304. That is, the parameters that are generally of interest to the flow meter output unit 240 are those characteristics of the sensor signal 304 that correspond to vibrations of the flow tube only at the drive frequency, uncontaminated by the presence of the coriolis mode signal 306 within the sensor signal 304. These parameters or characteristics of the sensor signal 304 allow the flow meter output unit 240 to determine a mass flow rate and/or density of the fluid within the flow tube 215, and to generate a drive signal to the driver 210 that accurately maintains a desired oscillation of the flow tube 215.

In the implementations described herein, then, these parameters of the sensor signal 304 that reflect characteristics of the drive mode signal 302, and that are referred to herein as drive signal parameters, are referred to as: "A," referring to an amplitude of oscillation of the drive mode signal 302; "f," a frequency of the drive mode signal 302; and "θ," a phase of the sensor signal 304 at the drive frequency when time t=0. Analogously, corresponding parameters of the coriolis mode signal 306 include an amplitude B, a frequency k, and a phase φ.

Thus, by determining an accurate representation of the drive parameters A, f, and θ, the signal analyzer 255 and the signal identifier 260 ensure accurate output and operation of the flow meter output unit 240. Similarly, by determining accurate characterizations of the coriolis mode signal 306 parameters B, k, and φ, the signal analyzer 255 and the signal identifier 260 may assist in the accurate determination of A, f and θ.

Moreover, by determining the coriolis mode signal 306 parameters B, k, and φ, the digital transmitter 104 allows for accurate determination of, for example, characteristics of external vibrations or other factors that lead to a presence in the coriolis mode signal 306 in the sensor signal 304. As a result, such external factors may be extracted from the sensor signal 304, for, for example, analysis of the external event(s) which lead(s) to the determined value of the coriolis mode parameters, or otherwise for responding to these factors and/or eliminating an impact of these factors.

The described techniques for determining the drive and coriolis parameters A, f, θ, B, k, and φ may then be performed on a cycle-by-cycle basis (or more or less frequent, as desired). In this way, information from a previous cycle may be used in calculations (e.g., as initial estimates) performed on the next cycle. Moreover, changes in the sensor signal 304 may be detected and characterized within the same or following period of the sensor signal in which the changes occur.

As described in more detail below, the signal analyzer 255 operates by implementing a zero-crossing detector 255 that analyzes the sensor signal 304 to determine a time at which the sensor signal 304 crosses a zero value, e.g., within areas 308 and 310 in FIG. 3. As is known, such detected zero crossings may be used to calculate a period, and thus a frequency, of the sensor signal 304.

A frequency calculator 270 may be used to receive an output of the zero-crossing detector 265, to calculate the frequency f of the sensor signal 304. Then, a frequency k of the coriolis mode signal 306 may be determined from the frequency f. For example, it is often the case that an existing relationship between the frequency f and the frequency k is known. For example, the frequency k may be expressed as the frequency f reduced by a factor of $\sqrt{3}$, or by some other factor.

Once the frequency f and k are known, an integrator 275 may be used to perform two characterizations of the sensor signal 304. That is, as described above, the integrator 275 may perform a first integration of the signal 304 in which parameters A, f, and θ of the drive mode signal 302 within the sensor signal 304 are maximized or emphasized relative to the coriolis mode parameters B, k, and φ of the coriolis mode signal 306 that are present within the sensor signal 304. As a result, the integrator 275 may output a drive-emphasized characterization of the sensor signal 304 to the signal identifier 260, in which the effect of parameters B, k, and φ the coriolis mode signal 306 is minimized or eliminated.

Similarly, the integrator 275 may perform a second integration in which parameters or characteristics B, k, and φ of the coriolis mode signal 306 within the sensor signal 304 are maximized or emphasized relative to the corresponding drive signal parameters A, f, θ, within the sensor signal 304. The result is a coriolis-emphasized characterization being output by the integrator 275 to the signal identifier 260.

The signal identifier 260 receives the integration results, i.e., the drive-emphasized characterization of the sensor signal 304 and the coriolis-emphasized characterization of the sensor signal 304, within integration results 280. This function of the integrator 275 also may be referred to as mode maximization; i.e., the integrator 275 performs a first integration to maximize an effect of the drive mode signal 302 within the sensor signal 304 (minimizing the effect of the coriolis mode signal 306), and performs a second integration to maximize an effect of the coriolis signal 306 within the sensor signal 304 (minimizing the effect of the drive mode signal 302).

For example, the integrator 275 may perform the two integrations as numerical integrations of the sensor signal 304, examples of which are provided in more detail below. Then, the results of these numerical integrations may be stored within the integration results 280.

A second memory or database 285 stores initial and/or revised estimates of the various signal parameters to be calculated. Accordingly, a parameter calculator 290 inputs the integration results and the initial parameter estimates, and calculates remaining ones of the parameters, as well as improved values for the parameter estimates. The same or similar parameter estimates may be used by the signal analyzer 255, so that the parameter estimates database 285 is illustrated within the signal analyzer 255, as well. Of course, both the signal analyzer 255 and the signal identifier 260 may access the same or different parameter estimates database(s) 285.

An example of an operation of the signal analyzer 255 is provided in more detail below with respect to FIGS. 3 and 4. In particular, it should first be understood that known techniques for determining the amplitude A and phase data θ on the sensor signal 304 include a Fourier analysis of the signals 304, as described in detail in, for example, commonly-assigned U.S. Pat. No. 6,311,136, which is incorporated by reference above. Within such analysis, for example, an integration may be performed over a period of the sensor signal 304 that is presumed to equate to a period of the drive mode signal 302, as illustrated by Eqs. 1, 1a, 2 and 2a, below:

$$\text{I\_S}(A, f, \theta) := \int_0^{\frac{1}{f}} A \cdot \sin[(2 \cdot \pi \cdot f \cdot t) + \theta] \cdot \sin(2 \cdot \pi \cdot f \cdot t) dt \quad \text{Eq. (1)}$$

$$\text{I\_S}(A, f, \theta) = \frac{1}{2f} A \cos(\theta) \quad \text{Eq. (1a)}$$

$$\text{I\_C}(A, f, \theta) := \int_0^{\frac{1}{f}} A \cdot \sin[(2 \cdot \pi \cdot f \cdot t) + \theta] \cdot \cos(2 \cdot \pi \cdot f \cdot t) dt \quad \text{Eq. (2)}$$

$$\text{I\_C}(A, f, \theta) = \frac{1}{2f} A \sin(\theta) \quad \text{Eq. (2a)}$$

As may be seen, Eqs. (1) and (2) rely on integrations with modulating functions $\sin(2\pi ft)$ and $\cos(2\pi ft)$, respectively. Eqs. (1) and (2) may be simplified into Eqs. (1a) and (2a), respectively, which may be manipulated to determine analytical expressions for A and θ, as shown in Eqs. (3) and (4):

$$A\_est := 2 \cdot f \sqrt{\text{I\_S}^2 + \text{I\_C}^2} \quad \text{Eq. (3)}$$

$$\theta\_est := \text{atan}\left(\frac{\text{I\_C}}{\text{I\_S}}\right) \quad \text{Eq. (4)}$$

Thus, given values for the functions I_S and I_C, as well as the frequency f, estimates for the values of A and θ may be obtained.

In summary, then, the expressions, for example, A sin(2πt+θ) and A cos(2π+θ) represent the sensor signal 304. Higher harmonics of the sensor signal may be present without impacting the results of Eqs. (1)-(4), since the zero-crossings of the harmonics will, by definition, be the same as the zero-crossings of the sensor signal 304 itself, and the Fourier analysis is designed to eliminate the influence of such harmonics. In Eqs. (1) and (2), the sensor signal 304 is multiplied through by a pure sine or cosine modulating function (i.e., $\sin(2\pi ft)$ and $\cos(2\pi ft)$, respectively) at the drive frequency f, and integrated over one complete drive cycle, as described above.

As a result of these operations, a phase difference between a plurality of the sensor signals 304, which is approximately proportional to a mass flow rate of fluid within the flow tube 215, may be determined by determining a difference between observed phase data on two separate sensor signals (e.g., a difference in θ for two different sensors). Further, since the frequency is known, a density of the material also may be determined. Still further, these factors, along with the determined value for the amplitude A, may be used to generate a drive signal to the driver(s) 210 such that a desired oscillation of the flowtube 215 is maintained. The analysis of Eqs. (1)-(4) does not specifically consider an impact of the coriolis mode signal 306, and, therefore, may be sufficient when there are little or no disturbances or other factors that may lead to a presence of the coriolis mode signal 306 in the sensor signal 304.

In FIGS. 2 and 3, however, the presence and impact of the coriolis mode signal 306 is considered, as referenced above and described in more detail, below. Specifically, for example, the integrator 275 performs a related analysis to that of Eqs. (1)-(4), but performs an integration(s) based on the period of operation of the coriolis mode signal 306, as opposed to the period of oscillation of the drive mode 302.

For example, in the examples that follow, the integration interval is extended symmetrically in both directions away from the zero crossings of the drive mode signal 302, so as to encompass an entirety of a period of oscillation of the coriolis mode signal 306. In other words, rather than integrating over a period from time t=0 to time t=1/f, the period of integration is extended negatively by value of [(½k)−(½f)], and is extended in a positive direction from an end of the relevant drive cycle by a corresponding amount [(½k)−(½f)], as illustrated in FIG. 3.

This approach results in alterations to the integral limits of Eqs. (1) and (2), and, in particular, in addition to altering the limits themselves, alters the modulation functions, as described in more detail below. As also described below, further alteration of the modulation functions in this context allows for the mode maximization capabilities of the integrator 255, as described above. For example, if a first modulation function is used that is twice the coriolis mode frequency (i.e., 2k), then the influence of the drive mode will be maximized, while the influence of the coriolis mode will be reduced or eliminated. If, however, a second modulation function that is equal to the coriolis frequency (k) is used, then an influence of the coriolis mode will be maximized. Equations 5-8 provide an example of the first-described modulation function that is twice the coriolis mode frequency.

Specifically, Eq. (5) illustrates the CS2_z1 integral. That is, using the notation above, Eq. (5) represents a form of Eq. (1) above, but with a number of points of note regarding the form and notation used with respect to Eq. (5). First, Eq. (5) includes a "B" term (i.e., B sin [2πkt+φ]) representing the Coriolis mode signal 306, in addition to the "A" term of Eq. (1) that represents an effect of the drive mode signal 302. That is, Eq. (5) takes a general form of "integral value=(A or drive mode term)+(B or coriolis mode term)" that is seen throughout the following equations and discussion.

Second, Eq. (5) has integral limits extended to encompass a full cycle of the coriolis mode, which, again, is indicated in Eq. (5) by the "B" term. Third, Eq. (5), like Eq. (1), represents the sine term of the Fourier analysis, as represented by the "S" term. Fourth, Eq. (5) has a modulation function with frequency 2k, designated by the use of (4πk) in the modulation function and by the "2" term in the expression CS2_z1. Fifth, as designated by the z1 term in the CS2_z1 expression, Eq. (5) includes the offset value z1 in the integral limits, and thereby in the modulation function, in order to take into account an effect of the altered zero-crossing of the sensor signal 304 discussed above with respect to areas 308 and 310 of FIG. 3.

$$\text{CS2\_z1\_int}(A, f, B, k, \phi, z1) := \quad \text{Eq. (5)}$$

$$\int_{-\left(\frac{1}{2k}-\frac{1}{2f}\right)+z1}^{\frac{1}{f}+\left(\frac{1}{2k}-\frac{1}{2f}\right)+z1} [B \cdot \sin[(2 \cdot \pi \cdot k \cdot t) + \phi] + A \cdot \sin(2 \cdot \pi \cdot f \cdot t)] \cdot$$

$$\sin\left[4 \cdot \pi \cdot k \cdot \left[t - z1 + \left(\frac{1}{2k} - \frac{1}{2f}\right)\right]\right] dt$$

Further in the expression of Eq. (5), it should be understood that the integral limits are expressed such that a point of zero phase for the drive mode component (A term) occurs at time t=0 in FIG. 3, while the zero crossing point of the sensor signal 304 occurs at time t=z1, due to the presence of the coriolis mode component 306 within the sensor signal 304. This notation may be selected to reflect calculations performed within the integrator 275, in which integrations are generally performed between zero-crossings, rather than starting at z1, since, at the time of integration, a value of z1 is generally not known.

Having expressed this CS2_z1 integral, an analytical expression for its value may be expressed in terms of its parameters f, k, A, z1, B, φ, and z1. As seen below, and generally speaking, analytical forms for each of the A term and the B term of Eq. (5) may be determined, and, in particular, B terms may turn out to be exactly zero. Thus, for the A term of Eq. 5, analogous to Eq. (1a), may be determined and is expressed in Eq. (6):

$$CS2\_z1(A, f, B, k, \phi, z1) := \qquad \text{Eq. (6)}$$
$$\frac{-2 \cdot k \cdot A}{\pi \cdot (f^2 - 4 \cdot k^2)} \cdot \sin\left(\frac{f}{k} \cdot \pi\right) \cdot \cos(2 \cdot f \cdot \pi \cdot z1)$$

A corresponding expression for the B term of Eq. (5) may be determined to be zero, which was the first desired result of the integrator (mode maximizer) 275, as described above. That is, Eq. (6) provides the first term of the first pair of integrals in which the drive mode is emphasized or maximized relative to the coriolis mode, and, in fact, Eq. (6) obtains the desired result of eliminating the coriolis mode (B term) entirely, so that Eq. (6) may be considered to be the analytical result of an entire integration of Eq. (6), having the above term for A and with the B term entirely eliminated. As explained, this result is obtained naturally from extending the integral limits and doubling the modulation function frequency, and takes into account the effect of the offset z1.

A corresponding analysis may be performed with respect to Eq. (2), i.e., the cosine term of the Fourier analysis. Using the notation above, Eq. (7) represents the CC2_z1 integral. That is, the first "C" again designates the integration over the full coriolis mode cycle, the second "C" designates the fact that the cosine term is being represented, and the "2" represents doubling of the modulation frequency.

$$CC2\_z1\_int(A, f, B, k, \phi, z1) := \qquad \text{Eq. (7)}$$
$$\int_{-\left(\frac{1}{2k} - \frac{1}{2f}\right)+z1}^{\frac{1}{f}+\left(\frac{1}{2k} - \frac{1}{2f}\right)+z1} [B \cdot \sin[(2 \cdot \pi \cdot k \cdot t) + \phi] + A \cdot \sin(2 \cdot \pi \cdot f \cdot t)] \cdot$$
$$\cos\left[4 \cdot \pi \cdot k \cdot \left[t - z1 + \left(\frac{1}{2k} - \frac{1}{2f}\right)\right]\right] dt$$

As with Eq. (6), an analytical expression for Eq. (7) may be obtained, and is shown below as Eq. (8).

$$CC2\_z1(A, f, B, k, \phi, z1) := \qquad \text{Eq. (8)}$$
$$\frac{-A \cdot f}{\pi \cdot (f^2 - 4 \cdot k^2)} \cdot \sin\left(\frac{f}{k} \cdot \pi\right) \cdot \sin(2 \cdot f \cdot \pi \cdot z1)$$

Again, a similar expression for the B term of Eq. (6) may be shown to be zero, which is the desired result for minimizing the coriolis mode effect and maximizing the effect of the drive mode signal 302. In other words, Eq. (8) provides an analytical expression for CC2_z1 having no B term at all, as it has been cancelled out by using twice the coriolis frequency k (i.e., 2k) as a modulation function and integrated over the coriolis period.

Thus, Eq. (8) represents the second term in the first pair of integrals output by the integrator (mode maximizer) 275, in which the drive mode signal 302 is emphasized relative to the coriolis mode. That is, in this example, the drive-emphasized characterization of the sensor signal 304 includes the pair of integrals CS2_z1 and CC2_z1 of Eqs. (6) and (8), respectively.

As described below, Eqs. (6) and (8) may be used in a manner analogous to Eqs. (3) and (4) above, in order to obtain solvable expressions for A and z1, respectively. An accuracy of these values will be increased with respect to what may be calculated from Eqs. (3) and (4) when applied to a sensor signal contaminated with the coriolis mode component 306, however, since the effect of the coriolis signal 306 is minimized in Eqs. (6) and (8).

Further, these improved values of A and z1 may be used to more-accurately determine values for corresponding terms B and φ of the coriolis mode signal 306 itself, which may themselves then be used to determine yet-more accurate values for A and z1. This process may be iteratively repeated until a desired level of accuracy is reached. Then, the value A may be used to generate appropriate parameters for a new drive signal to be applied to the flowtube 215, and the value z1 for a first sensor signal from a first sensor may be used together with a corresponding value for z1 determined for a second sensor signal from a second sensor, in order to determine a phase difference between the sensor signals (thereby to determine a mass flow rate of the fluid within the flowtube 215).

Specifically, the corresponding terms B and φ may be determined from Eqs. (9)-(14), below. In Eqs. (9)-(14), the two analogous terms CS1_z1 and CC1_z1 are determined, where again the first term "C" represents the use of integral limits corresponding to an entire drive cycle of the coriolis mode, the second term "S" or "C" represents the sine or cosine term, respectively, and the "1" term designates the use of the frequency k as the modulation frequency.

Accordingly, Eq. (9) represents the CS1_z1 term, in which the only difference between Eq. (9) and Eq. (5) is that the modulation term involves a term of the form $\sin(2\pi k(\ldots))$ instead of $\sin(4\pi k(\ldots))$. Thus, Eq. (9) may be written as:

$$CS1\_z1\_int(A, f, B, k, \phi, z1) := \qquad \text{Eq. (9)}$$
$$\int_{-\left(\frac{1}{2k} - \frac{1}{2f}\right)+z1}^{\frac{1}{f}+\left(\frac{1}{2k} - \frac{1}{2f}\right)+z1} [B \cdot \sin[(2 \cdot \pi \cdot k \cdot t) + \phi] + A \cdot \sin(2 \cdot \pi \cdot f \cdot t)] \cdot$$
$$\sin\left[2 \cdot \pi \cdot k \cdot \left[t - z1 + \left(\frac{1}{2k} - \frac{1}{2f}\right)\right]\right] dt$$

Eq. (9) has an analytical expression for the A term that is shown in Eq. (10):

$$CS1\_Aonly\_z1(A, f, B, k, \phi, z1) := \qquad \text{Eq. (10)}$$
$$\frac{-k \cdot A}{\pi \cdot (f^2 - k^2)} \cdot \sin\left(\frac{f}{k} \cdot \pi\right) \cdot \cos(2 \cdot f \cdot \pi \cdot z1)$$

Eq. (9) has an analytical expression for the B term that is shown in Eq. (11):

$$CS1\_Bonly\_z1(A, f, B, k, \phi, z1) := \qquad \text{Eq. (11)}$$
$$\frac{-B}{2 \cdot k} \cdot \cos\left[k \cdot \pi \cdot \left(\frac{1}{f} + 2 \cdot z1\right) + \phi\right]$$

As seen below, the B term of Eq. (10) is maximized with respect to the A term of Eq. (11), although the A term does not go to zero.

Similar analysis may be performed for the cosine term of the coriolis-emphasized (i.e., B term maximized) characterization of the sensor signal 304 that is output by the integrator 275. This cosine term is expressed as CC1_z1, as shown in Eq. (12):

$$CC1\_z1\_int(A, f, B, k, \phi, z1) := \\ \int_{-\left(\frac{1}{2k}-\frac{1}{2f}\right)+z1}^{\frac{1}{f}+\left(\frac{1}{2k}-\frac{1}{2f}\right)+z1} [B \cdot \sin[(2 \cdot \pi \cdot k \cdot t) + \phi] + A \cdot \sin(2 \cdot \pi \cdot f \cdot t)] \cdot \\ \cos\left[2 \cdot \pi \cdot k \cdot \left[t - z1 + \left(\frac{1}{2k} - \frac{1}{2f}\right)\right]\right] dt \quad \text{Eq. (12)}$$

Eqs. (13) and (14) represent the analytical expressions for the A term and B term, respectively, of Eq. (12).

$$CC1\_Aonly\_z1(A, f, B, k, \phi, z1) := \\ \frac{-f \cdot A}{\pi \cdot (f^2 - k^2)} \cdot \sin\left(\frac{f}{k} \cdot \pi\right) \cdot \sin(2 \cdot f \cdot \pi \cdot z1) \quad \text{Eq. (13)}$$

$$CC1\_Bonly\_z1(A, f, B, k, \phi, z1) := \\ \frac{-B}{2 \cdot k} \cdot \sin\left[k \cdot \pi \cdot \left(\frac{1}{f} + 2 \cdot z1\right) + \phi\right] \quad \text{Eq. (14)}$$

As with Eqs. (10) and (11), above, and as described in more detail below, the B term of Eq. (13) is maximized with respect to the A term of Eq. (14). As a result, expressions for B and φ, analogous to Eqs. (3) and (4), respectively, may be determined, so that B and φ may be determined to a relatively high degree of accuracy, particularly since improved-accuracy A and z1 terms above may be used in the calculations thereof.

Further explanation and examples for the derivation and use of Eqs. (5)-(14) are provided in more detail below, and, in particular, with respect to FIGS. 12-15, including further explanation for the above described selection of the first and second modulation functions. However, with respect to the described operations of FIGS. 2-11, and associated examples, it is enough to understand that the integrator 275 is operable to perform a numerical integration of the sensor signal 304, over a time interval defined by a period of the coriolis mode signal 306 with respect to a period of the drive mode signal 302, including the zero-crossing offset z1 that results from the presence of the coriolis mode signal 306. As a result, the integrator 275, as described above, outputs a drive-emphasized characterization of the sensor signal 304 as a first pair of integrals CS2_z1 and CC2_z1, and a coriolis-emphasized characterization of the sensor signal 304 as a second pair of integrals CS1_z1 and CC1_z1.

As a result, the signal analyzer 255 and the signal identifier 260 of FIG. 2 may be considered to be a contaminant determination or detection system, that is operable to determine actual values for contaminant signals, such as the coriolis mode signal 306, within the sensor signal 304. Moreover, these values may be determined on a cycle-by-cycle basis, even when the drive mode signal 302 is very close to the contaminant signal, and without requiring filtering of the contaminant signal. A key philosophy is that the motion sensor signal is not filtered prior to the integration process, for example in order to reduce the influence of any specific mode of vibration, thus avoiding any loss of dynamic response. As a result, a dynamic response of the flowmeter 200 is very good, and, in particular, a response of the flowmeter both to changing flow parameters of the fluid within the flowtube 215 (e.g., a change in mass flow rate of the fluid), and to changing contaminant parameters of the contaminant signal (e.g., a change due to an external disturbance of the flowtube, or due to a change in condition of the flowtube, or of the fluid).

Figure 4:
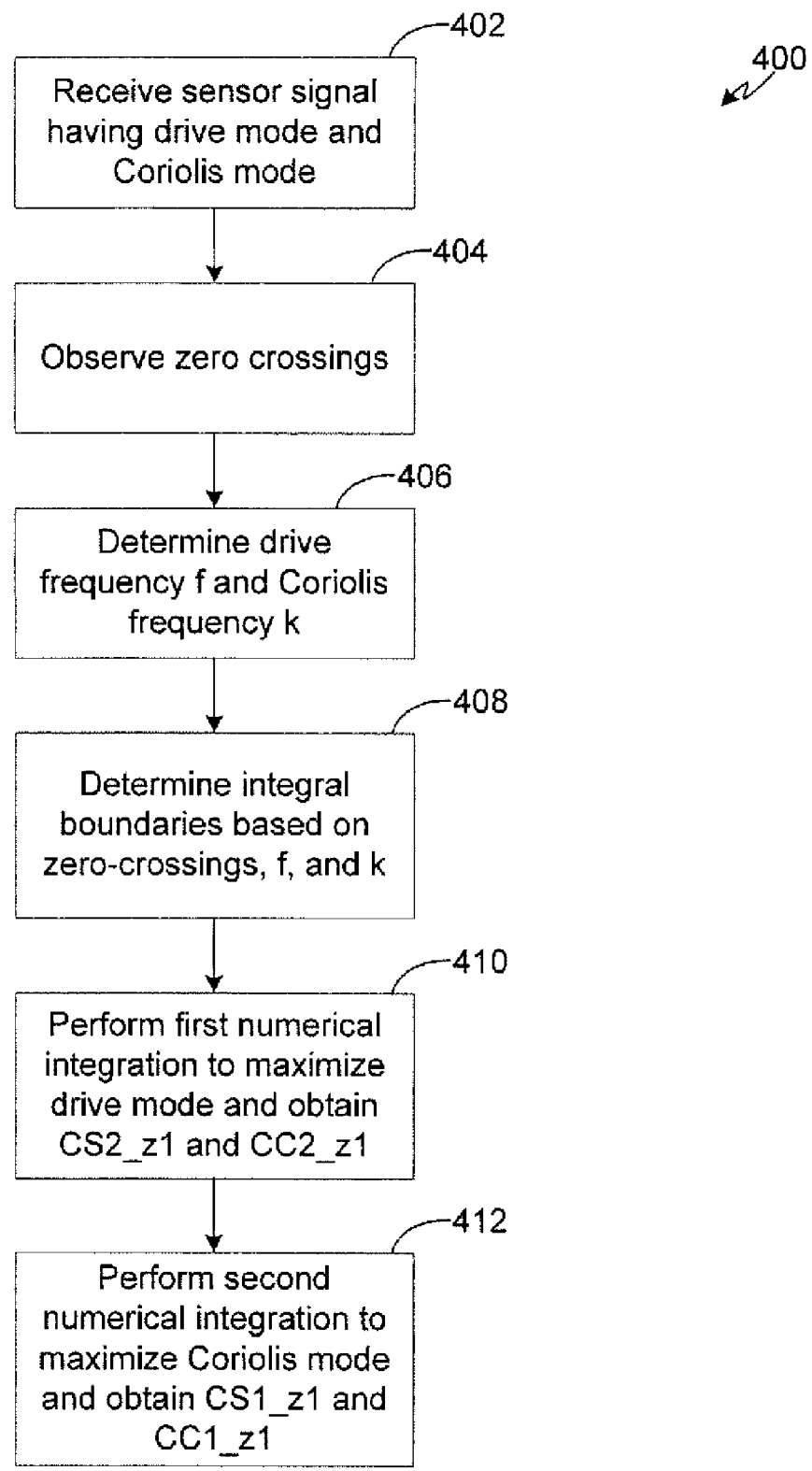
FIG. 4 is a flow chart illustrating an operation of flowmeter of FIG. 2.
Figure 5:
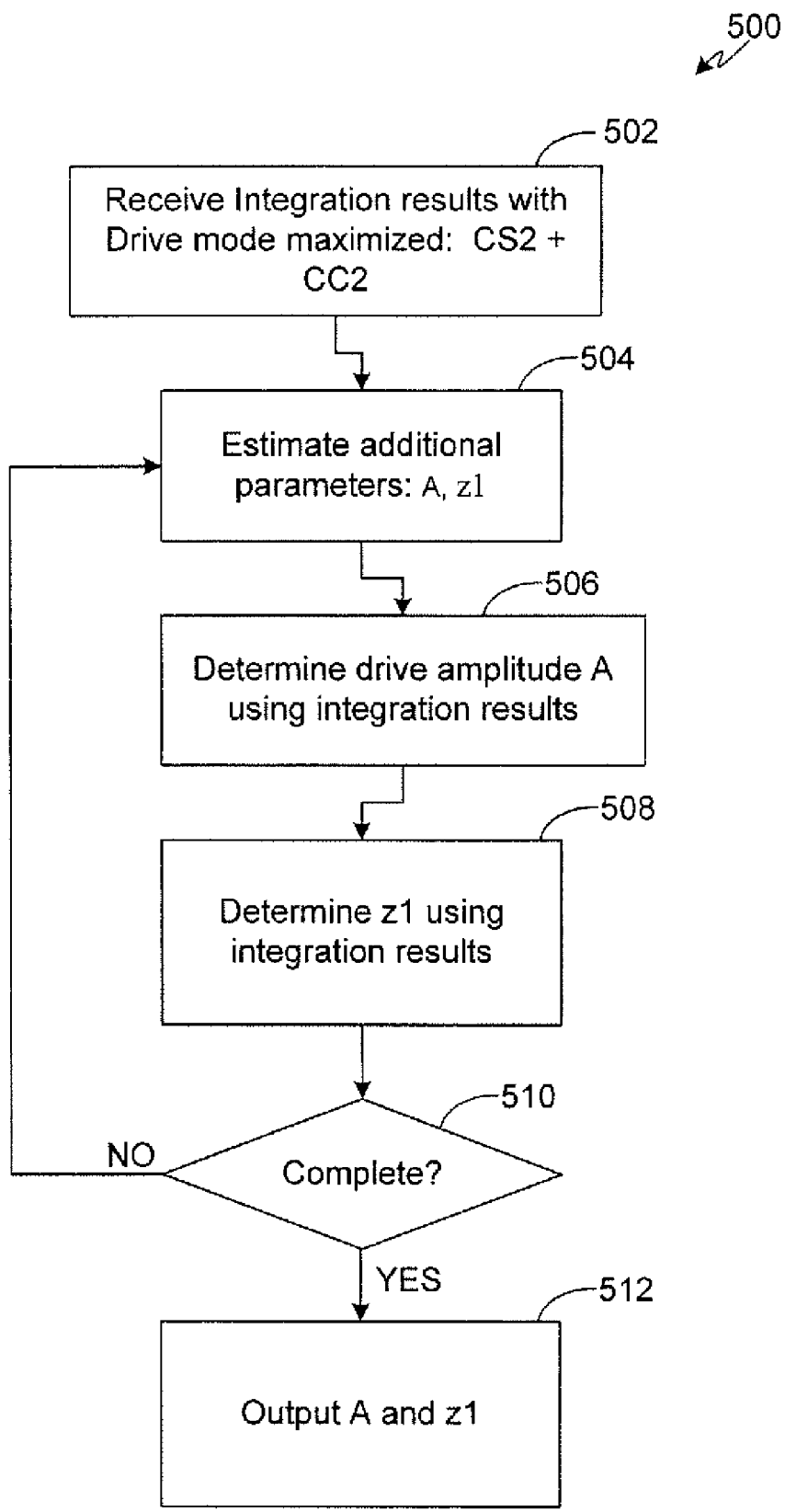
FIG. 5 is a flow chart illustrating a first process of the flowmeter of FIG. 2.
Figure 6:
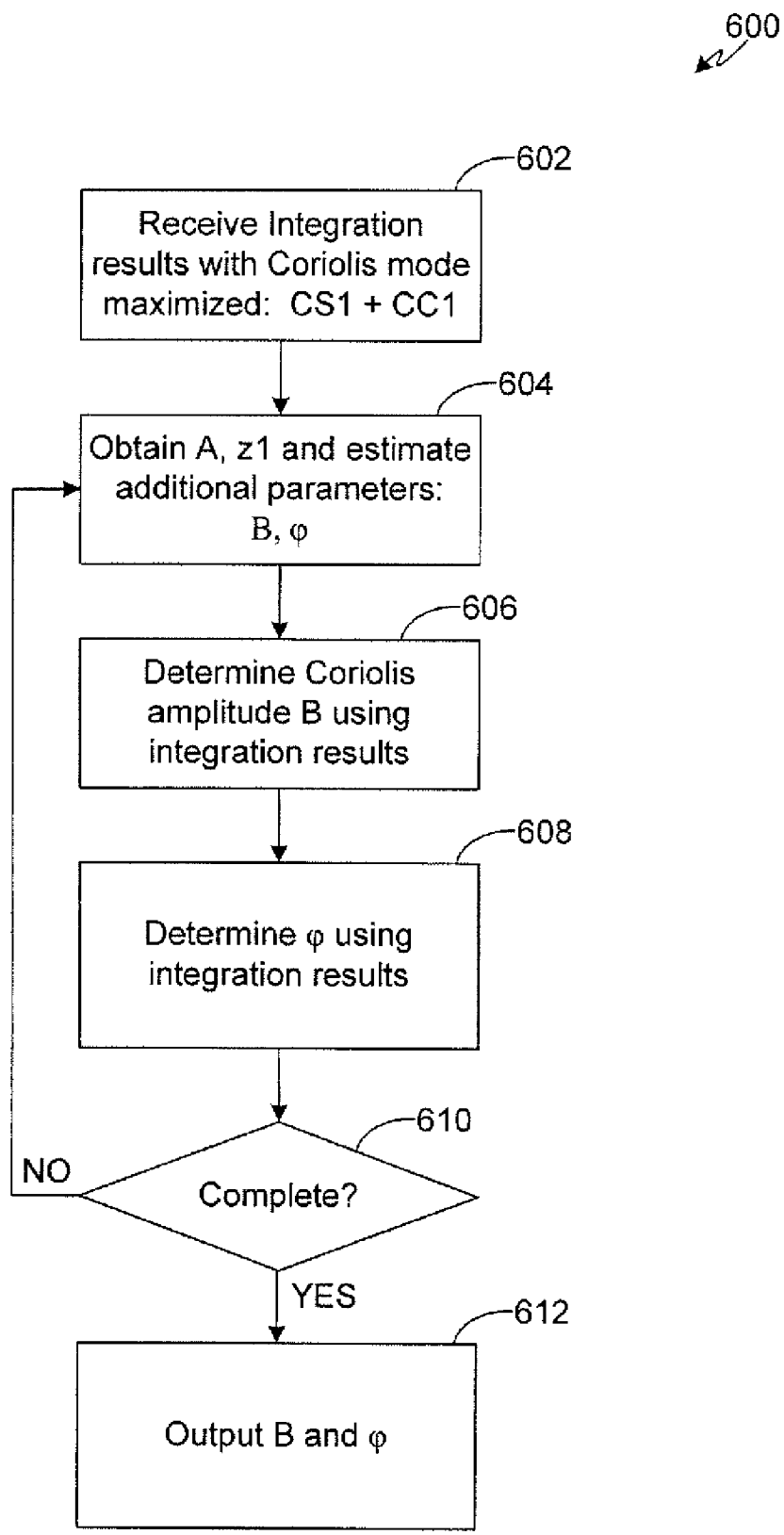
FIG. 6 is a flow chart of a second process of the flowmeter of FIG. 2.

Given the above explanation, FIGS. 4-6 provide an overview of the structure, function, and operation of the signal analyzer 255 and the signal identifier 260 of the flowmeter 200 of FIG. 2.

Specifically, FIG. 4 is a flow chart 400 illustrating an operation of the signal analyzer 255 of FIG. 2. In FIG. 4, the signal analyzer 255 receives the sensor signal 304, which, as explained above, includes portions related to the drive mode signal 302 and other portions related to contaminants, such as the coriolis mode 306 (402).

The zero crossing detector 265 of the signal analyzer 255 analyzes the sensor signal 304 to observe zero crossings of the sensor signal 304 (404). From this information, the frequency calculator 270 is operable to determine the drive frequency f and, thereby, the coriolis frequency k (406). For example, as described above, the drive frequency f may simply be determined to be the intervals of the period of time between two consecutive zero crossings, while frequency k may be determined based on a known relationship between f and k, such as, for example, $k=(\sqrt{3})f$.

With knowledge of f and k, the integrator 275 may determine integral boundaries as described above with respect to Eqs. (5), (7), (9), and (12) (408). That is, the integral boundaries start at the zero crossings, but adjusted for the coriolis mode period rather than the drive mode period, with the knowledge that the observed zero crossings are offset from the true zero crossings by the time offset z1, which is unknown and to be solved for at a later stage for determination of phase difference and mass flow rate.

Accordingly, the integrator 275 may perform a first numerical integration of the sensor signal 304 in which parameters of the drive mode will be maximized (410). The result of this calculation is the first pair of integrals CS2_z1 and CC2_z1 of Eqs. (5) and (7), respectively.

Similarly, the integrator 275 may perform a second numerical integration of the sensor signal 304, in which the parameters of the coriolis mode signal 306 are maximized (412). The result of this calculation is the second pair of integrals CS1_z1 and CC1_z1, related to Eqs. (9) and (12), respectively.

FIG. 5 is a flow chart 500 illustrating a first process of the signal identifier 260 of FIG. 2. In FIG. 5, the signal identifier 260 receives first integration results from the integrator 275, where the first integration results provide the drive-emphasized characterization of the sensor signal 304 (502). That is, as described above, the integration results include the values CS2_z1 and CC2_z1 of Eqs. (5) and (7), respectively.

The parameter calculator 290 receives these integration results 280, and obtains estimates for the parameters A and z1 (504). Sufficiently rough estimates for values for the parameters A and z1 may be determined based on, for example, knowledge of these parameters gained from the immediately-previous cycle, on the assumption that the $$A\_est\_CS2(CS2\_z1\_val, CC2\_z1\_val, f, k) := \\ \sqrt{\left(\frac{CC2\_z1\_val}{f}\right)^2 + \left(\frac{CS2\_z1\_val}{2k}\right)^2} \cdot \left[\frac{\pi \cdot (f^2 - 4k^2)}{\sin\left(\frac{f}{k} \cdot \pi\right)}\right] \quad \text{Eq. (15)}$$

parameters will not have changed by a large amount between close or consecutive cycles. Estimates also may be determined from, for example, the type of flow tube 215 being used, or based on a value of the drive frequency f, or from the use of Eqs. (1)-(4), above, or from other known sources. As mentioned, such parameter estimates may be calculated and stored with respect to the parameter estimates database 285.

The parameter calculator 290 may determine an improved value for the drive amplitude A, using the integration results CS2_1 and CC2_z1, along with Eq. (15), which, as referenced above, provides an analytical expression for the value A that is analogous to Eq. 3.

In Eq. 15, it should be understood that the terms CS2_z1_val and CC2_z1_val represent numerical values for the CS2_z1 and CC2_z1 integrals, which are determined by the integrator 275 and output to the signal identifier 260.

Subsequently, the numerical values for the CS2_z1 and CC2_z1 integrals may be used to determine an improved value for the parameter z1 (508), using Eq. (16) (in which a tan is the inverse tangent function), which is analogous to Eq. (4), above:

$$z1\_est(CS2\_z1\_val, CC2\_z1\_val, f, k) := \qquad \text{Eq. (16)}$$

$$\frac{\text{atan}\left(\frac{2k \cdot CC2\_z1\_val}{f \cdot CS2\_z1\_val}\right)}{2 \cdot \pi \cdot f}$$

If the values of the drive amplitude A and the zero offset z1 are determined to be accurate (510), then the values A and z1 may be output (512). If, however, additional iterations are desired or required, then the determined values of A and z1 may be used as a starting point for a second iteration of the process 500 (504).

In some implementations, the estimation/iteration process described above for A and z1 may not be necessary or desired. In these cases, the integration results (502) may be used to determine A (506) and z1 (508) directly, and the obtained values may be sufficiently accurate for a given design or purpose, without the need to use initial estimates and subsequent iterations to convergence(s).

FIG. 6 is a flow chart 600 of a second process implemented by the signal identifier 260 of FIG. 2. In FIG. 6, the parameter calculator 290 receives the second integration results with the coriolis mode parameters maximized therein (602). That is, the signal identifier receives from the integrator 275 the coriolis-emphasized characterization of the sensor signal 304, expressed as numerical values calculated for the integrals CS1_z1 and CC1_z1 of Eqs. (9) and (12), respectively, in which the coriolis frequency k is used with the modulation function(s) of those expressions.

The parameter calculator 290 then obtains the values for the drive amplitude A and the zero crossing offset z1 that were previously obtained as an output of the process 500 of FIG. 5, and estimates the coriolis parameters of amplitude B and phase $\phi$ (604). As referenced above, the initial estimates for parameters B and $\phi$ may be obtained based on knowledge of these parameters from previous cycles, and/or based on knowledge of the already-determined parameters of, for example, f, k, A, and z1.

Similarly to the process 500 of FIG. 5, then, the coriolis amplitude B may be determined based on the integration results CS1_z1 and CC1_z1 (606). Specifically, the procedure summarized in Eq. (17) may be used in this calculation, which is analogous to Eqs. (3) and (15), but for the B term:

$$B\_est\_CS1(A, f, k, z1, CS1\_val, CC1\_val) := \qquad \text{Eq. (17)}$$

$$\begin{vmatrix} c \leftarrow CC1\_val - CC1\_Aonly\_z1(A, f, 0, k, 0, z1) \\ s \leftarrow CS1\_val - CS1\_Aonly\_z1(A, f, 0, k, 0, z1) \\ 2 \cdot k \cdot \sqrt{c^2 + s^2} \end{vmatrix}$$

In Eq. (17), the terms "c" and "s" are numerical estimates of the integral values CC1_Bonly_z1 and CS1_Bonly_z1. They may be obtained by subtracting estimates of the influence of A in these integrals (i.e., CC1_Aonly_z1 and CS1_Aonly_z1) from the numerical values of CC1_z1 and CS1_z1, or CC1_z1_val and CS1_z1_val, as defined by the analytical results given in Eqs. (13) and (10), above. Then, as shown, the resulting values of c and s are combine in a root-sum-square manner to obtain the estimate for B.

Then, the integration results CS1_z1 and CC1_z1 and determined value of z1 may be used to determine a value of $\phi$ (608), as shown in Eq. (18) and analogously to Eqs. (4) and (16), above, where the terms c and s are defined for Eq. (17), above:

$$\phi\_est\_CS1(A, f, k, z1, CS1\_val, CC1\_val) := \qquad \text{Eq. (18)}$$

$$\text{atan}\left(\frac{s}{c}\right) - k \cdot \pi \cdot \left(\frac{1}{f} + 2z1\right)$$

If the determined values of B and $\phi$ are sufficiently accurate (610), then the values B and $\phi$ may be output (612). Otherwise, as in FIG. 5, additional iterations may be performed to improve the resulting values of B and $\phi$.

As a further alternative, and again as explained above for FIG. 5, it may not be necessary to obtain initial estimates of B and $\phi$ for performing subsequent iterations. Rather, sufficiently accurate results may be obtained in some implementations by determining B (606) and $\phi$ (608) directly from the integration results CS1_z1 and CC1_z1 (602).

As described above, the process 400 of the signal analyzer 255 results in integration results which characterize the sensor signal 304 in a manner that encompasses all of the information pertaining to both the coriolis mode 306 and the drive mode 302, as well as information related to an offset of the zero crossing of the sensor signal 304 that is caused by the presence of the coriolis mode 306. More specifically, the process 400 of the integrator 275 results in a first pair of integration results CS2_z1 and CC2_z1 in which parameters of the drive mode signal 302 are maximized or emphasized relative to the parameters of the coriolis mode signal 306. Further, the integrator 275 outputs a second pair of integration results CS1_z1 and CC1_z1 which provide a coriolis-enhanced characterization of the sensor signal 304, in which the coriolis parameters B and $\phi$ are maximized or emphasized within the integration results relative to the drive parameters A and z1.

Subsequently, process 500 uses the drive emphasized characterization of the sensor signal 304, i.e., the integration results CS2_z1 and CC2_z1, in which a modulation function that is twice a frequency of the coriolis mode is used. These drive-emphasized characterizations may then be used to determine the parameters A and z1, related to the drive mode signal 302. Similarly, the process 600 of the signal identifier 260 uses the coriolis-enhanced characterization of the sensor signal 304, i.e., the integration results CS1_z1 and CC1_z1 in which a modulation function having a frequency equal to that of the coriolis mode signal 306 is used, to obtain the coriolis mode parameters B and φ.

Some or all of the processes 400-600 may be performed at each cycle of the drive mode signal 302, or may be performed twice per cycle of the drive mode signal 302, or may be performed at some other interval. The processes 400-600 may be iterated until acceptable values for the parameters A, B, z1, and φ are determined. Further, as described in more detail below, these parameters and related information may then be used to determine improved estimates for the frequencies f and k, whereupon the processes 400-600 may be performed again, using these improved frequency estimates.

Once acceptable values for f, A, and z1 are determined (specifically, once values of z1 for two different sensor 205 are determined relative to one another), the flow meter output unit 240 may use these values to determine and output a mass flow rate and/or density of fluid within the flow tube 215 and may further use the parameters f, A, and z1 to generate an appropriate new version of the drive mode signal 302 for maintaining oscillation of the flow tube 215.

Since the flow meter output unit 240 receives very accurate values for the drive signal parameters f, A, and z1 from the signal identifier 260, the flow meter output unit 240 is able to output correspondingly accurate values for the mass flow rate, density, and new drive signal parameters, even in the presence of a strong coriolis mode signal that may be caused by, for example, external vibration to the flow tube 215, sudden changes in flow rate of the fluid within the flow tube 215, or some other causes.

Further, such transient effects that appear as large parameter values B and φ of the coriolis mode signal 306 may be isolated and identified for analysis thereof. For example, it may be the case that the flow tube 215 is subject to external vibrations of unknown source, duration, and/or magnitude. In this case, the results of such external vibrations may be analyzed through the above-described analysis of the coriolis mode signal 306. In this way, the external vibration and characteristics thereof may be characterized and/or determined.

Moreover, the above-described, cycle-by-cycle, active tracking of the coriolis mode component 306 permits and facilitates active control of an amplitude B thereof. For example, an excessive coriolis amplitude B (due to external disturbances, onset of two-phase flow, or other factors) may be suppressed through the inclusion of an inverse coriolis mode component within the drive signal that is output by the driver(s) 210 and applied to the flowtube 215. In other words, a negative drive gain may be applied that reduces or cancels out an effect of the existing coriolis mode component 306.

Still further, the coriolis mode signal component 306 may be used to perform general diagnostics regarding a current state or condition of the flowtube 215. For example, similar conditions may occur over a period of time, e.g., a given disturbance may occur periodically, or an onset of two-phase flow may occur on a regular or semi-regular basis. However, the coriolis mode signal 306 may be determined to be different over time in response to these conditions. The varying (e.g., increasing) coriolis mode parameters may thus be indicative of a changing or changed condition and/or behavior of the flowtube 215, such as, for example, a reduced reliability, or a lowered response time/characteristic.

Finally, and most generally, the basic flow and density calibrations of the meter may vary with the relative positioning of the frequencies of the drive and Coriolis modes respectively. Some flowtube designs are constrained to ensure that this frequency positioning is kept relatively stable over the range of operating drive frequencies of the meter. Using this form of analysis to directly track the relative positions of the drive and Coriolis frequencies, it may be possible to improve flowtube designs by removing the constraint of relative frequency positioning. Alternatively, this analysis can be used to improve the basic mass flow and density measurement on flowtube designs where it is not possible to control the relative positioning of the two mode frequencies, where mass flow and density corrections can be applied if the actual drive and Coriolis frequencies are tracked in real time.

Having described the above examples of general operations 400-600 of the flowmeter 200, the following provides numerical examples of these operations, with reference back to FIGS. 2-6. Specifically, the following example assumes that the signal analyzer 255 determines a frequency f=100 Hz, where a value of the amplitude A of the drive mode signal 302 is assumed to be 0.3V for the purpose of simulating the numerical integration to be performed by the integrator 275, and for comparison to a value for A that is determined using the techniques described herein.

In this case, the frequency k for the Coriolis mode signal 306 is determined to be 57.735 Hz, using the assumption that f=($\sqrt{3}$)k. The amplitude B of the Coriolis mode signal 306, which is typically much smaller than the drive amplitude A, is used in this example as 0.0001V, and the coriolis phase parameter φ may be used as 1.0000 radians. Finally, z1, i.e., the time in seconds between a start of a cycle of the drive mode signal 302 at time t=0 and an observed point of zero phase on the sensor signal 304, may be set as z1=5×10$^6$ s.

For clarity, it is emphasized that the values of A, z1, B and φ given above are the "true" values which are to be deduced from the numerical values of the integrations performed on the sensor data.

Thus, with reference to FIG. 4, it may be seen that the signal analyzer 255 receives the sensor signal 304, determines the frequencies f and k from the observed zero-crossings, and determines integral boundaries for integrating over the Coriolis mode period (402, 404, 406, and 408). With this information, the integrator 275 may use the modulation function having twice the frequency of the Coriolis frequency k to perform a first numerical integration on the sensor signal 304 to obtain the drive-emphasized characterization CS2_z1 and CC2_z1, which, in this example, and using the "true" parameter values for A, B, and z1, as well as the frequencies f and k, calculates as values CS2_z1_val;=−2.46718958053974× 10$^{-3}$ and CC2_z1_val=−6.71250242220871×10$^{-6}$ (410).

Similarly, the integrator 275 may use the modulation function having the same frequency as the Coriolis frequency k to perform a second numerical integration on the sensor signal 304 to obtain the coriolis-emphasized characterization CS1_z1_val and CC1_z1_val, which, in this example, calculates as CS1_z1=6.17617813486415×10$^{-4}$ and CC1_z1=− 3.07891796642618×10$^{-6}$ (412).

Dealing with the drive parameters and drive-emphasized characterization first (as shown in FIG. 5), the parameter calculator 290 of the signal identifier 260 of FIG. 2 may solve for the value of drive amplitude A using Eq. (15), above (506). That is, since, by definition, the values CS2_z1_val and CC2_z1_val include a minimized or zero value for the coriolis amplitude B and phase φ, then using these values in Eq. (15) provides a more accurate value for the amplitude A, which, in this example, turns out to be A=0.299999999999986. Similarly, the parameter calculator 290 may use this improved value of A, along with Eq. (16) above, to solve for an improved value of z1 (508), which, in this example, is z1=5.00000000000295×10$^{-6}$ s.

Dealing with the coriolis parameters and coriolis-emphasized characterization next (as shown in FIG. 6), the parameter calculator 290 of the signal identifier 260 of FIG. 2 may solve for the value of coriolis amplitude B using Eq. (17), above (606). That is, since, by definition, the values CS1_z1_val and CC1_z1_val include a maximized value for the coriolis amplitude B and phase φ, then using these values in Eq. (17) provides a more accurate value for the amplitude B, which, in this example, turns out to be B=1.00000000003168×10$^{-4}$. Similarly, the parameter calculator 290 may use this improved value of B, along with Eq. (18) above, to solve for an improved value of φ (608), which, in this example, is φ=1.00000000000807.

As described above, these calculations may be performed on a cycle-by-cycle basis, such that the values A, B, z1, and φ may be dynamically updated on a regular basis. As a result, the impact of the Coriolis mode signal 306 may be dynamically compensated, at or near real time. For example, in the presence of an external vibration, the flowmeter 200 may nonetheless determine the drive amplitude A and the phase difference θ (using z1 values from different sensors 205), and also may output values for the coriolis amplitude B and phase φ, which will reflect and characterize the presence of the external vibration. As a result, the flowmeter 200 will operate in a continuous fashion, outputting accurate measurements, even in the presence of such disturbances. Moreover, the response time of the flowmeter 200 may be improved with respect to its operation and output during such instances.

In other implementations, the entire processes of FIGS. 4-6 may be iterated in their entirety, in order to obtain even more accurate values for A, z1, B, and φ. Further, improved values for the frequency parameters f and k may be determined (examples techniques are provided below), and these frequency values may be used in subsequent iterations. Still further, the calculations may be performed twice per cycle, rather than once per cycle.

In the latter case, extra calculations may be required which make use of a value z1_offset, that may be defined as a dual value, i.e., either 0.5/f for calculations done from a negative zero crossing to a negative zero crossing, or 0.0 (no effect) for calculations done from a positive zero crossing to a positive zero crossing. In this example, then, the calculated value of z1, above, may be kept as the described value when an absolute value of z1_offset is less than or equal to 0.25/f. Otherwise, the value of z1 may be expressed as z1=z1+z1_offset.

The description of FIGS. 2-6 above acknowledges that the presence of the coriolis mode component 306 in the sensor signal 304 will shift the observed zero crossing at the start of the cycle by time z1 from the "true" zero crossing point of the drive mode component 302 of the sensor signal 304, as shown in FIG. 3. Additionally, however, the zero crossing at the end of the same cycle of the sensor signal 304 may be shifted by a different amount, because of the asynchronous interaction between the drive mode signal 302 and the coriolis mode signal 306, and their respective frequencies f and k.

As a consequence, if the frequency f is estimated based on the period between zero crossings, then the resulting estimate for f may be erroneous. Further, if the integration interval is based on these zero crossings, then additional error may be introduced, and, most importantly, an erroneous frequency will be used for the modulation function.

Consequently, a parameter z2 may be incorporated into the analysis above, where z2 is defined as a time offset between the true period 1/f of the drive mode signal 302 and the observed period between zero crossings that is seen with respect to the sensor signal 304. Then, as above, analytical results may be derived for the resulting integrals, including the z2 term.

In the discussion below, the values of z1 and z2 may be arbitrary within certain parameters and assumptions, with the assumption, for example, that, in practice, z2 may often be assumed to be small. The expressions for the integral values that include z2, i.e., CS2_z2, CC2_z2, CS1_z2, and CC1_z2, are analytically exact, and apply to any values of z1 and z2. Hence, although the need for z1 and z2 arises from the effect of the Coriolis mode component 306 in shifting the locations of zero crossings in the sensor signal 304, the resulting and described analysis is valid for any integral limits, whether or not the integral limits actually coincide with the zero crossings of the sensor signal 304. As described in detail below, this analysis offers many practical benefits, including, for example, significant reductions in the computational effort required.

Figure 7:
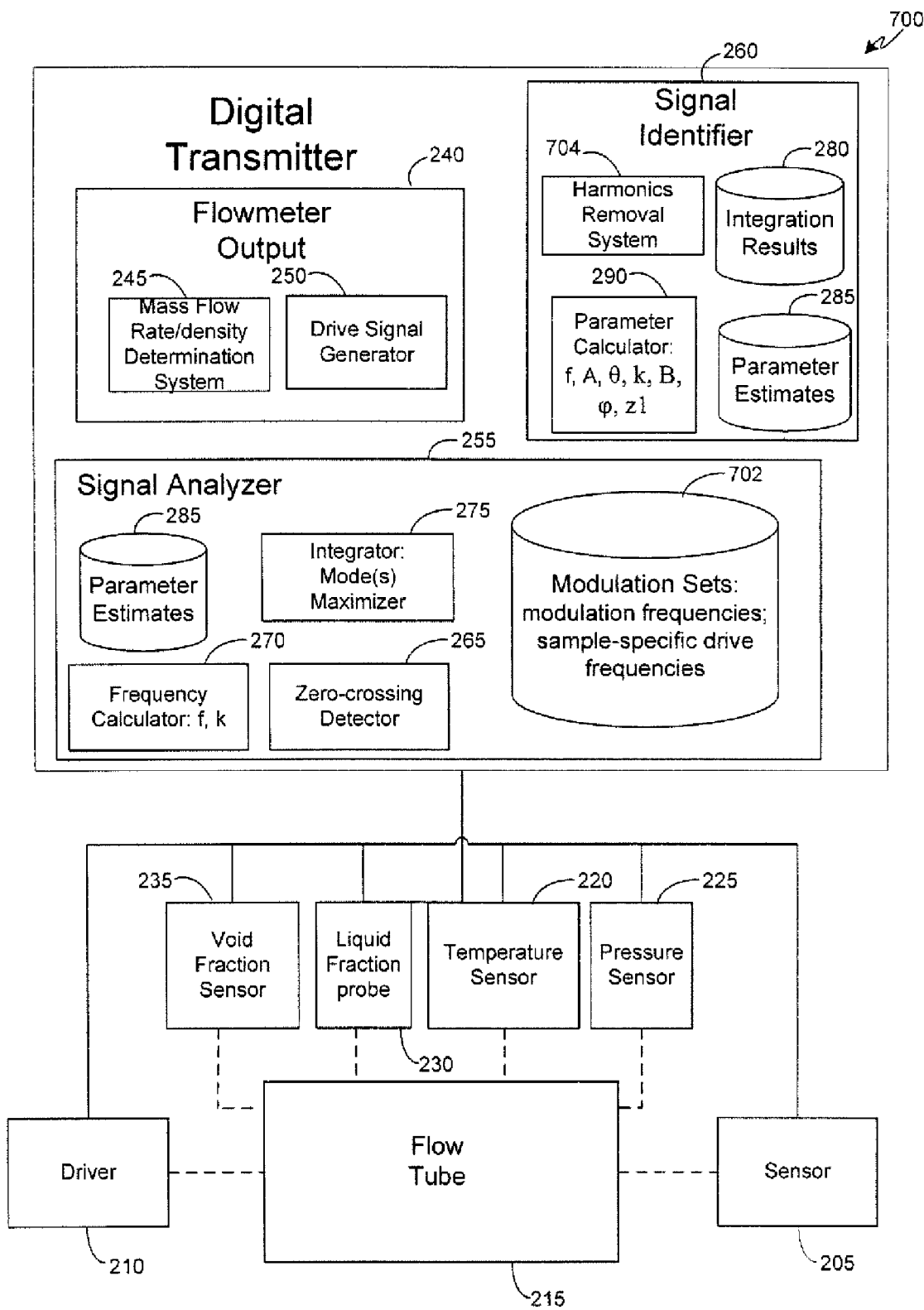
FIG. 7 is a block diagram of a second implementation of the flowmeter of FIG. 2.

FIG. 7 is a block diagram of a flow meter 700. The flow meter 700 of FIG. 7 operates similarly to the flow meter 200 of FIG. 2, but further includes an additional effect of the coriolis mode signal 306 on the sensor signal 304, mentioned above and referred to herein as offset z2.

Figure 8:
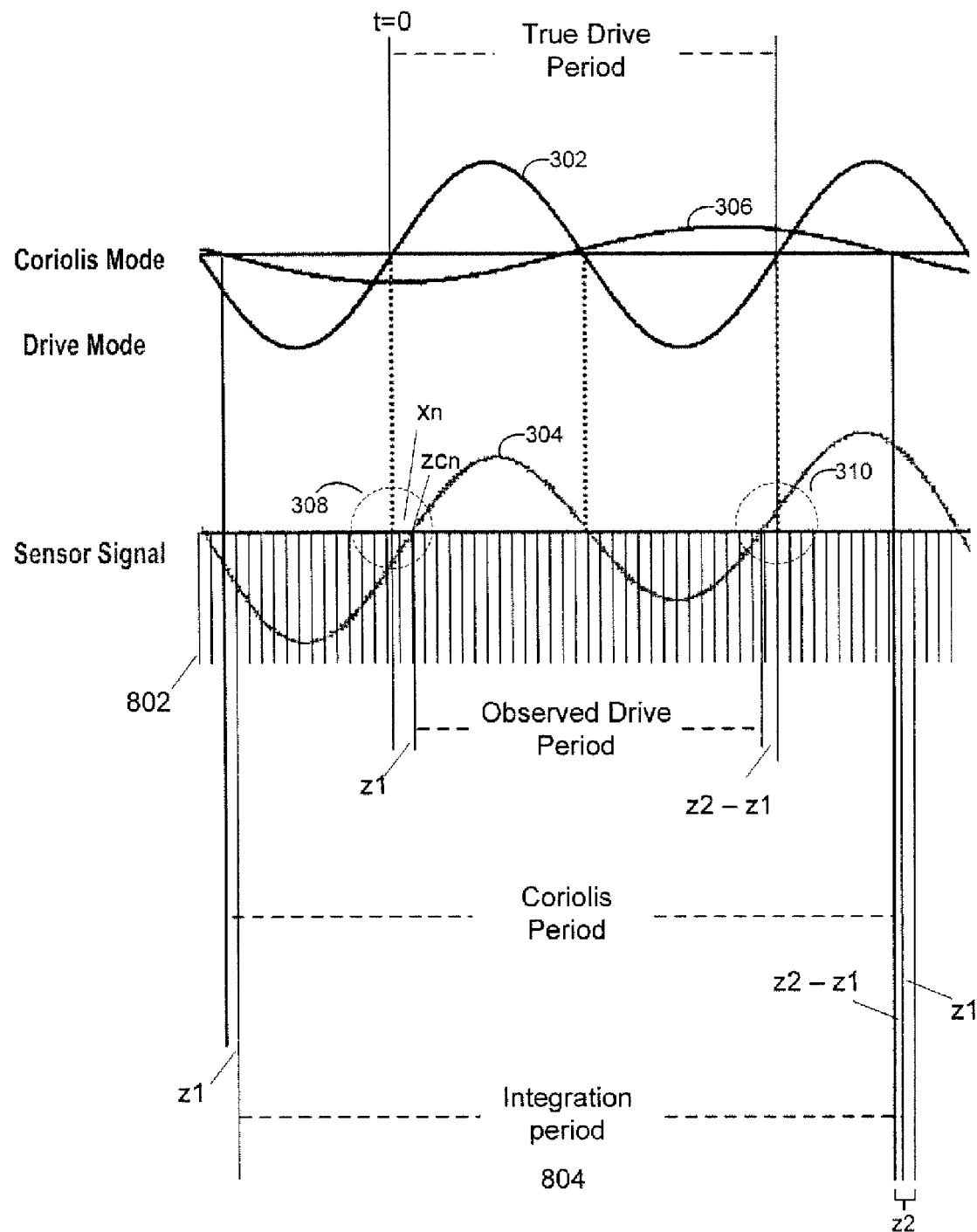
FIG. 8 is a second timing diagram of a sensor signal having a drive mode signal component and a coriolis mode signal component.

Referring to FIG. 8, the offset z2 may be seen to result from the asymmetry of the coriolis mode signal 306 relative to the drive mode signal 302, such that the offset z2 exists independently of the offset z1 defined above. As shown in FIG. 8, the offset z2 may be defined as the difference between the true drive period of the drive mode signal 302 and the actual, observed drive period of the corresponding sensor signal 304, based on zero crossings.

In the first instance, then, the value z2 may be incorporated into modified versions of Eqs. (5)-(18). That is, equations may be developed for the two pairs of integrals, i.e., the drive-emphasized integrals CS2_z2 and CC2_z2, and the coriolis-emphasized integrals CS1_z2 and CC1_z2, where the designator_z2 indicates the inclusion of both offsets z1 and z2 (although z1 is not included in this notation, for brevity's sake). The resulting equations are shown as Eqs. (19)-(30).

Thus, CS2_z2 may be written as Eq. (19):

$$CS2\_z2\_int(A, f, B, k, \phi, z1, z2) := \qquad \text{Eq. (19)}$$

$$\int_{-\left(\frac{1}{2k}-\frac{1}{2f}\right)+z1}^{\frac{1}{f}+\left(\frac{1}{2k}-\frac{1}{2f}\right)+z1+z2} [B \cdot \sin[(2 \cdot \pi \cdot k \cdot t) + \phi] + A \cdot \sin(2 \cdot \pi \cdot f \cdot t)] \cdot$$

$$\sin\left[4 \cdot \pi \cdot \frac{k}{(1+k \cdot z2)} \cdot \left[t - z1 + \left(\frac{1}{2k} - \frac{1}{2f}\right)\right]\right] dt$$

It may be observed that the z2 term occurs twice in Eq. (19). Firstly, z2 occurs in the upper limit of the integral, so that it may be seen that the integration period deviates from an ideal length of 1/k seconds (i.e., a period of the coriolis mode signal 306) by z2 seconds. Secondly, the period of the modulating sine term is also adjusted by z2 seconds. Overall, therefore, Eq. (19) the numerical integration(s) to be performed on the sensor signal 304 (which are based on the observed zero crossings) inherently include errors caused by the presence of z2 and reflected in the integration limits and modulation function(s) (frequencies), so that Eq. (19) represents the consequences of applying these 'wrong' integral limits and corresponding 'wrong' modulation frequency.

The A term is given by Eq. (20):

$$CS2\_Aonly\_z2(A, f, B, k, \phi, z1, z2) := -2 \cdot A \cdot k \cdot \qquad \text{Eq. (20)}$$

$$(1 + k \cdot z2) \cdot \frac{\sin\left[\pi \cdot f \cdot \left(\frac{1}{k} + z2\right)\right] \cdot \cos[\pi \cdot f \cdot (2 \cdot z1 + z2)]}{\pi \cdot (f + f \cdot k \cdot z2 + 2 \cdot k) \cdot (f + f \cdot k \cdot z2 - 2 \cdot k)}$$

In the case where z2=0, Eq. (20) simplifies to the corresponding expression for CS2_z1, given above in Eq. (6).

The B term is not exactly zero as above, as shown in Eq. (21):

$$CS2\_Bonly\_z2(A, f, B, k, \phi, z1, z2) := \qquad \text{Eq. (21)}$$

$$\frac{2 \cdot B \cdot (1 + k \cdot z2)}{\pi \cdot k \cdot (3 + k \cdot z2) \cdot (1 - k \cdot z2)} \cdot$$

$$\cos\left[k \cdot \pi \cdot \left(\frac{1}{f} + 2 \cdot z1 + z2\right) + \phi\right] \cdot \sin(\pi \cdot k \cdot z2)$$

However, the B term is very small, being a product of both B itself and sin(z2), both of which may be assumed to be small. In the case where z2 is zero, the B term also goes to zero.

The CC2_z2 integral may be written as in Eq. (22):

$$CC2\_z2\_int(A, f, B, k, \phi, z1, z2) := \qquad \text{Eq. (22)}$$

$$\int_{-\left(\frac{1}{2k} - \frac{1}{2f}\right) + z1}^{\frac{1}{f} + \left(\frac{1}{2k} - \frac{1}{2f}\right) + z1 + z2} [B \cdot \sin[(2 \cdot \pi \cdot k \cdot t) + \phi] + A \cdot \sin(2 \cdot \pi \cdot f \cdot t)] \cdot$$

$$\cos\left[4 \cdot \pi \cdot \frac{k}{(1 + k \cdot z2)} \cdot \left[t - z1 + \left(\frac{1}{2k} - \frac{1}{2f}\right)\right]\right] dt$$

The A term for CC2_z2 of Eq. (22) takes the form of Eq. (23):

$$CC2\_Aonly\_z2(A, f, B, k, \phi, z1, z2) := -A \cdot f \cdot \qquad \text{Eq. (23)}$$

$$(1 + k \cdot z2)^2 \cdot \frac{\sin\left[\pi \cdot f \cdot \left(\frac{1}{k} + z2\right)\right] \cdot \sin[\pi \cdot f \cdot (2 \cdot z1 + z2)]}{\pi \cdot (f + f \cdot k \cdot z2 + 2 \cdot k) \cdot (f + f \cdot k \cdot z2 - 2 \cdot k)}$$

while the B term takes the form of Eq. (24):

$$CC2\_Bonly\_z2(A, f, B, k, \phi, z1, z2) := \qquad \text{Eq. (24)}$$

$$\frac{-B \cdot (1 + k \cdot z2)^2}{\pi \cdot k \cdot (k \cdot z2 + 3) \cdot (k \cdot z2 - 1)} \cdot$$

$$\sin\left[k \cdot \pi \cdot \left(\frac{1}{f} + 2 \cdot z1 + z2\right) + \phi\right] \cdot \sin(\pi \cdot k \cdot z2)$$

As in Eq. (21), the B term of Eq. (24), being a product of the two small terms B and sin(z2), is small.

Having described the above drive-emphasized characterization, having the first pair of integrals CS2_z2 and CC2_z2, corresponding equations may be developed for the coriolis-emphasized characterization, including the second pair of integrals CS1_z2 and CC1_z2.

Specifically, CS1_z2 may be written as Eq. (25):

$$CS1\_z2\_int(A, f, B, k, \phi, z1, z2) := \qquad \text{Eq. (25)}$$

$$\int_{-\left(\frac{1}{2k} - \frac{1}{2f}\right) + z1}^{\frac{1}{f} + \left(\frac{1}{2k} - \frac{1}{2f}\right) + z1 + z2} [B \cdot \sin[(2 \cdot \pi \cdot k \cdot t) + \phi] + A \cdot \sin(2 \cdot \pi \cdot f \cdot t)] \cdot$$

$$\sin\left[2 \cdot \pi \cdot \frac{k}{(1 + k \cdot z2)} \cdot \left[t - z1 + \left(\frac{1}{2k} - \frac{1}{2f}\right)\right]\right] dt$$

Eq. (25) has an analytical expression for the A term given by Eq. (26):

$$CS1\_Aonly\_z2(A, f, B, k, \phi, z1, z2) := \qquad \text{Eq. (26)}$$

$$-A \cdot k \cdot (1 + k \cdot z2) \cdot \frac{\sin\left[\pi \cdot f \cdot \left(\frac{1}{k} + z2\right)\right] \cdot \cos[\pi \cdot f \cdot (2 \cdot z1 + z2)]}{\pi \cdot (f + f \cdot k \cdot z2 + k) \cdot (f + f \cdot k \cdot z2 - k)}$$

Eq. (25) has a B term given by Eq. (27):

$$CS1\_Bonly\_z2(A, f, B, k, \phi, z1, z2) := \frac{-B \cdot (1 + k \cdot z2)}{\pi \cdot k^2 \cdot z2 \cdot (2 + k \cdot z2)} \cdot \qquad \text{Eq. (27)}$$

$$\cos\left[\pi \cdot k \cdot \left(\frac{1}{f} + 2 \cdot z1 + z2\right) + \phi\right] \cdot \sin(\pi \cdot k \cdot z2)$$

The presence of z2 in the denominator of Eq. (27) may suggest that the B term goes to infinity as z2 tends to zero. However, the presence of the sin(π·k·z2) term in the numerator allows for re-arrangement of Eq. (27) in terms of the sinc function sin(π·k·z2)/(π·k·z2), which may be shown to tend towards CS1_Bonly_z1 of Eq. (11), as z2 tends to zero.

Finally, CC1_z2 may be written as Eq. (28):

$$CC1\_z2\_int(A, f, B, k, \phi, z1, z2) := \qquad \text{Eq. (28)}$$

$$\int_{-\left(\frac{1}{2k} - \frac{1}{2f}\right) + z1}^{\frac{1}{f} + \left(\frac{1}{2k} - \frac{1}{2f}\right) + z1 + z2} [B \cdot \sin[(2 \cdot \pi \cdot k \cdot t) + \phi] + A \cdot \sin(2 \cdot \pi \cdot f \cdot t)] \cdot$$

$$\cos\left[2 \cdot \pi \cdot \frac{k}{(1 + k \cdot z2)} \cdot \left[t - z1 + \left(\frac{1}{2k} - \frac{1}{2f}\right)\right]\right] dt$$

For Eq. (28), the A term may be written as in Eq. (29):

$$CC1\_Aonly\_z2(A, f, B, k, \phi, z1, z2) := \qquad \text{Eq. (29)}$$

$$-A \cdot f \cdot (1 + k \cdot z2)^2 \cdot \frac{\sin\left[\pi \cdot f \cdot \left(\frac{1}{k} + z2\right)\right] \cdot \sin[\pi \cdot f \cdot (2 \cdot z1 + z2)]}{\pi \cdot (f + f \cdot k \cdot z2 + k) \cdot (f + f \cdot k \cdot z2 - k)}$$

Further for Eq. (28), the B term, where again the sinc function sin(π·k·z2)/(π·k·z2) is included, may be written as in Eq. (30):

$$CC1\_Bonly\_z2(A, f, B, k, \phi, z1, z2) := \frac{-B \cdot (1 + k \cdot z2)^2}{\pi \cdot k^2 \cdot z2 \cdot (2 + k \cdot z2)} \cdot \qquad \text{Eq. (30)}$$

$$\sin\left[\pi \cdot k \cdot \left(\frac{1}{f} + 2 \cdot z1 + z2\right) + \phi\right] \cdot \sin(\pi \cdot k \cdot z2)$$

A full derivation and development of Eqs. (5)-(30) is provided below with respect to FIGS. 12-15. Here, Eqs. (19)-(30) are included to explain the operation of the signal analyzer 255 and the signal identifier 260, in the context of the implementation of the flowmeter 700 of FIG. 7.

Specifically, the integrator 275 outputs integration results CS2_z2 and CC2_z2 within the drive-emphasized characterization of the sensor signal 304, taking into account both the offset z1 and the offset z2 over a period that is close to, but not necessarily equal to, period of the coriolis mode signal 306. Similarly, the integrator 275 also outputs integration results CS1_z2 and CC1_z2, representing the coriolis-enhanced characterization of the sensor signal 304, and also taking into effect the offsets z1, and z2 over the same integration interval.

As described above, and as may be seen in Eqs. (19)-(30), the CS2_z2 and CC2_z2 integration results use a modulation function having a frequency that is approximately twice that of the coriolis mode signal 306, while the integration results CS1_z2 and CC1_z2 use a modulation function having a frequency approximately equal to the coriolis mode frequency. Generally speaking, then, the flowmeter 700 may proceed with corresponding calculations described above with respect to FIGS. 4-6, but using the integration results CS2_z2, CC2_z2, CS1_z2 and CC1_z2. Further illustration and examples of such calculations are provided below, with respect to FIGS. 9-11.

Additionally, these calculations may be further modified for computational convenience and improved accuracy. Specifically, in FIG. 8, samples 802 are illustrated to illustrate a sampling of the sensor signal 304 that may be performed by an analog-to-digital conversion (ADC) implemented in association with operation of the digital transmitter 104 of the flow meter 700. Although not drawn to scale, FIG. 8 illustrates that the samples 802 will not necessarily coincide directly with any of the zero crossings of the sensor signal 304, or zero crossings of the drive mode signal 302, or of the coriolis signal 306. As in virtually any digital system that relies on conversion to and/or from analog signals, some loss of accuracy may result from such sampling errors. For example, the signal analyzer 255 may use integral limits between a first sampled value of the sensor signal 304 and a second sampled value, rather than integrating between true zero-crossing values.

A shift in the starting point of the integral to the exact time of an ADC sample implies a corresponding shift in the (initially unknown) value of z1. However, as sampling on each of a plurality of sensor signals (i.e., from different sensors 205) is simultaneous, the same shift applied during the processing of each sensor signal will apply the same shift to the respective values of z1, hence leaving the resulting phase difference calculation(s) unaffected.

Similarly, shifting the end-point of the integral to the exact time of an ADC sample will adjust the integration period from its ideal value of the Coriolis mode period, and will, in other words, adjust the value of z2. However, given the analytical results in Eqs. (19)-(30), it is possible to compensate the integral values for a non-zero value of z2. It is thus possible to integrate over whole samples, with little or no loss of accuracy.

More specifically, in order to address such sampling errors and issues, in FIGS. 7 and 8, the values z2 may be modified or chosen such that integral limits each coincide directly with one of the samples 802. In other words, as shown in FIG. 8, an adjusted integration period may be effectively selected, such that the value z2 is defined as a difference between the actual integration period used by the integrator 275 and a period of the coriolis mode signal 306.

This modification of z2 results in computational convenience and reduced processing requirements, and may be obtained by a corresponding adjustment of the value z1, without effecting a calculation of the drive amplitude A. It should be understood that such an adjustment of the value z1 will not substantially affect determination of phase difference required by the flowmeter output unit 240, since determination of the mass flow rate relies on a relative difference between the phases of two separate sensor signals, i.e., a difference between two values of z1.

As a result of this ability to compensate for the value of z2, the modulation functions of the integrals described above may be adjusted such that the integral limits and modulation frequencies of the CS2_z2, CC2_z2, CS1_z2, and CC1_z2 integrals correspond to an exact number of samples, as shown by the integration period 804 of FIG. 8. Such an adjustment results in a simplification of an integration calculation, as well as an improvement in accuracy of these calculations. Further, the modulation frequencies may be stored and reused.

Existing techniques allow for integration over periods that do not start and end on exact sample boundaries, but include various errors and calculations that are included for the purpose of dealing with such integrations. These errors and calculations may be eliminated through the use of z1 and z2, as described herein.

Furthermore, a significant computational effort associated with the type of Fourier integrations described herein and in the prior art is the calculation of the modulation sine and cosine functions. If the exact (or best estimate of) the instantaneous drive or Coriolis frequency is used for these integrations, then the modulation functions may need to be recalculated each time. If, however, through the use of z1 and z2, the integration time is restricted to convenient whole-sample periods, then it is possible to "cache" modulation sine and cosine values, so that recalculation thereof occurs only when there is a shift in the drive frequency f that is determined to be sufficiently large to warrant such a recalculation.

Accordingly, the signal analyzer 255 includes modulation sets 702 which store modulation frequencies and sample-specific drive frequencies. For example, if a true frequency vibration of the flow tube 215 is equal to 82.51 hertz, then this frequency may correspond to, for example, 121.197 samples at a sample rate of 10 kHz. Therefore, modulation sets corresponding to 121 samples and 122 samples may be calculated, for use by the integrator 275 in determining the integration results CS2_z2, CC2_z2, CS1_z2, and CC1_z2. The modulation sets 702 in this example may thus continue to be used by the integrator 275 until the drive period moves below 121 or above 122 samples, at which time other modulation set(s) may be used.

For example, in one implementation, z2 may be set so as to vary by ±0.5 of a sample period, since, for example, whenever z2 would move beyond this value, the next drive frequency (modulation set) may begin to be used. For example, the flowmeter 700 may be measuring parameters of a fluid in the flowtube 215, and a density of the fluid (or some other parameter) may change such that a coriolis frequency k (and corresponding period) changes from corresponding to 121.2 samples to corresponding to 121.7 samples, over some window of time. During that window of time, z2 will thus change incrementally on, for example, a cycle-by-cycle basis, while the modulation set with exactly 121 samples will be used for integration calculations, so that z2 gets bigger until the true period of 121.5 is reached. At that time, z2 will be approximately equal to half of the sample period, in seconds, and a new modulation set corresponding to 122 samples will begin to be used. Then, the value of z2 will jump to −0.5*the sample period in seconds, and will increase towards zero until the true period of 121.7 samples is reached, at which point z2 equals −0.3 sample periods.

In this way, z2 may be viewed as varying, on a cycle-by-cycle basis, to accommodate small changes in the drive frequency f, so as to avoid otherwise-necessary recalculations of modulation function values that would be caused by these frequency changes. Thus, z2 may be viewed as representing the time difference between the best estimate of the exact period of the coriolis mode component 306, and the integration period 804 that is used for integration (e.g., 121 or 122 samples), as shown in FIG. 8.

Figure 9:
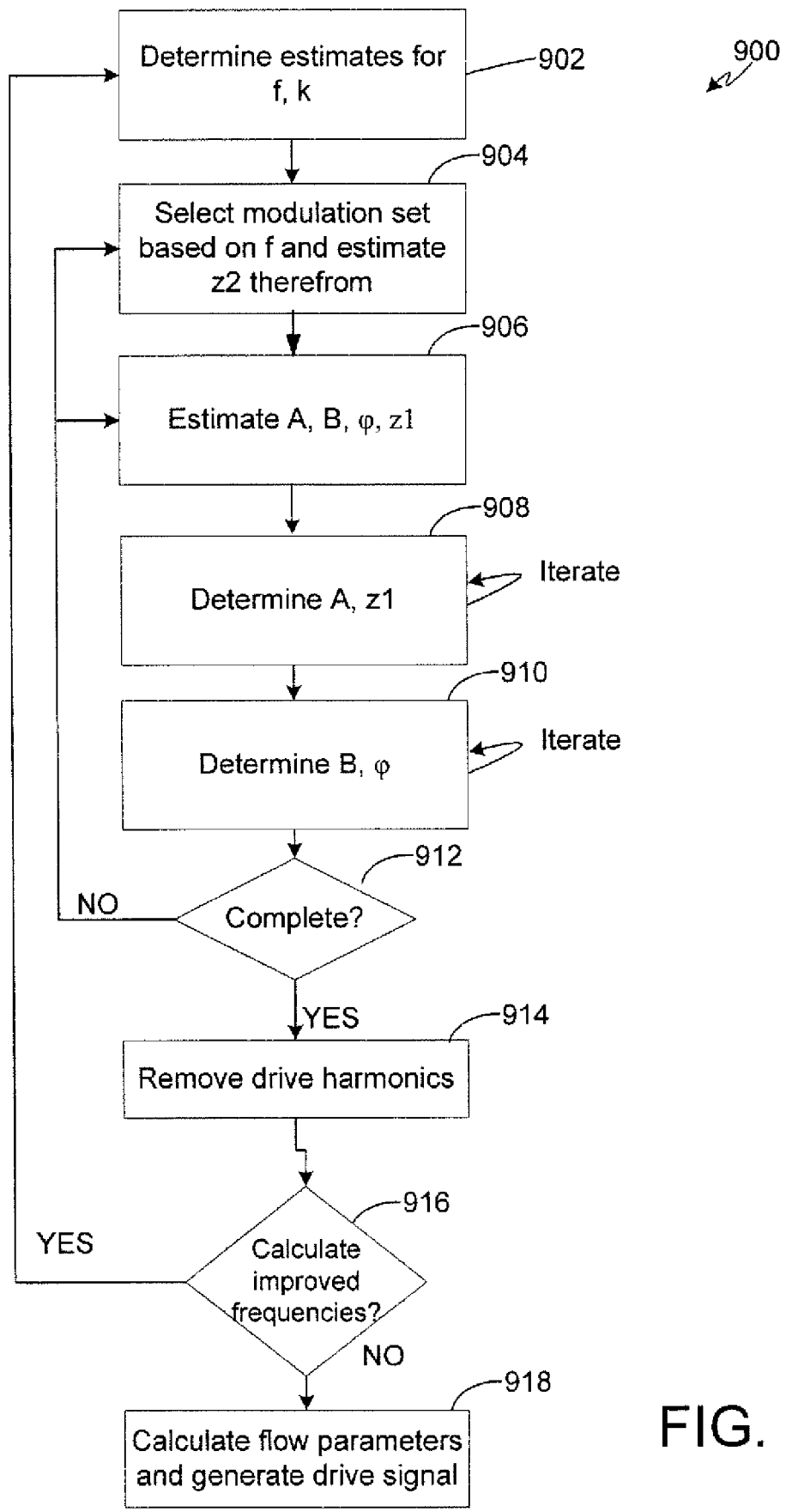
FIG. 9 is a flow chart illustrating an first operation of the flow meter of FIG. 7.

FIG. 9 is a flow chart 900 illustrating an operation of the flow meter 700. The basic strategy of the technique of FIG. 9, including z2, is the same as that described above with respect to FIGS. 4-6, with the following additional considerations. Specifically, as already described, and as shown in more detail below with respect to FIGS. 12-15, the analytical expressions (Eq. (20)/(21), (23)/(24), (26)/(27), and (29)/(30)) for each of the four integrals including z2, i.e., CS2_z2, CC2_z2, CS1_z2, and CC1_z2 (Eqs. (19), (22), (25), and (28), respectively) simplify to the corresponding analytical expressions (Eq. (6), (8), (10)/(11), and (13)/(14)) for the z1 integrals, i.e., CS2_z1, CC2_z1, CS1_z1, and CC1_z1 (Eq. (5), (7), (9), and (12), respectively), when z2 equals zero.

Thus, a z2_error term may be defined for each of the z2 integrals, and, specifically, may be defined as a difference between each pair of corresponding z1 and z2 analytical expressions (e.g., CS2_z2_err=CS2_z2−CS2_z1; CC2_z2_err=CC2_z2−CC2_z1, CS1_z2_err=CS1_z2−CS1_z1; and CC1_z2_err=CC1_z2−CC1_z1). The z2 error terms may be estimated analytically using the best estimates of each of the parameter values f, k, A, z1, B, φ, and z2. The value of the z2_error term may then be subtracted from the numerical value of the z2 integral calculated by the integrator 275, to give an estimate of what the z1 integral value would be, (i.e., if z2=0).

With the resulting estimates of the z1 integral values, improved estimates of A, z1, B, φ may be calculated as described above, which in turn lead to improved estimates of f, k, and hence z2. These improved parameter estimates can be used to provide better values for the z2_error terms, and, hence, the system of equations may be iterated to convergence. As long as z2 has a sufficiently small value (e.g., less than half a sample period), the influence of B on the CS2_z2 and CC2_z2 remains very small. Thus, good first estimates of the parameters A and z1 may be achieved by assuming z2=z2_error=0.

Having described techniques for using z2 in general terms, FIG. 9 illustrates more specific and detailed examples of these techniques. In FIG. 9, the process begins with determination of values for the drive signal frequency f and the coriolis mode frequency k, as determined by the zero crossing detector 265, the frequency calculator 270, and the modulation sets 702 (902). These values may be determined in conjunction with, and/or based on, a selection of an appropriate value for z2, i.e., a value that results in sample-specific integration limits. As noted, this setting of a z2 value may result in an adjustment to a value of z1, that will be reflected in the following calculations and results, but that does not impact actual outputs of the flowmeter 700 (e.g., mass flow rate, density, and/or new drive signal parameters), assuming the same integration interval is used for the relevant sensor sets.

Using the frequency values and modulation set values, the integrator 275 may thus determine appropriate integral values (904), i.e., CS2_z2_val, CC2_z2_val, CS1_z2_val, and CC1_z2_val. The signal identifier 260 may then determine initial estimates of the parameters A, z1, B, and φ, as described above (906).

Then, the parameter calculator 290 may determine improved values for A and z1, using equations that are analogous to Eqs. (3) and (4) (and Eqs. (15) and (16)), above (908), that is, for example, using Eqs. (31) and (32), respectively:

Based on the current best estimates of z1, z2, f, k, A, B, and φ, estimates of the z2 error terms are calculated based on the analytical expressions given above:

$$CS2\_z2\_err = CS2\_z2 - CS2\_z1$$

$$CC2\_z2\_err = CC2\_z2 - CC2\_z1$$

$$CS1\_z2\_err = CS1\_z2 - CS1\_z1$$

$$CC1\_z2\_err = CC1\_z2 - CC1\_z1$$

These error terms are best estimates of the small adjustments needed to the numerical values of the integral values to compensate for non-zero values of z2. Accordingly, estimated values of the z1 integral values are calculated by subtracting the z2 error values from the numerical values of the integrals generated by the integrator 275.

$$CS2\_z1\_est = CS2\_z2\_val - CS2\_z2\_err$$

$$CC2\_z1\_est = CC2\_z2\_val - CC2\_z2\_err$$

$$CS1\_z1\_est = CS1\_z2\_val - CS1\_z2\_err$$

$$CC1\_z1\_est = CC1\_z2\_val - CC1\_z2\_err$$

Based on these estimated numerical values of the z1 integrals, improved estimates of A and z1 are calculated using similar equations to $$A\_est\_CS2\_z2(CS2\_z1\_est, CC2\_z1\_est, f, k) = \sqrt{\left(\frac{CC2\_z1\_est}{f}\right)^2 + \left(\frac{CS2\_z1\_est}{2k}\right)^2} \cdot \left[\frac{\pi \cdot (f^2 - 4k^2)}{\sin\left(\frac{f}{k} \cdot \pi\right)}\right] \quad \text{Eq. (31)}$$

$$z1\_est(CS2\_z1\_est, CC2\_z1\_est, f, k) = \frac{\operatorname{atan}\left(\frac{2k \cdot CC2\_z1\_est}{f \cdot CS2\_z1\_est}\right)}{2 \cdot \pi \cdot f} \quad \text{Eq. (32)}$$

At this point, further iterations may be made to account for errors within the calculations that are due to the presence of z2. Such phase iterations are discussed in more detail below, with respect to FIG. 10.

Subsequently, the parameter calculator 290 may determine values for B and φ, using equations that are analogous to Eqs. (3) and (4) (and Eqs. (17) and (18)), above (910), that is, for example, using Eqs. (33) and (34), respectively:

$$c = CC1\_z1\_est - CC1\_Aonly\_z1(A,f,0,k,0,z1)$$

$$s = CS1\_z1\_est - CS1\_Aonly\_z1(A,f,0,k,0,z1)$$

$$B\_est\_CS1\_z2 = 2k \cdot \sqrt{c^2 + s^2} \quad \text{Eq. (33)}$$

$$\phi\_est\_CS1\_z2 = \operatorname{atan}\left(\frac{c}{s}\right) - k \cdot \pi \cdot \left(\frac{1}{f} + 2 \cdot z1\right) \quad \text{Eq. (34)}$$

As with the determination of A and z1, additional iterations may be performed to account for errors introduced by the z2 offset. Such iterations are discussed in more detail with respect to FIG. 11.

If the values for A, z1, B, and φ are not sufficiently accurate (912), then the process may iterate through the determinations of those values, using the just-determined values (906). Otherwise, the process may re-calculate the original integral values CS2_z2, CC2_z2, CS1_z2, and CC1_z2 (904).

Otherwise (912), the process may perform additional processing to determine harmonics of the drive signal present within the sensor signal 304 (914). For example, referring to FIG. 7, a harmonics removal system 704 is illustrated that is designed to remove, or account for the effects of, harmonics of the drive mode signal 302. That is, as mentioned above, various factors may lead to the presence of harmonics or multiples of the drive frequency within the sensor signal 304. In conventional processing, such as the Fourier analysis of Eqs. (1)-(4), such harmonics do not generally impact the analysis, because the integrations are performed over the drive cycle itself, and, since the harmonics of the drive mode signal 302 will have the same zero-crossings as the drive mode signal 302 itself, the harmonics do not impact the calculations of A and θ.

In contrast, the calculations of Eqs. (5)-(34) include integrations performed over a period of the coriolis signal 306, which will not generally have the same zero-crossings as the drive mode signal 302, as explained above. As a result, the drive harmonics may be considered as part of a separate or additional processing.

One technique for accounting for these drive harmonics is to include a simple low pass filter as the drive harmonics removal system 704. In this case, the filter may be implemented within the digital transmitter 104, or outside of the digital transmitter 104, e.g., in the sensor 205. Such a filter may be operable to remove some or all of the drive harmonics that are above the coriolis mode signal 306.

Additionally, or alternatively, an analysis of the sensor signal 304 may be performed at the harmonics removal system 704 in which estimates of the parameters of the drive harmonics are obtained, perhaps from periodic integrations over a period of the drive signal. Then, by making certain assumptions about the relationships of the parameters to one another, effects of the drive signal harmonics may be removed from the analysis of the sensor signal by the signal analyzer 255.

In other words, considering drive harmonics, the sensor signal 304 may be expressed in the form of $S(t)=A \sin(2\pi ft+\psi)+B \sin(2\pi k+\phi)$ (for the sine terms), so that the second harmonic may be written as $A_2 \sin(2\pi ft+\psi_2)+B_2 \sin(2\pi k+\phi_2)$, and the third harmonic may be written in the form $A_3 \sin(2\pi ft+\psi_3)+B_3 \sin(2\pi k+\phi_3)$, and so on. In this formulation, it may be assumed that the signal parameters have certain relationships to one another that may be known or determined. For example, it may be assumed that a ratio of $A_2/A$ is known, as well as $A_3/A_2$, or that a relationship between $\psi$ and $\psi_2$ is known. Accordingly, additional corrections can be made to the numerical values of the integrals CS2 etc based on estimates of the influence of the higher harmonics.

Therefore, for example, once a value for A is known from the above calculations, the value of $A_2$ may be determined, and thereafter the value of $A_3$. Similar comments apply to the phase information $\psi$ of the various harmonics. In other words, the above coriolis-based integrations may be performed to determine estimates of A, z1, B, and φ compensating for the estimated influence of the higher harmonics of the drive frequency. Then, periodically, the integrator 275 may perform integrations over the drive cycle, rather than the coriolis cycle, in order to update, for example, information regarding the relationships between the harmonics.

Of course, combinations of the above techniques may be implemented. For example, a filter may be used to remove harmonics having value $A_3$ and above, so that the above analysis need only be performed for the second harmonic. Determination of how many harmonics to be filtered may be made based on, for example, a relationship between the frequencies f and k, or based on a desired dynamic response of the particular flowmeter (which may be impacted by such filtering).

Further, it may be possible to calculate improved frequencies f and k (916). If so, then, the improved frequency values may be used in a further iteration of the entire process 900.

Examples of such techniques generally contemplate the use of the exact phase observed over each integration period of the calculation(s), and to note the shift in phase over adjacent ones of the integrations periods. Then, the calculated frequency is given by the time taken to generate a phase shift of $2\pi$ radians.

For example, it should be understood that the offset value z1 essentially provided information regarding true zero crossings of the drive signal (as shown, for example, in FIGS. 3 and 8). That is, a parameter $X_n$ may be defined as a phase offset in degrees between a zero-crossing of the drive mode signal 302 (e.g., at time t=0) and an actual zero-crossing $zc_n$ of the sensor signal 304 (illustrated in FIG. 8). Then, considering only say zero crossings from negative to positive sensor signal values consecutive phases $X_n$, $X_{n+1}$, $X_{n+2}$, and zero crossing locations $zc_n$, $zc_{n+1}$, and $zc_{n+2}$ may be identified.

In this formulation, it may be seen that $(zc_{n+1}-zc_n)$ is the obvious estimate of the drive period. However, at each of these positions we have observed phase offsets from the zero crossing of the drive component of $X_{n+1}-X_n$. If $(zc_{n+1}-zc_n)$ were exactly equal to the true drive period, then it would be found that $(X_{n+1}-X_n)=0$ (even if neither $X_{n+1}$ nor $X_n$ are zero themselves. Hence the difference $X_{n+1}-X_n$ can be used to improve the estimate of frequency.

One approach is to calculate the true instant of zero crossing for the drive phase component by adjusting for the observed phase offset. The true instant of zero phase for associated with cycle n, $tz_n$ may be expressed in Eq. (36):

$$tz_n = zc_n - (X_n/360)f_{est} \qquad \text{Eq. (36)}$$

while Eq. (37) defines the equivalent instant of zero phase for the next cycle, n+1.

$$tz_{n+1} = zc_{n+1} - (X_{n+1}/360)f_{est} \qquad \text{Eq. (37)}$$

Then, finally, a corrected period (and thereby a revised frequency) may be obtained as a difference of these zero values, i.e., $(1/f_{revised}) = tz_{n+1} - tz_n$.

It should be understood that FIG. 9 is intended to show examples of general flows of the process 900, but that the above-described operations are not restricted to the outline or order of the process 900. For example, the just-described frequency updating procedure may be performed cycle-by-cycle, intra-cycle, or merely periodically.

A revised frequency k may be determined from the revised value of f. Alternatively, a similar procedure to that just described may be performed for k, using the determined value(s) for the parameter φ. For example, if φ is calculated once per cycle, then consecutive values of φ may be compared to calculate k in the above-described manner.

Determining k from f as described above relies on a particular relationship between these two parameters, and, to the extent that this relationship is not exact, the value of k may generally be less accurate in the first instance than a value of f. As a result, cycle-by-cycle estimates of the coriolis frequency k may be relatively noisy. Nonetheless, averaged values of k over a given time period (e.g., one minute) will give a relatively stable estimate of the coriolis frequency k.

Additionally, in some implementations, a ratio of f to k may be determined based on the improved estimates of each parameter. Then, sudden changes in the drive frequency (resulting, e.g., from changes in fluid density in the flowtube 215, instigation of two-phase flow, or other abrupt changes) will result in corresponding and proportional changes in the coriolis mode.

If improved frequencies are not calculated (916), then the flowmeter output unit 240 may proceed with the calculation of flow parameters (e.g., mass flow rate and/or density), as well as with the outputting of appropriate parameters for generating the next drive signal (918).

Figure 10:
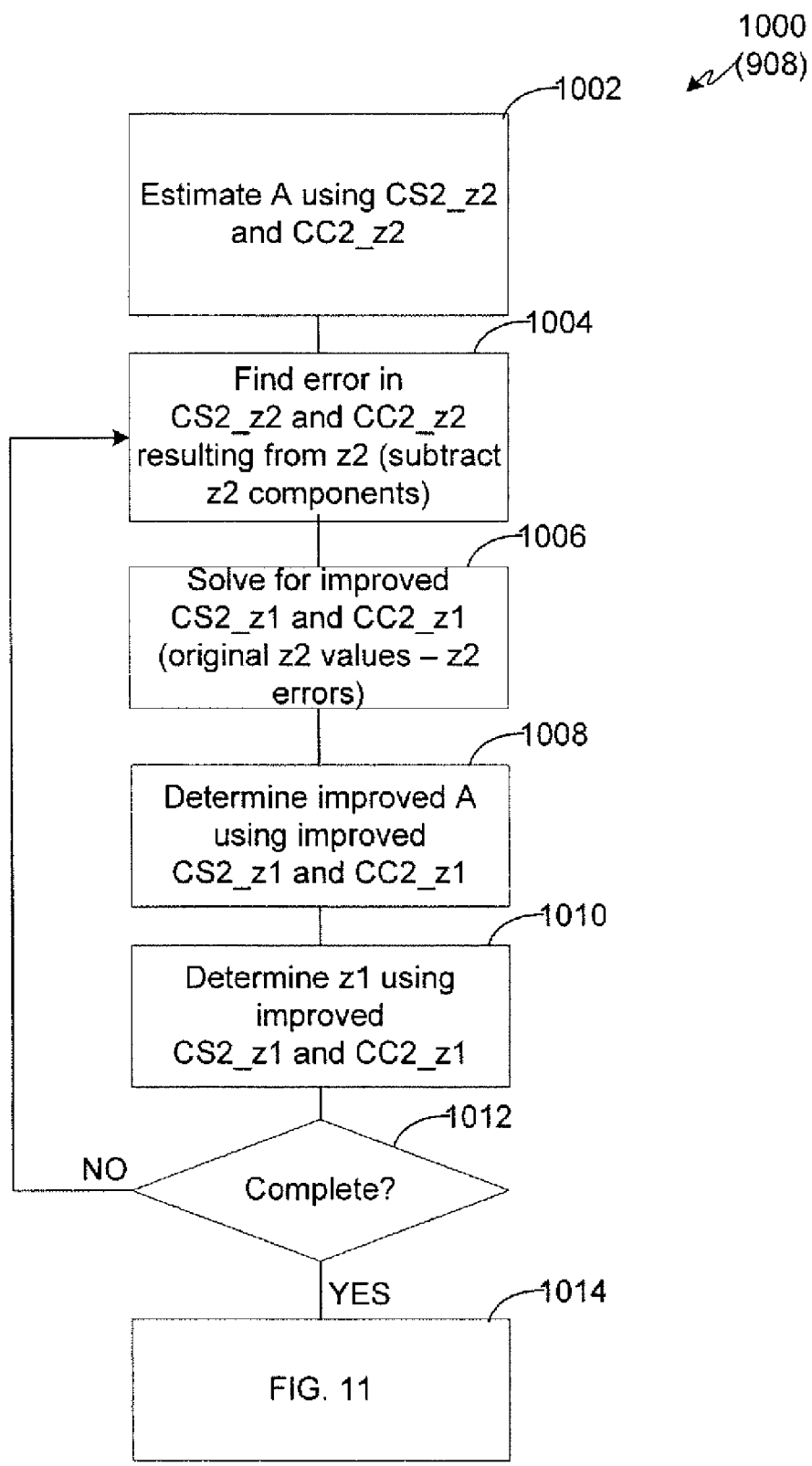
FIG. 10 is a flow chart illustrating a second operation of the flow meter of FIG. 7.

FIG. 10 is a flowchart 1000 illustrating an example of a first operation of FIG. 9. Specifically, FIG. 10 illustrates the techniques discussed above for FIG. 9 in which the values A and z1 are calculated, including iterations for phase offsets introduced by the presence of the value z2 (908).

Figure 11:
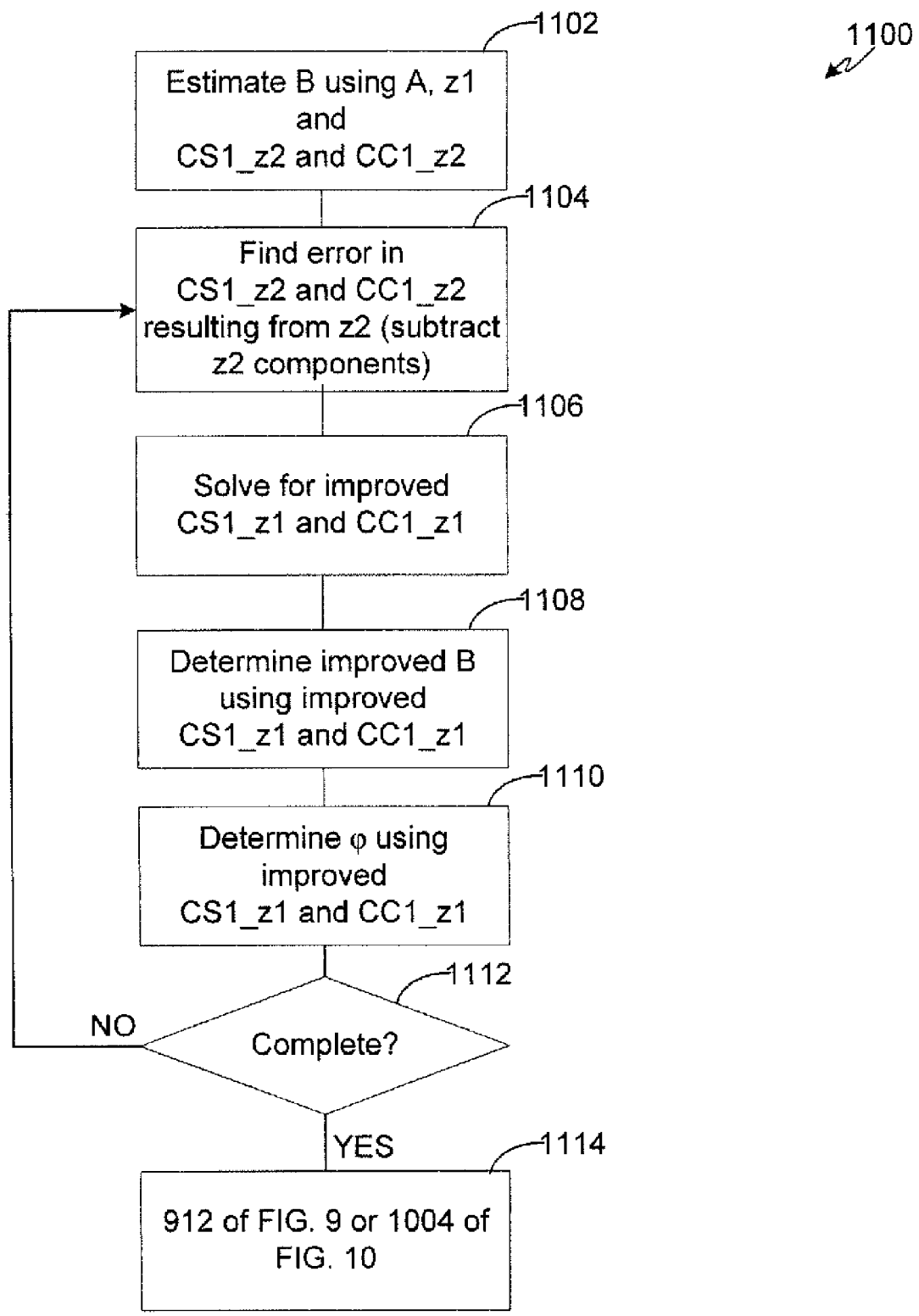
FIG. 11 is a flow chart illustrating a third operation of the flow meter of FIG. 7.

Similarly, FIG. 11 is a flowchart 1100 illustrating an example of a second operation of FIG. 9. Specifically, FIG. 11 illustrates the techniques discussed above for FIG. 9 in which the values B and ϕ are calculated, including iterations for phase offsets introduced by the presence of the value z2 (910).

In FIGS. 10 and 11, numerical examples are provided for illustration. These examples assume the same true values for the parameters f, k, A, z1, B, and ϕ, above. However, as should be understood from the above description of FIG. 9, the integrals calculated by the integrator 275 reflect the presence of the value z2. In the following examples, it is assumed that the value of z2 is chosen, as described above, so as to define the relevant integration limits as falling exactly on sampling points of the sensor signal 304. In this example the value of z2=1×10$^{-5}$ s.

Referring first to FIG. 10, then, the process 1000 begins with a determination of the value A, using the numerically calculated integral values for CS2_z2 and CC2_z2, in which the drive parameters are maximized relative to the coriolis parameters, i.e., using Eqs. (19)-(30), above. In this example, these values turn out to be CS2_z2=−2.46414954242338×10$^{-3}$ and CC2_z2=−1.07153028732249×10$^{-10}$. Using Eq. (31), above (and initially assuming B is zero), the value for A may be determined to be 0.299628865383374 (1002).

Next, an error due to the presence of z2 is calculated and removed (1004). Specifically, for example, the term CS2_z2_err is recalculated using the just-obtained value for A, and this value is subtracted from the value CS2_z2=−2.46414954242338×10$^{-3}$ (1006). The remainder is thus an estimate of CS2_z1=−2.46720949500005×10$^{-3}$. Analogous calculations may be performed for CC2_z2, recalculating CC2_z2 with the obtained value of A (1004), or CC2_z2_err=6.6920402455379×10$^{-6}$, which, subtracted from the original value of CC2_z2, provides an estimate for CC2_z1=−6.69214739856663×10$^{-6}$ (1004, 1006).

Then, using these values for CS2_z1 and CC2_z1, an improved value for A may be determined using Eq. (31) (1008), which, in this example, is A=3.00002412526826×10$^{-1}$. Subsequently, using Eq. (32), the values for CS2_z1 and CC2_z1 also may be used to obtain an estimate of z1 (1010), or z1=4.98479784037622×10$^{-6}$. Techniques for modifying this approach of obtaining z1 for cases where calculations are performed twice per cycle are described above, and may be used here, as well.

If the values of A and z1 are sufficiently accurate (1012), then the process 1000 may proceed to analogous calculations for the coriolis mode signal 306, i.e., may proceed to FIG. 11 (1014). Otherwise, the process 1000 may use the newly-obtained values for A and z1 to find yet-further improved values for CS2_z1 and CC2_z1 (1004, 1006). Then, improved values for A and z1 may be obtained, which, in this case, turn out to be A=0.299999935356127 and z1=5.00009360798378×10$^{-6}$.

In FIG. 11, analogous operations may be performed for the coriolis-emphasized characterizations (integrals) CS1_z2 and CC1_z2. That is, the previously-determined information of A and z1, along with values from numerical integrations of the integrator 275 of CS1_z2=6.20062871680545×10$^{-4}$ and CC1_z2=−2.78579266493641×10$^{-7}$, may be used to determine an estimate for B (1102), using Eq. (33). In some cases, since B is relatively small, an initial estimate may be considered to be zero.

Then, an error due to the presence of z2 is calculated and removed (1104). Specifically, the term CS1_z2 is recalculated using the just-obtained value for B, and this value of (here) 2.44579936376226×10$^{-6}$ is subtracted from the value CS1_z2=6.20062871680545×10$^{-4}$ (1106). The remainder is thus an estimate of CS1_z1=6.17617072316783×10$^{-4}$.

Analogous calculations may be performed for CC1_z2, calculating the error in CC1_z2 due to z2 using the obtained value of B (1104), giving CC1_z2_err=−3.35625027516248×10$^{-6}$, which, subtracted from the original value of CC1_z2, provides an estimate for CC1_z1=3.07767100866884×10$^{-6}$ (1104, 1106).

Then, using these values for CS1_z1 and CC1_z1, an improved value for B may be determined using Eq. (33) (1108), which, in this example, is B=9.99820189036286×10$^{-5}$. Further, using Eq. (34), the values for CS1_z1 and CC1_z1 also may be used to obtain an estimate of ϕ (1010), or ϕ=9.98342808946008×10$^{-1}$ (1110).

If the values of B and ϕ are not sufficiently accurate (1112), then the process 1100 may iterate (1104). Such an iteration, in the present example, would result in further improved values of B=1.00017250689519×10$^{-4}$, and ϕ=9.9997870785885×10$^{-1}$.

Otherwise (1112), the process 1100 may return to FIG. 9 (912) (1114). That is, all calculations may be refined in light of the just-determined values for A, z1, B, and ϕ, so that the processes 900, 1000, and 1100 are repeated. Alternatively, or additionally, the process 1100 may return directly to FIG. 10 (1004), and re-calculate the parameters of that process. Such iterations may be performed until a desired level of accuracy is reached, or may be truncated based on some other criteria, such as a time and/or computing resource limitation.

The descriptions of FIGS. 2-11, above, provide explanation and examples for implementation and uses of the flowmeters 200 and 700, and other variations thereof. The description provided below in conjunction with FIGS. 12-15 provides derivation, proof, and further explanation of the techniques implemented above for FIGS. 2-11, as well as alternative techniques.

As noted above, Eqs. (1)-(4) provide the basis for a Fourier analysis of the sensor signal 304, integrating over the drive signal period, and ignoring the impact of the coriolis mode. In order to initially include an impact of the coriolis mode, a first approximation of the effect of the coriolis mode on the Fourier calculation may be made such that it is assumed that the correct integral limits and modulation frequency are used, and the only influence of the coriolis mode is the contamination of the drive integral of Eqs. 1 and 2. The sine integral of Eq. 1 is thus defined as shown in Eq. (38) (assuming no phase offset on the drive frequency):

$$S1\_int(A, f, B, k, \phi) := \qquad \text{Eq. (38)}$$

$$\int_0^{\frac{1}{f}} [B \cdot \sin[(2 \cdot \pi \cdot k \cdot t) + \phi] + A \cdot \sin(2 \cdot \pi \cdot f \cdot t)] \cdot \sin(2 \cdot \pi \cdot f \cdot t) \, dt$$

The drive mode or A term is simply A/2f, and the modulation function remains sin(2πft). The analytical expression for the influence of the B term (coriolis mode) is given by Eq. (39):

$$S1\_Bonly(A, f, B, k, \phi) := -B \cdot \qquad \text{Eq. (39)}$$

$$f \cdot \sin\left(\frac{1}{f} \cdot \pi \cdot k\right) \cdot \frac{\cos\left(\frac{1}{f} \cdot \pi \cdot k + \phi\right)}{\pi \cdot (f^2 - k^2)}$$

Similarly, the cosine integral of Eq. 2 is shown in Eq. (40)

$$C1\_int(A, f, B, k, \phi) := \qquad \text{Eq. (40)}$$

$$\int_0^{\frac{1}{f}} \begin{bmatrix} B \cdot \sin[(2 \cdot \pi \cdot k \cdot t) + \phi] + \\ A \cdot \sin(2 \cdot \pi \cdot f \cdot t) \end{bmatrix} \cdot \cos(2 \cdot \pi \cdot f \cdot t) dt$$

with modulation function cos(2πft). Here the A term is exactly zero, while the B term is given by Eq. (41):

$$C1(A1, f, B, k, \phi) := \qquad \text{Eq. (41)}$$

$$\frac{-B \cdot k}{\pi \cdot (f^2 - k^2)} \cdot \sin\left(\frac{1}{f} \cdot \pi \cdot k\right) \cdot \sin\left(\frac{1}{f} \cdot \pi \cdot k + \phi\right)$$

For both integrals, the effect of the B term modulates with φ, resulting in a coriolis mode beating effect that may be observed in both amplitude and phase (see, e.g., FIGS. 19A-19D).

As described, the coriolis mode shifts the positions of the zero crossings of the sensor signal 304, so that the zero-crossings no longer occur at the exact points of zero (or π) phase for the drive frequency, as shown in FIGS. 3 and 8. This effect is reflected in the z1 parameter, reflecting this shift from the point of zero phase on the drive signal. In this case the sine integral of the Fourier analysis may be shown as in Eq. (42):

$$S1\_z1\_int(A, f, B, k, \phi, z1) := \qquad \text{Eq. (42)}$$

$$\int_{z1}^{\frac{1}{f}+z1} \begin{bmatrix} B \cdot \sin[(2 \cdot \pi \cdot k \cdot t) + \phi] + \\ A \cdot \sin(2 \cdot \pi \cdot f \cdot t) \end{bmatrix} \cdot \sin[2 \cdot \pi \cdot f \cdot (t - z1)] dt$$

In Eq. (42), the modified modulating sine function sin [2πf(t−z1)] is zero at the start and end of the integral while the A term is slightly offset. As a consequence the A term contribution to the integral may be shown as in Eq. (43):

$$S1\_Aonly\_z1(A, f, B, k, \phi, z1) := \frac{A}{2f} \cdot \cos(2f \cdot \pi \cdot z1) \qquad \text{Eq. (43)}$$

while the B term is shown as in Eq. (44):

$$S1\_Bonly\_z1(A, f, B, k, \phi, z1) := \qquad \text{Eq. (44)}$$

$$\frac{-B \cdot f}{\pi \cdot (f^2 - k^2)} \cdot \sin\left(\frac{1}{f} \cdot \pi \cdot k\right) \cdot \cos\left(\frac{1}{f} \cdot \pi \cdot k + \phi + 2 \cdot \pi \cdot k \cdot z1\right)$$

Similarly, the cosine integral may be shown as in Eq. (45):

$$C1\_z1\_int(A, f, B, k, \phi, z1) := \qquad \text{Eq. (45)}$$

$$\int_{z1}^{\frac{1}{f}+z1} \begin{bmatrix} B \cdot \sin[(2 \cdot \pi \cdot k \cdot t) + \phi] + \\ A \cdot \sin(2 \cdot \pi \cdot f \cdot t) \end{bmatrix} \cdot \cos[2 \cdot \pi \cdot f \cdot (t - z1)] dt$$

Here, the modified modulation function is seen to be cos [2πf(t−z1)]. The A term for Eq. (45) is shown in Eq. (46):

$$C1\_Aonly\_z1(A, f, B, k, \phi, z1) := \frac{1}{2 \cdot f} \cdot A \cdot \sin\left(\frac{2 \cdot \pi \cdot}{z1 \cdot f}\right) \qquad \text{Eq. (46)}$$

and B term shown in Eq. (47):

$$C1\_Bonly\_z1(A, f, B, k, \phi, z1) := \qquad \text{Eq. (47)}$$

$$\frac{-B \cdot k}{\pi \cdot (f^2 - k^2)} \cdot \sin\left(\frac{1}{f} \cdot \pi \cdot k\right) \cdot \sin\left(\frac{1}{f} \cdot \pi \cdot k + \phi + 2 \cdot \pi \cdot k \cdot z1\right)$$

Beyond this, and as described above, because the coriolis mode is asynchronous, there is a different timing offset for the zero crossings at the beginning and the end of the integral. The analytical convenience is described above of denoting the time offset (from the point of true zero phase on the drive mode) at the beginning of the integral as z1, while adding the additional time offset z2 to the end of the integral period. Of course, it also may be possible to express the combined time offset as a single parameter.

A further effect of the offset zero crossings is that as the zero crossings are not exactly 1/f seconds apart, the wrong modulation frequency is applied; instead of using frequency f, as above, the modulation frequency within the now-modified modulation function(s) is given by f/(1+f*z2). The size of the expressions involved suggest separating A and B terms. Thus the A integral is defined in Eq. (48) as:

$$S1\_Aonly\_z2\_int(A, f, B, k, \phi, z1, z2) := \qquad \text{Eq. (48)}$$

$$\int_{z1}^{\frac{1}{f}+z1+z2} A \cdot \sin(2 \cdot \pi \cdot f \cdot t) \cdot \sin\left[2 \cdot \pi \cdot \frac{f}{(1+f \cdot z2)} \cdot (t - z1)\right] dt$$

The analytical value of Eq. (48) is given by Eq. (49);

$$S1\_Aonly\_z2(A, f, B, k, \phi, z1, z2) := \qquad \text{Eq. (49)}$$
$$A \cdot \sin(\pi \cdot f \cdot z2) \cdot \cos[\pi \cdot f \cdot (2 \cdot z1 + z2)] \cdot \frac{1 + f \cdot z2}{f^2 \cdot \pi \cdot (2 + f \cdot z2) \cdot z2}$$

As in the previous analysis, Eq. (49) contains a sinc function, only in terms of f rather than k: $\sin(\pi \cdot f \cdot z2)/(\pi \cdot f \cdot z2)$ which is well behaved as z2->0; it can be shown analytically that this expression tends to the function S1_Aonly_z1 defined above in Eq. (43) for small z2.

The B integral is defined in Eq. (50) as:

$$S1\_Bonly\_z2\_int(A, f, B, k, \phi, z1, z2) := \qquad \text{Eq. (50)}$$
$$\int_{z1}^{\frac{1}{f}+z1+z2} [B \cdot \sin[(2 \cdot \pi \cdot k \cdot t) + \phi]] \cdot$$
$$\sin\left[2 \cdot \pi \cdot \frac{f}{(1 + f \cdot z2)} \cdot (t - z1)\right] dt$$

An analytical expression for a value of Eq. (50) is given by Eq. (51):

$$S1\_Bonly\_z2(A, f, B, k, \phi, z1, z2) := B \cdot f \cdot \qquad \text{Eq. (51)}$$
$$\frac{1 + f \cdot z2}{2\pi \cdot (k + f \cdot k \cdot z2 + f) \cdot} \cdot \left[ \sin\left[2 \cdot \pi \cdot k \cdot \left(\frac{1}{f} + z1 + z2\right) + \phi\right] - \right.$$
$$\left. (k + f \cdot k \cdot z2 - f) \qquad \sin(2 \cdot \pi \cdot z1 \cdot k + \phi) \right]$$

The total integral value is given by the sum of the A and B terms of Eq. (49) and Eq. (51), respectively.

The corresponding cosine integral is shown in Eq. (52):

$$C1\_z2\_int(A, f, B, k, \phi, z1, z2) := \qquad \text{Eq. (52)}$$
$$\int_{z1}^{\frac{1}{f}+z1+z2} \left[ \begin{array}{c} B \cdot \sin[(2 \cdot \pi \cdot k \cdot t) + \phi] + \\ A \cdot \sin(2 \cdot \pi \cdot f \cdot t) \end{array} \right] \cdot$$
$$\cos\left[2 \cdot \pi \cdot \frac{f}{1 + f \cdot z2} \cdot (t - z1)\right] dt$$

where the A term is analytically equal to Eq. (53);

$$C1\_Aonly\_z2(A, f, B, k, \phi, z1, z2) := \qquad \text{Eq. (53)}$$
$$\frac{A \cdot (1 + f \cdot z2)^2}{f^2 \cdot \pi \cdot z2 \cdot (2 + f \cdot z2)} \cdot \sin(\pi \cdot f \cdot z2) \cdot [\sin[\pi \cdot f \cdot (2 \cdot z1 + z2)]]$$

Then, the B term is shown in Eq. (54):

$$C1\_Bonly\_z2(A, f, B, k, \phi, z1, z2) := \qquad \text{Eq. (54)}$$
$$-B \cdot k \cdot \frac{(1 + f \cdot z2)^2}{2\pi \cdot (k + f \cdot k \cdot z2 + f) \cdot (k + f \cdot k \cdot z2 - f)} \cdot \left[ \cos\left[2 \cdot \right.\right.$$
$$\left.\left. \pi \cdot k \cdot \left(\frac{1}{f} + z1 + z2\right) + \phi\right] - \cos(2 \cdot \pi \cdot z1 \cdot k + \phi) \right]$$

Eqs. (48)-(54) define the influence of the coriolis mode on the integral values that are calculated, assuming the start and end points of the integral are shifted from the points of zero phase in the drive mode by z1 and z1+z2 seconds, respectively, as described. In other words, Eqs. (48)-(54) show what is calculated during an integration between zero crossings related to the drive mode signal 302. Eqs. (48)-(54) above are analytically exact for any values of z1 and z2 (and for any of the other described parameters).

Thus, Eqs. (48)-(54) illustrate an alternative solution approach for determining drive parameters and coriolis signal parameters. That is, given the observed zero crossings (as detected, for example, by the zero-crossing detector 265) and the numerical values of the S1_int_z2 and C1_int_z2 integrals of Eqs. (48)/(50) and (52), respectively, the values of A, f, B, k, $\phi$, z1, and z2, may be deduced. In particular, it may be possible to make certain assumptions regarding relationships between the parameters A, f, B, k, $\phi$, z1, and z2, such as the relationship between f and k for a specific flowtube, as referred to above. Other assumptions may be made about how parameter values vary from drive cycle to cycle during operation of the flowmeters 200 or 700.

However, the approaches described above with respect to FIGS. 2-11 take the basic analysis of Eqs. (48)-(54), and modify both the integration limits and the modulation functions to encapsulate required information regarding the drive parameters and the Coriolis parameters within the sensor signal, in a form that is amenable to solution for each.

Thus, the approaches of FIGS. 2-11 describe analysis of a sensor signal having a relatively large term (e.g., the amplitude of A is typically 300 mV) and a relatively small term (e.g., the amplitude of B is typically less than or equal to 3 mV, and may be 0.1 mV or less in many cases), where both are to be calculated to very high precision. The various solution techniques operate by first selecting the integral limits and the modulation function such that the smaller influence (Coriolis mode) is reduced or eliminated entirely, so that a very accurate estimate of the larger influence (drive mode) may be obtained. Then, use this very accurate estimate of the larger influence to deduce the residual effect of the smaller influence.

Specifically, as described above, integrating over the period of the coriolis mode instead of the period of the drive mode allows for effective separation of the drive (A) and Coriolis (B) terms. Further, if the sensor signal 304 is integrated over the period of the coriolis mode, and a modulation function is used which is twice the coriolis mode frequency (i.e. 2k), then the influence of the coriolis mode (B) term will be largely or entirely eliminated. If, however, a modulation function which is equal to the coriolis frequency (i.e., k) is used, then this will maximize the influence of the coriolis (B) term.

It is for this reason that the techniques of FIGS. 2-11 effectively generate four integral values instead of the two integral forms of, for example, Eqs. (48)/(50) and (52). These four integral values include two sets of sine and cosine terms, having modulating frequency 2k and k, respectively, and are referred to above as CS2, CC2, CS1, and CC1. From these integrals, as described above, the various drive parameters and coriolis parameters may be determined.

FIGS. 12-15 and the corresponding discussion, below, illustrate a development of these techniques of FIGS. 2-11, based on an extension of the analysis of Eqs. (1)-(4) and Eqs. (38)-(54). Thus, various ones of the Eqs. (5)-(38) are repeated below, as part of this development, and are therefore designated by the same numerical identifiers as above.

Figure 12:
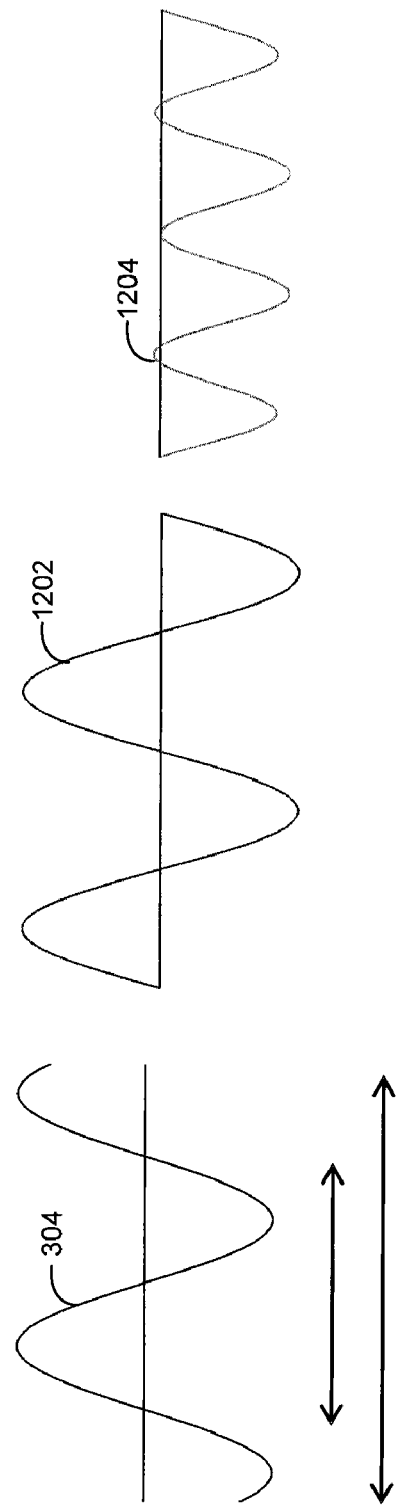
FIG. 12 is a timing graph illustrating a first type of calculation of the flowmeters of FIGS. 2 and 7.

FIG. 12 is a timing graph illustrating a development of the CS2 integrals. In FIG. 12, the sensor signal 304 is illustrated as having integral limits extended symmetrically from the beginning and end of the drive period to make up one complete coriolis period, as shown, and as just described. A modulation function 1202 is shown as being multiplied by the sensor signal 304, to obtain a product signal 1204. As should be understood from the above, the modulation signal 1202 has a frequency that is equal to twice that of the coriolis frequency k, and the product signal 1204 thus includes little or no influence of the coriolis signal 306.

Hence the CS2 integral, here ignoring the influence of z1 and z2, can be written as Eq. (55):

$$CS2\_int(A, f, B, k, \phi) := \qquad \text{Eq. (55)}$$
$$\int_{-\left(\frac{1}{2k}-\frac{1}{2f}\right)}^{\frac{1}{f}+\left(\frac{1}{2k}-\frac{1}{2f}\right)} [B \cdot \sin[(2 \cdot \pi \cdot k \cdot t) + \phi] + A \cdot \sin(2 \cdot \pi \cdot f \cdot t)] \cdot$$
$$\sin\left[4 \cdot \pi \cdot k \cdot \left[t + \left(\frac{1}{2k} - \frac{1}{2f}\right)\right]\right] dt$$

Thus, it may be seen from Eq. (55) that the modulating function sin $[4\pi k[t+((\frac{1}{2}k)-(\frac{1}{2}f))]]$ has frequency $4\pi k$, corresponding to twice the coriolis mode frequency.

The form of the integral limits and the modulation function are explained as follows. The previous assumption that the drive mode phase is close to zero at time t=0 is maintained, so the integral is extended beyond 0 ... 1/f symmetrically, by the period ½k–½f. If the coriolis mode frequency k is lower than that of the drive frequency f, this operation results in an expansion of the integration region. If, however, the coriolis mode frequency is higher than the drive frequency, then the integration region would be reduced. The relevant equations are valid, and may be appropriately expressed, either way.

The analytical value of the CS2 integral is given by Eq. (56):

$$CS2(A, f, B, k, \phi) := \frac{-2 \cdot k \cdot A}{\pi \cdot (f^2 - 4 \cdot k^2)} \cdot \sin\left(\frac{f}{k} \cdot \pi\right) \qquad \text{Eq. (56)}$$

In Eq. (56), the B term has been eliminated entirely, as a result of the fact that the B term is a function of $\sin(2\pi kt)$, and Eq. (56) uses the modulation function of $\sin(4\pi kt)$.

If a non-zero value of initial time offset, z1, is included, then the CS2 integral, or CS2_z1, may be written as above in Eq. (5):

$$CS2\_z1\_int(A, f, B, k, \phi, z1) := \qquad \text{Eq. (5)}$$
$$\int_{-\left(\frac{1}{2k}-\frac{1}{2f}\right)+z1}^{\frac{1}{f}+\left(\frac{1}{2k}-\frac{1}{2f}\right)+z1} [B \cdot \sin[(2 \cdot \pi \cdot k \cdot t) + \phi] + A \cdot \sin(2 \cdot \pi \cdot f \cdot t)] \cdot$$
$$\sin\left[4 \cdot \pi \cdot k \cdot \left[t - z1 + \left(\frac{1}{2k} - \frac{1}{2f}\right)\right]\right] dt$$

with an analytical expression shown in Eq. (6):

$$CS2\_z1(A, f, B, k, \phi, z1) := \qquad \text{Eq. (6)}$$
$$\frac{-2 \cdot k \cdot A}{\pi \cdot (f^2 - 4 \cdot k^2)} \cdot \sin\left(\frac{f}{k} \cdot \pi\right) \cdot \cos(2 \cdot f \cdot \pi \cdot z1)$$

Again, the influence of B has been eliminated.

Finally, if a non-zero value of z2 and corresponding modulation frequency are used, then the CS2 integral, or CS2_z2, may be written as above in Eq. (19):

$$CS2\_z2\_int(A, f, B, k, \phi, z1, z2) := \qquad \text{Eq. (19)}$$
$$\int_{-\left(\frac{1}{2k}-\frac{1}{2f}\right)+z1}^{\frac{1}{f}+\left(\frac{1}{2k}-\frac{1}{2f}\right)+z1+z2} [B \cdot \sin[(2 \cdot \pi \cdot k \cdot t) + \phi] + A \cdot \sin(2 \cdot \pi \cdot f \cdot t)] \cdot$$
$$\sin\left[4 \cdot \pi \cdot \frac{k}{(1+k \cdot z2)} \cdot \left[t - z1 + \left(\frac{1}{2k} - \frac{1}{2f}\right)\right]\right] dt$$

The A term is given by Eq. (20):

$$CS2\_Aonly\_z2(A, f, B, k, \phi, z1, z2) := -2 \cdot A \cdot k \cdot \qquad \text{Eq. (20)}$$
$$(1+k \cdot z2) \cdot \frac{\sin\left[\pi \cdot f \cdot \left(\frac{1}{k}+z2\right)\right] \cdot \cos[\pi \cdot f \cdot (2 \cdot z1 + z2)]}{\pi \cdot (f + f \cdot k \cdot z2 + 2 \cdot k) \cdot (f + f \cdot k \cdot z2 - 2 \cdot k)}$$

The B term is no longer exactly zero, as shown in Eq. (21):

$$CS2\_Bonly\_z2(A, f, B, k, \phi, z1, z2) := \qquad \text{Eq. (21)}$$
$$\frac{2 \cdot B \cdot (1 + k \cdot z2)}{\pi \cdot k \cdot (3 + k \cdot z2) \cdot (1 - k \cdot z2)} \cdot$$
$$\cos\left[k \cdot \pi \cdot \left(\frac{1}{f} + 2 \cdot z1 + z2\right) + \phi\right] \cdot \sin(\pi \cdot k \cdot z2)$$

However, it is very small, being a product of both B itself and sin(z2), both of which may be assumed to be small.

Figure 13:
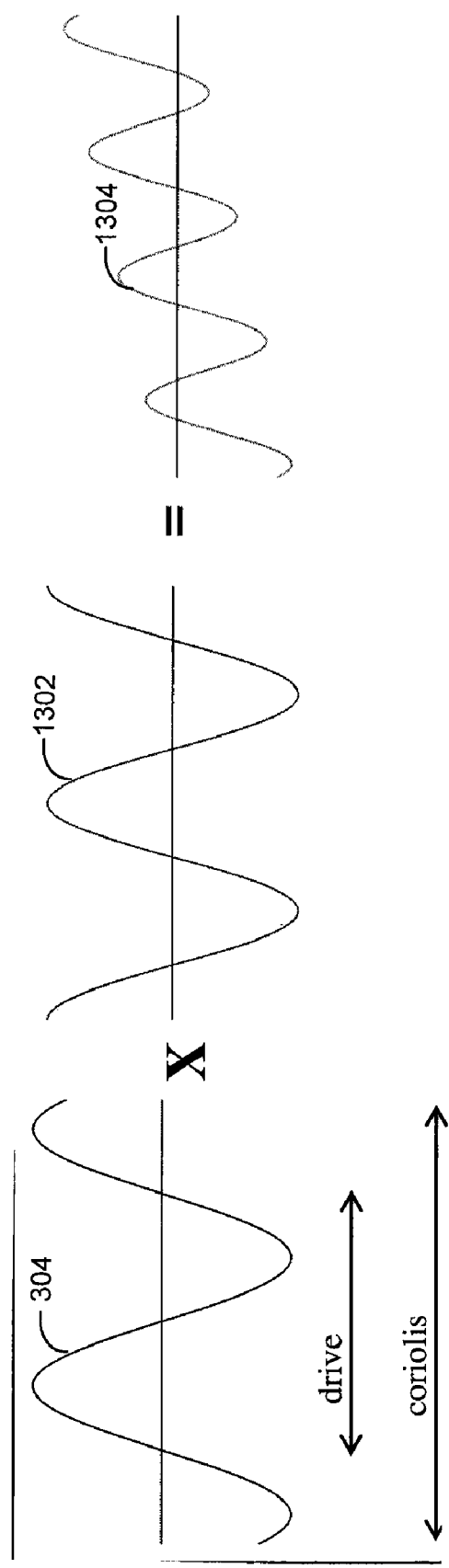
FIG. 13 is a timing graph illustrating a second type of calculation of the flowmeters of FIGS. 2 and 7.

FIG. 13 is a timing graph illustrating a development of the CC2 integrals. The major change from CS2 in FIG. 12 and the above discussion, is that a modulation function 1304 is a cosine rather than a sine function, leading to a different product function 1302 than seen in FIG. 12.

Thus, first assuming both z1 and z2 are zero, the CC2 integral takes the form of Eq. (57):

$$CC2\_int(A, f, B, k, \phi) := \qquad \text{Eq. (57)}$$
$$\int_{-\left(\frac{1}{2k}-\frac{1}{2f}\right)}^{\frac{1}{f}+\left(\frac{1}{2k}-\frac{1}{2f}\right)} [B \cdot \sin[(2 \cdot \pi \cdot k \cdot t) + \phi] + A \cdot \sin(2 \cdot \pi \cdot f \cdot t)] \cdot$$
$$\cos\left[4 \cdot \pi \cdot k \cdot \left[t + \left(\frac{1}{2k} - \frac{1}{2f}\right)\right]\right] dt$$

Eq. (57) has a value of exactly zero, as both the A term and B term disappear.

Next allowing for a non-zero value of z1, the value CC2_z1 may be expressed as above in Eq. (7):

$$CC2\_z1\_int(A, f, B, k, \phi, z1) := \qquad \text{Eq. (7)}$$

$$\int_{-\left(\frac{1}{2k}-\frac{1}{2f}\right)+z1}^{\frac{1}{f}+\left(\frac{1}{2k}-\frac{1}{2f}\right)+z1} [B \cdot \sin[(2 \cdot \pi \cdot k \cdot t) + \phi] + A \cdot \sin(2 \cdot \pi \cdot f \cdot t)] \cdot$$

$$\cos\left[4 \cdot \pi \cdot k \cdot \left[t - z1 + \left(\frac{1}{2k} - \frac{1}{2f}\right)\right]\right] dt$$

which has analytical form, in which again the B term is exactly zero, as shown in Eq. (8):

$$CC2\_z1(A, f, B, k, \phi, z1) := \qquad \text{Eq. (8)}$$

$$\frac{-A \cdot f}{\pi \cdot (f^2 - 4 \cdot k^2)} \cdot \sin\left(\frac{f}{k} \cdot \pi\right) \cdot \sin(2 \cdot f \cdot \pi \cdot z1)$$

Finally, and most generally, allowing non-zero z1 and z2, and the resulting error in the modulation frequency, the CC2_z2 integral may be written as in Eq. (22):

$$CC2\_z2\_int(A, f, B, k, \phi, z1, z2) := \qquad \text{Eq. (22)}$$

$$\int_{-\left(\frac{1}{2k}-\frac{1}{2f}\right)+z1}^{\frac{1}{f}+\left(\frac{1}{2k}-\frac{1}{2f}\right)+z1+z2} [B \cdot \sin[(2 \cdot \pi \cdot k \cdot t) + \phi] + A \cdot \sin(2 \cdot \pi \cdot f \cdot t)] \cdot$$

$$\cos\left[4 \cdot \pi \cdot \frac{k}{(1+k \cdot z2)} \cdot \left[t - z1 + \left(\frac{1}{2k} - \frac{1}{2f}\right)\right]\right] dt$$

Thus, the A term for CC2_z2 of Eq. (22) takes the form of Eq. (23):

$$CC2\_Aonly\_z2(A, f, B, k, \phi, z1, z2) := -A \cdot f \cdot \qquad \text{Eq. (23)}$$

$$(1 + k \cdot z2)^2 \cdot \frac{\sin\left[\pi \cdot f \cdot \left(\frac{1}{k} + z2\right)\right] \cdot \sin[\pi \cdot f \cdot (2 \cdot z1 + z2)]}{\pi \cdot (f + f \cdot k \cdot z2 + 2 \cdot k) \cdot (f + f \cdot k \cdot z2 - 2 \cdot k)}$$

while the B term takes the form of Eq. (24):

$$CC2\_Bonly\_z2(A, f, B, k, \phi, z1, z2) := \qquad \text{Eq. (24)}$$

$$\frac{-B \cdot (1 + k \cdot z2)^2}{\pi \cdot k \cdot (k \cdot z2 + 3) \cdot (k \cdot z2 - 1)} \cdot$$

$$\sin\left[k \cdot \pi \cdot \left(\frac{1}{f} + 2 \cdot z1 + z2\right) + \phi\right] \cdot \sin(\pi \cdot k \cdot z2)$$

which again, being a product of B and sin(z2), is small.

Figure 14:
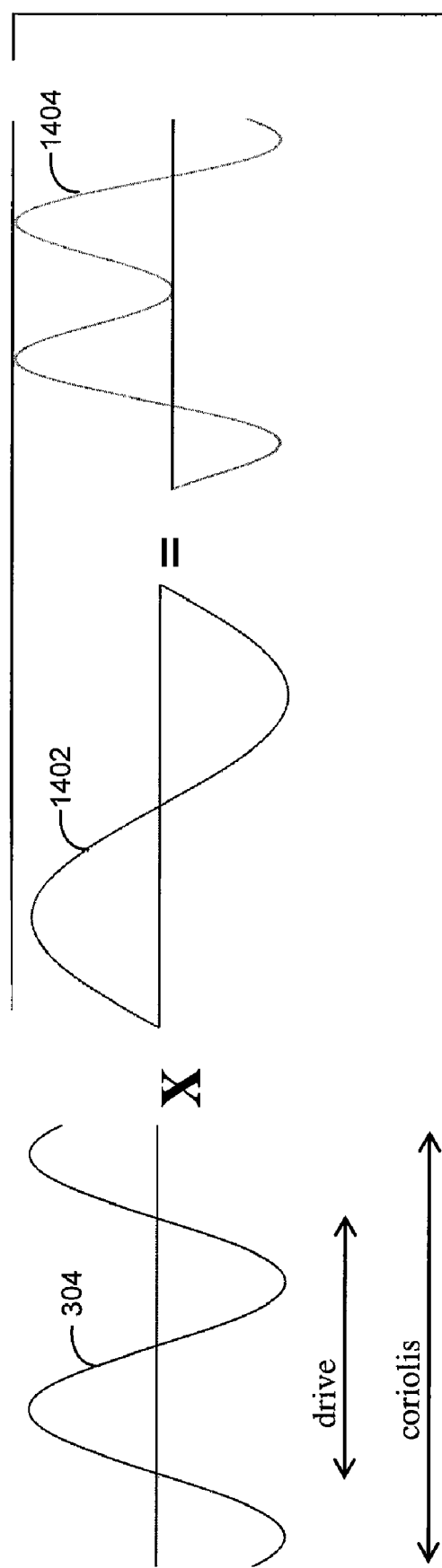
FIG. 14 is a timing graph illustrating a third type of calculation of the flowmeters of FIGS. 2 and 7.

FIG. 14 is a timing graph illustrating a development of the CS1 integrals. In FIG. 14, as shown, a modulating function 1402 completes a single cycle over the integration period, having the coriolis frequency k, thus resulting in a product function 1404.

Proceeding through to the development of the CS1 integrals, the first CS1 integral, i.e., assuming z1 and z2 are both zero, is defined as in Eq. (58):

$$CS1\_int(A, f, B, k, \phi) := \qquad \text{Eq. (58)}$$

$$\int_{-\left(\frac{1}{2k}-\frac{1}{2f}\right)}^{\frac{1}{f}+\left(\frac{1}{2k}-\frac{1}{2f}\right)} [B \cdot \sin[(2 \cdot \pi \cdot k \cdot t) + \phi] + A \cdot \sin(2 \cdot \pi \cdot f \cdot t)] \cdot$$

$$\sin\left[2 \cdot \pi \cdot k \cdot \left[t + \left(\frac{1}{2k} - \frac{1}{2f}\right)\right]\right] dt$$

The analytic value of Eq. (58) is given by Eq. (59):

$$CS1(A, f, B, k, \phi) := \qquad \text{Eq. (59)}$$

$$\frac{-k \cdot A}{\pi \cdot (f^2 - k^2)} \cdot \sin\left(\frac{f}{k} \cdot \pi\right) - \frac{B}{2k} \cdot \cos\left(\frac{k}{f} \cdot \pi + \phi\right)$$

Assuming next a non-zero value of z1, the CS1_z1 integral is shown in Eq. (9) as:

$$CS1\_z1\_int(A, f, B, k, \phi, z1) := \qquad \text{Eq. (9)}$$

$$\int_{-\left(\frac{1}{2k}-\frac{1}{2f}\right)+z1}^{\frac{1}{f}+\left(\frac{1}{2k}-\frac{1}{2f}\right)+z1} [B \cdot \sin[(2 \cdot \pi \cdot k \cdot t) + \phi] + A \cdot \sin(2 \cdot \pi \cdot f \cdot t)] \cdot$$

$$\sin\left[2 \cdot \pi \cdot k \cdot \left[t - z1 + \left(\frac{1}{2k} - \frac{1}{2f}\right)\right]\right] dt$$

Eq. (9) has an A term given by Eq. (10):

$$CS1\_Aonly\_z1(A, f, B, k, \phi, z1) := \qquad \text{Eq. (10)}$$

$$\frac{-k \cdot A}{\pi \cdot (f^2 - k^2)} \cdot \sin\left(\frac{f}{k} \cdot \pi\right) \cdot \cos(2 \cdot f \cdot \pi \cdot z1)$$

Eq. (10) has a B term given by Eq. (11):

$$CS1\_Bonly\_z1(A, f, B, k, \phi, z1) := \qquad \text{Eq. (11)}$$

$$\frac{-B}{2 \cdot k} \cdot \cos\left[k \cdot \pi \cdot \left(\frac{1}{f} + 2 \cdot z1\right) + \phi\right]$$

Finally, with a non-zero z2 term, the CS1_z2 integral may be written as in Eq. (25):

$$CS1\_z2\_int(A, f, B, k, \phi, z1, z2) := \qquad \text{Eq. (25)}$$

$$\int_{-\left(\frac{1}{2k}-\frac{1}{2f}\right)+z1}^{\frac{1}{f}+\left(\frac{1}{2k}-\frac{1}{2f}\right)+z1+z2} [B \cdot \sin[(2 \cdot \pi \cdot k \cdot t) + \phi] + A \cdot \sin(2 \cdot \pi \cdot f \cdot t)] \cdot$$

$$\sin\left[2 \cdot \pi \cdot \frac{k}{(1+k \cdot z2)} \cdot \left[t - z1 + \left(\frac{1}{2k} - \frac{1}{2f}\right)\right]\right] dt$$

Eq. (25) has an analytical expression for the A term given by Eq. (26):

$$CS1\_Aonly\_z2(A, f, B, k, \phi, z1, z2) :=$$

$$-A \cdot k \cdot (1 + k \cdot z2) \cdot \frac{\sin\left[\pi \cdot f \cdot \left(\frac{1}{k} + z2\right)\right] \cdot \cos[\pi \cdot f \cdot (2 \cdot z1 + z2)]}{\pi \cdot (f + f \cdot k \cdot z2 + k) \cdot (f + f \cdot k \cdot z2 - k)} \quad \text{Eq. (26)}$$

Eq. (26) has a B term given by Eq. (27):

$$CS1\_Bonly\_z2(A, f, B, k, \phi, z1, z2) := \frac{-B \cdot (1 + k \cdot z2)}{\pi \cdot k^2 \cdot z2 \cdot (2 + k \cdot z2)} \cdot \quad \text{Eq. (27)}$$

$$\cos\left[\pi \cdot k \cdot \left(\frac{1}{f} + 2 \cdot z1 + z2\right) + \phi\right] \cdot \sin(\pi \cdot k \cdot z2)$$

The B term of Eq. (27) includes the sinc function $\sin(\pi \cdot k \cdot z2)/(\pi \cdot k \cdot z2)$, and may be shown to tend towards CS1_Bonly_z1 of Eq. (11), as z2 tends to zero.

Figure 15:
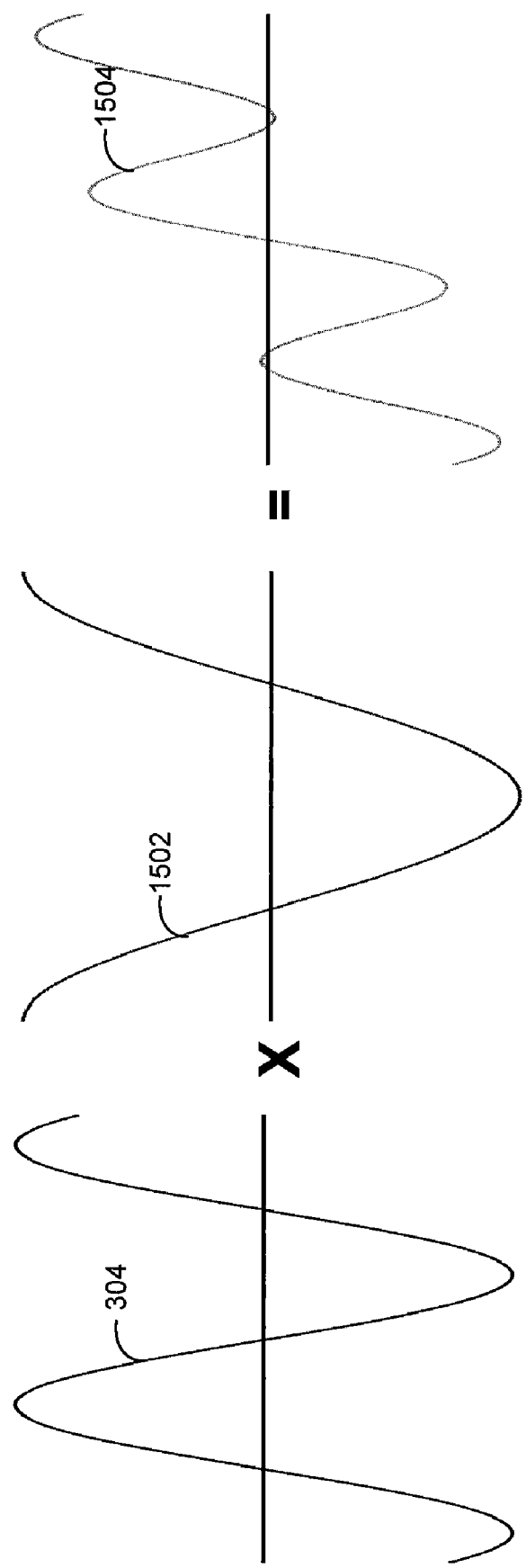
FIG. 15 is a timing graph illustrating a fourth type of calculation of the flowmeters of FIGS. 2 and 7.

FIG. 15 is a timing graph illustrating a development of the CC1 integrals. In FIG. 15, as shown, a modulating (cosine) function 1502 completes a single cycle over the integration period, having the coriolis frequency k, and results in a product function 1504.

Proceeding in an analogous fashion to the above, and starting with z1 and z2 both assumed to be zero, the CC1 integral takes the form of Eq. (60):

$$CC1\_int(A, f, B, k, \phi) := \quad \text{Eq. (60)}$$

$$\int_{-\left(\frac{1}{2k}-\frac{1}{2f}\right)}^{\frac{1}{f}+\left(\frac{1}{2k}-\frac{1}{2f}\right)} [B \cdot \sin[(2 \cdot \pi \cdot k \cdot t) + \phi] + A \cdot \sin(2 \cdot \pi \cdot f \cdot t)] \cdot$$

$$\cos\left[2 \cdot \pi \cdot k \cdot \left[t + \left(\frac{1}{2k} - \frac{1}{2f}\right)\right]\right] dt$$

The A term disappears, leaving only the following B term of Eq. (61):

$$CC1(A, f, B, k, \phi) := \frac{-B}{2 \cdot k} \cdot \sin\left(\frac{k}{f} \cdot \pi + \phi\right) \quad \text{Eq. (61)}$$

With a non-zero value of z1, the CC1_z1 integral may be shown as above in Eq. (12):

$$CC1\_z1\_int(A, f, B, k, \phi, z1) := \quad \text{Eq. (12)}$$

$$\int_{-\left(\frac{1}{2k}-\frac{1}{2f}\right)+z1}^{\frac{1}{f}+\left(\frac{1}{2k}-\frac{1}{2f}\right)+z1} [B \cdot \sin[(2 \cdot \pi \cdot k \cdot t) + \phi] + A \cdot \sin(2 \cdot \pi \cdot f \cdot t)] \cdot$$

$$\cos\left[2 \cdot \pi \cdot k \cdot \left[t - z1 + \left(\frac{1}{2k} - \frac{1}{2f}\right)\right]\right] dt$$

Eq. (12) results in an A term of Eq. (13):

$$CC1\_Aonly\_z1(A, f, B, k, \phi, z1) := \quad \text{Eq. (13)}$$

$$\frac{-f \cdot A}{\pi \cdot (f^2 - k^2)} \cdot \sin\left(\frac{f}{k} \cdot \pi\right) \cdot \sin(2 \cdot f \cdot \pi \cdot z1)$$

Eq. (13) results in a B term of Eq. (14):

$$CC1\_Bonly\_z1(A, f, B, k, \phi, z1) := \quad \text{Eq. (14)}$$

$$\frac{-B}{2 \cdot k} \cdot \sin\left[k \cdot \pi \cdot \left(\frac{1}{f} + 2 \cdot z1\right) + \phi\right]$$

Finally, with non-zero z2, the CC1_z2 integral is represented in Eq. (28) as:

$$CC1\_z2\_int(A, f, B, k, \phi, z1, z2) := \quad \text{Eq. (28)}$$

$$\int_{-\left(\frac{1}{2k}-\frac{1}{2f}\right)}^{\frac{1}{f}+\left(\frac{1}{2k}-\frac{1}{2f}\right)+z1+z2} [B \cdot \sin[(2 \cdot \pi \cdot k \cdot t) + \phi] + A \cdot \sin(2 \cdot \pi \cdot f \cdot t)] \cdot$$

$$\cos\left[2 \cdot \pi \cdot \frac{k}{(1 + k \cdot z2)} \cdot \left[t - z1 + \left(\frac{1}{2k} - \frac{1}{2f}\right)\right]\right] dt$$

For Eq. (28), the A term may be written as in Eq. (29):

$$CC1\_Aonly\_z2(A, f, B, k, \phi, z1, z2) := \quad \text{Eq. (29)}$$

$$-A \cdot f \cdot (1 + k \cdot z2)^2 \cdot \frac{\sin\left[\pi \cdot f \cdot \left(\frac{1}{k} + z2\right)\right] \cdot \sin[\pi \cdot f \cdot (2 \cdot z1 + z2)]}{\pi \cdot (f + f \cdot k \cdot z2 + k) \cdot (f + f \cdot k \cdot z2 - k)}$$

Further for Eq. (29), the B term, where again the sinc function $\sin(\pi \cdot k \cdot z2)/(\pi \cdot k \cdot z2)$ in included, may be written as in Eq. (30):

$$CC1\_Bonly\_z2(A, f, B, k, \phi, z1, z2) := \frac{-B \cdot (1 + k \cdot z2)^2}{\pi \cdot k^2 \cdot z2 \cdot (2 + k \cdot z2)} \cdot \quad \text{Eq. (30)}$$

$$\sin\left[\pi \cdot k \cdot \left(\frac{1}{f} + 2 \cdot z1 + z2\right) + \phi\right] \cdot \sin(\pi \cdot k \cdot z2)$$

Thus, the above discussion of FIGS. 12-15 illustrates a development of all of the CS2_z1, CC2_z1, CS1_z1, CC1_z1, CS2_z2, CC2_z2, CS1_z2, and CC1_z2 integrals, the development being based on extensions of existing techniques for performing Fourier analysis of the sensor signal 304.

FIGS. 16-22 illustrate examples of results of implementations of the techniques of FIGS. 2-11, above. In FIGS. 16-22, unless mentioned otherwise, data is illustrated in which parameter values are A=0.3, f=100 Hz, k=f/√3, and B=0.005. Of course, these parameters are merely for example's sake.

Figure 16A:
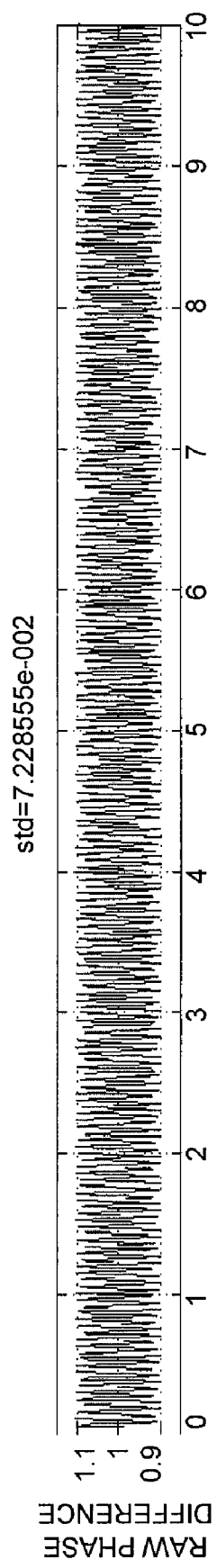
FIGS. 16A and 16B are graphs illustrating a phase difference between two sensor signals.
Figure 16B:
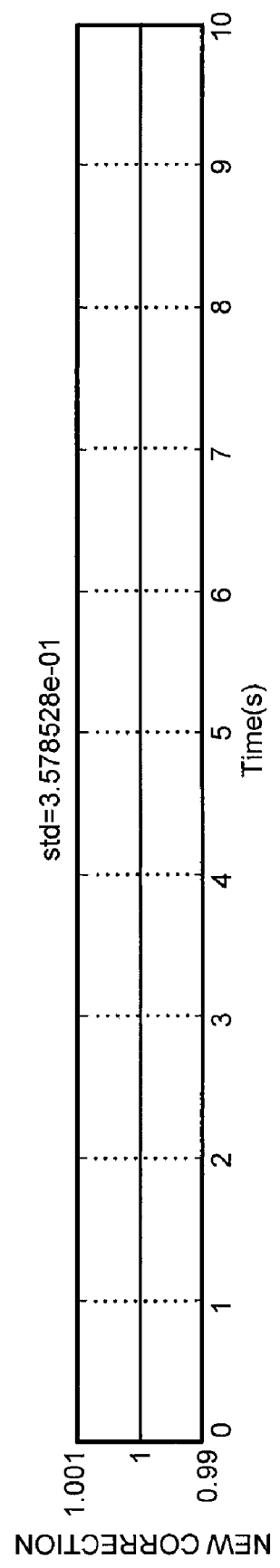

FIGS. 16A and 16B are graphs illustrating a phase difference between two sensor signals 304, e.g., between two offsets z1 of two signals from two sensors 205. FIG. 16A illustrates a raw phase difference, before the corrections discussed above, and FIG. 16B illustrates a phase difference after the corrections.

FIGS. 17A and 17B are graphs illustrating an average frequency f (in FIG. 17A) and a corrected frequency $f_{revised}$ (in FIG. 17B). As illustrated, significant improvements in frequency values, and reductions in errors, may be obtained by using the techniques described above with respect to FIG.

9 (916). For example, a standard deduction reduction of 10-1000 may be obtained, depending, for example, on the level of coriolis noise.

Figure 18:
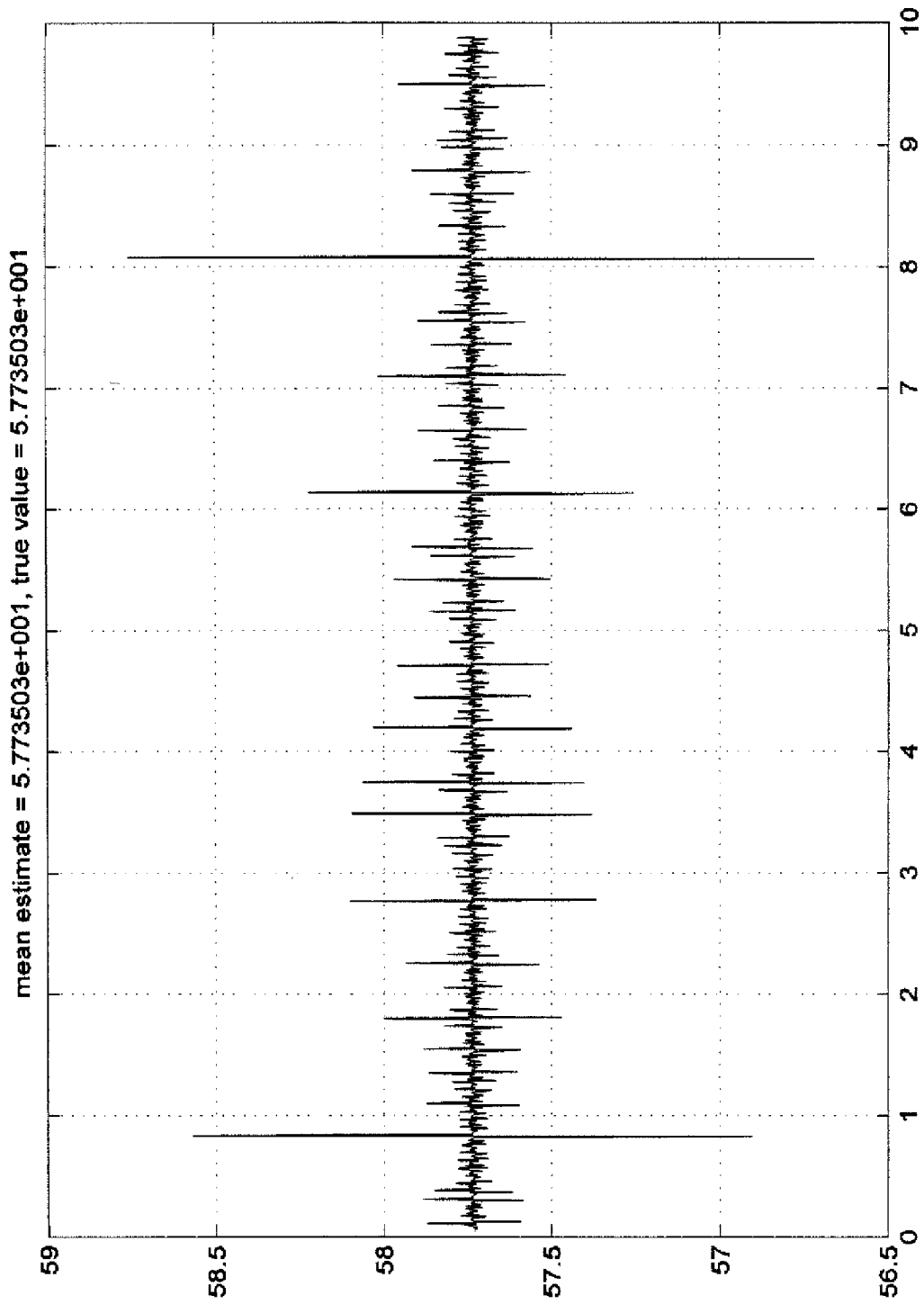
FIG. 18 is a graph illustrating an example of a coriolis frequency estimation.

FIG. 18 is a graph illustrating an example of a coriolis frequency estimation along the lines described above with respect to FIG. 9 (916). That is, FIG. 18 illustrates the calculations of an average coriolis frequency over a given time period. As described above, a ratio or other relationship between $f_{revised}$ of FIGS. 17B and k of FIG. 18 may be determined.

Figure 19A:
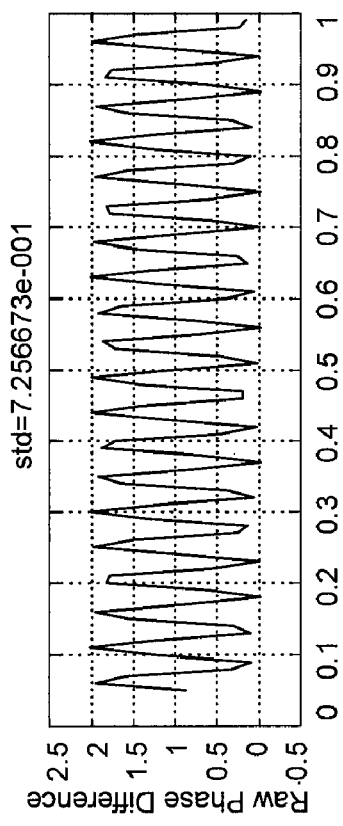
FIGS. 19A-19D are graphs illustrating raw and corrected values for amplitude and phase of a drive signal.
Figure 19B:
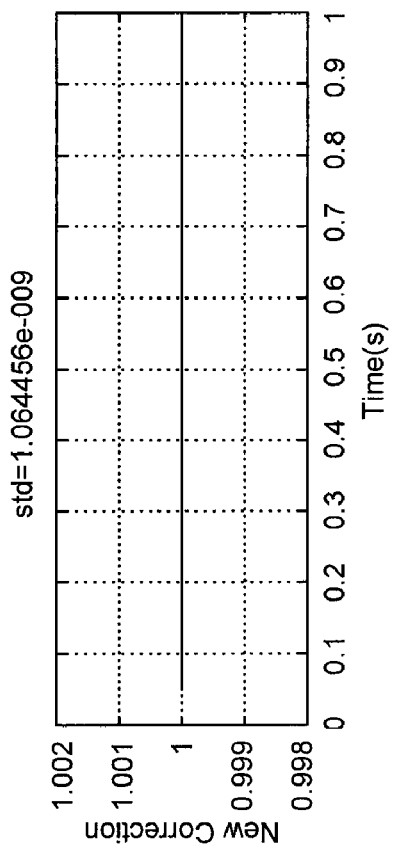
Figure 19C:
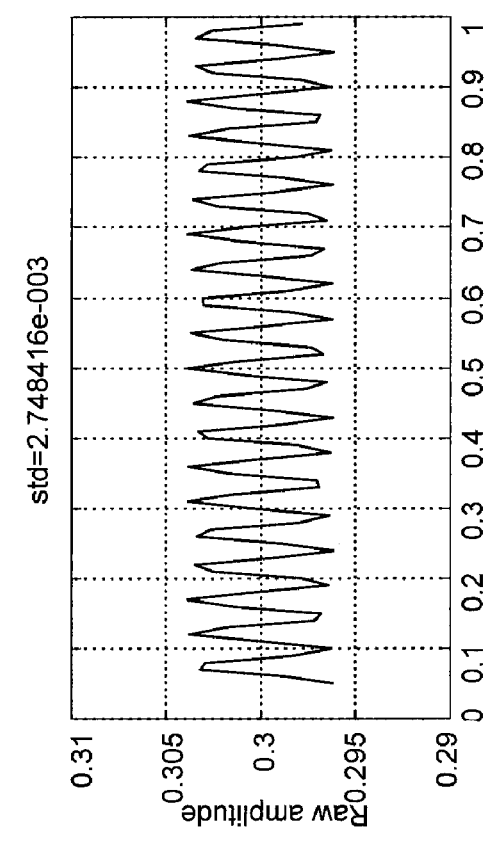
Figure 19D:
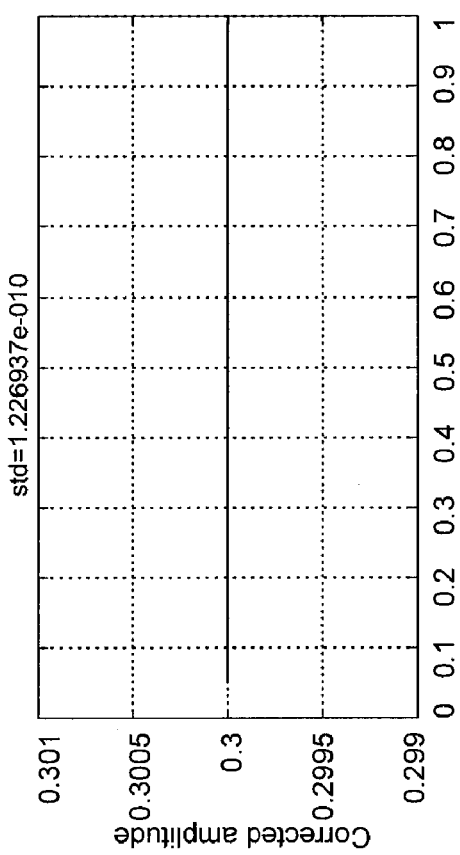

FIGS. 19A-19D are graphs illustrating raw and corrected values for amplitude and phase of a drive signal. Specifically, FIGS. 19A and 19B illustrate a raw and corrected amplitude of a drive signal, while FIGS. 19C and 19D illustrate a raw and corrected phase difference z1. As shown, significant reductions in standard deviation may be obtained. Moreover, the beating pattern that typically occurs at the difference between the drive frequency and the coriolis frequency, referred to above, may be eliminated.

Figure 20A:
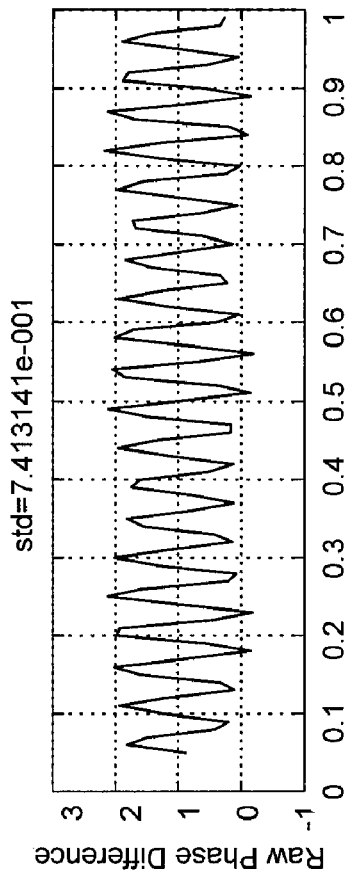
FIGS. 20A-20D are graphs illustrating amplitude modulation of a drive signal.
Figure 20C:
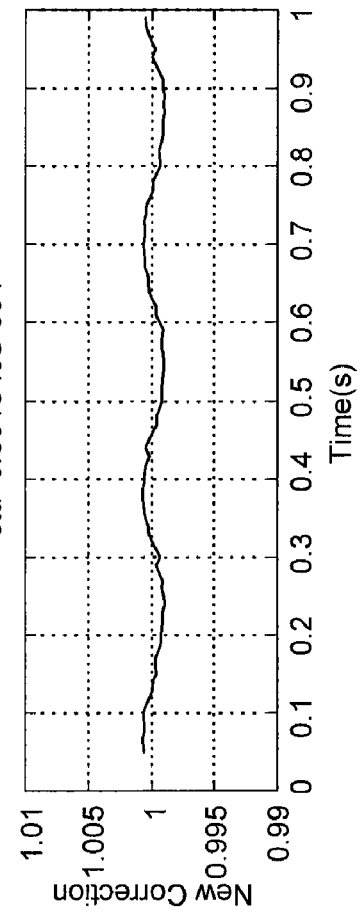
Figure 20B:
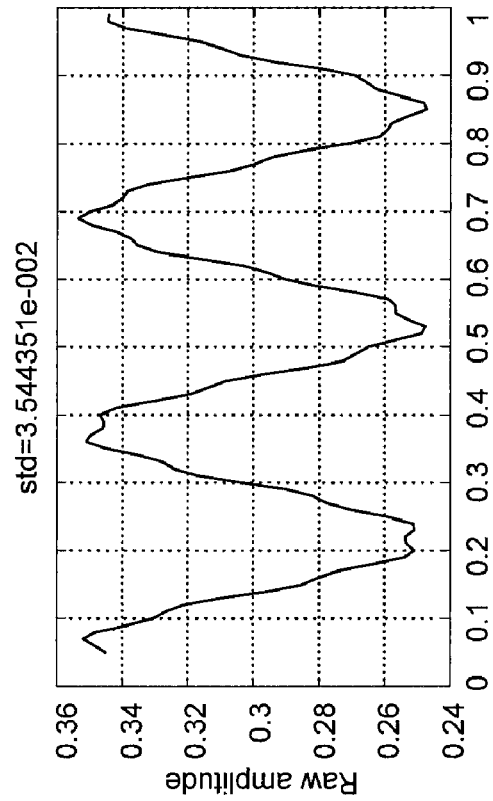
Figure 20D:
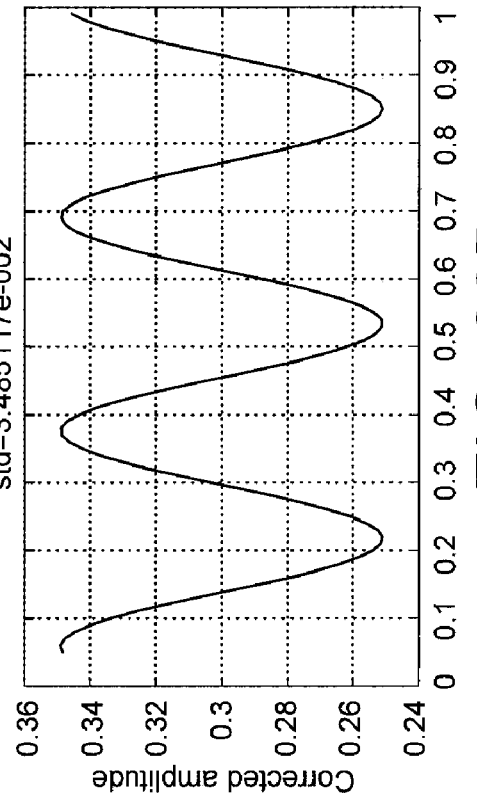

FIGS. 20A-20D are graphs illustrating amplitude modulation of a drive signal. In FIGS. 20A and 20B, a raw and corrected amplitude respectively, are illustrated. In FIGS. 20C and 20D, a raw and corrected phase difference, respectively, are illustrated.

Figure 21A:
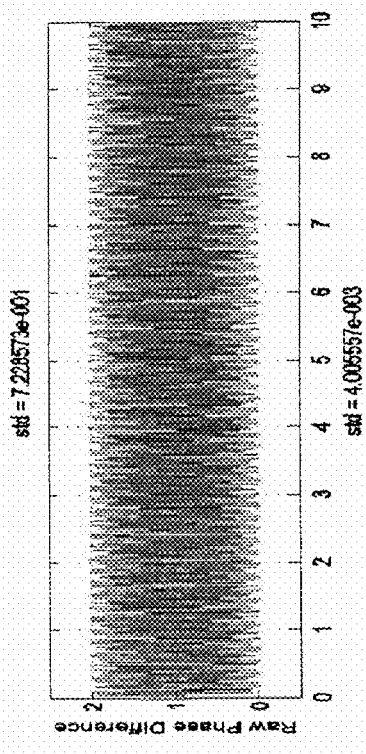
FIGS. 21A-21D are graphs illustrating a step change in phase difference of a drive signal.
Figure 21C:
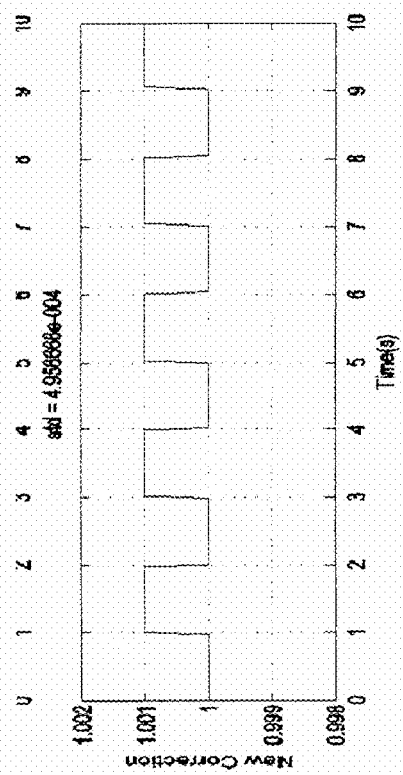
Figure 21B:
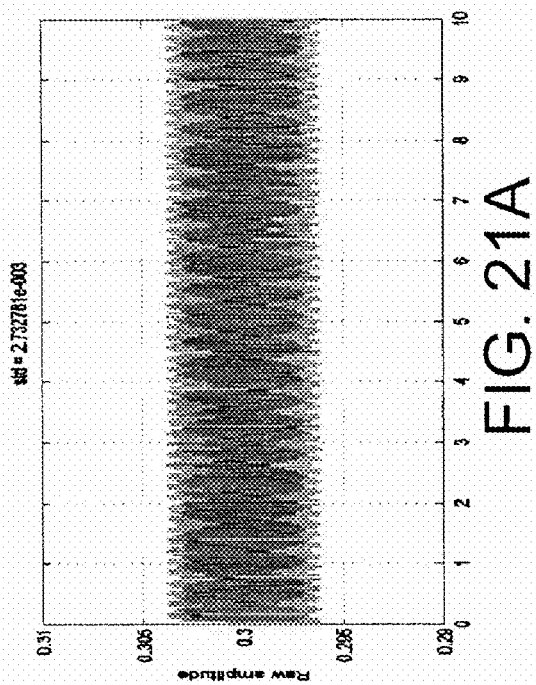
Figure 21D:
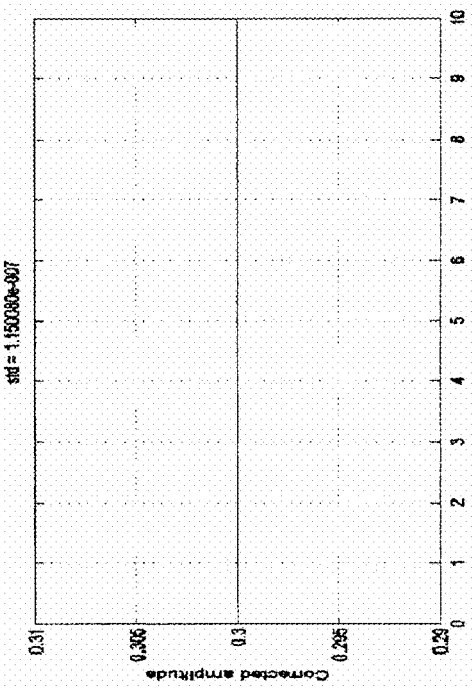

FIGS. 21A-21D are graphs illustrating a step change in phase difference of a drive signal. In FIGS. 21A and 21B, a raw and corrected amplitude respectively, are illustrated. In FIGS. 21C and 21D, a raw and corrected phase difference, respectively, are illustrated. As may be seen, the step changes in phase difference are obscured by noise in FIG. 21C, but are clearly visible in FIG. 21D.

Figure 22A:
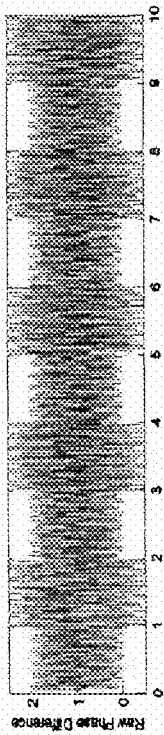
FIGS. 22A-22E are graphs illustrating variations in the coriolis amplitude.
Figure 22B:
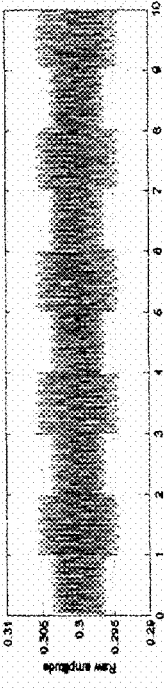
Figure 22C:
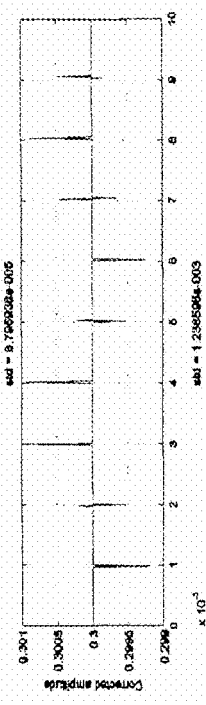
Figure 22D:
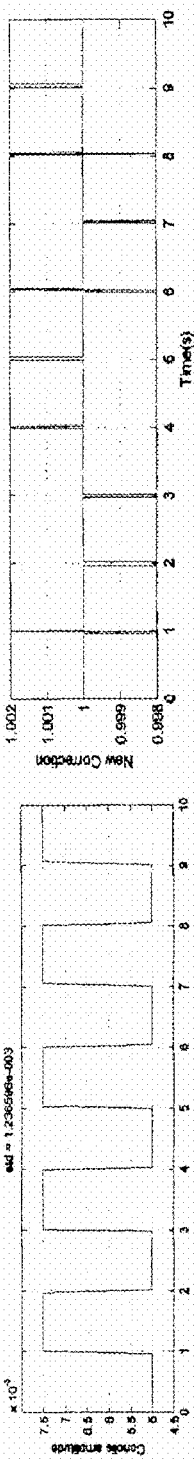

Finally, FIGS. 22A-22E are graphs illustrating variations in the coriolis amplitude B. In FIG. 22A, a raw amplitude of a sensor signal is illustrated, while a corrected amplitude is illustrated in FIG. 22B. A raw phase difference is shown in FIG. 22C, while a corrected phase difference is shown in FIG. 22D.

Figure 22E:
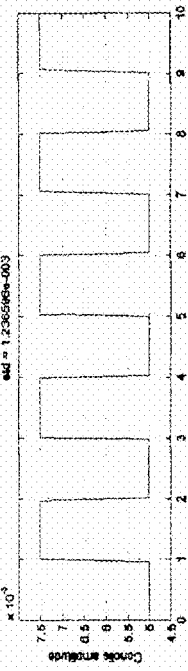

Finally, FIG. 22E illustrates a change in coriolis amplitude that results from any of the various effects referenced above, e.g., external vibrations of the flowtube 215. In FIG. 22E, the coriolis amplitude, as shown, varies between 0.005V and 0.0075V. As shown, the coriolis amplitude B may be determined to a high level of accuracy, so that the originating causes of the changes in B may be identified, characterized, and/or determined.

Techniques are described above in which a sensor signal having a major (drive) signal component and a minor (e.g., coriolis) component may be analyzed so as to characterize the signal components, and, ultimately, to identify parameters of the signal components with a high degree of accuracy. As a result, highly accurate, stable, and responsive measurements may be made of a fluid within a vibratable flowtube, and a new drive signal may be generated that maintains a desired oscillation of the flowtube.

In these and related techniques, it should be understood that the signal analyzer 255 and the signal identifier 260 of FIGS. 2 and 7 may be implemented at separate locations. For example, the signal analyzer 255 may be implemented within a specialized processor, such as a FPGA, as referred to above, for high-speed calculation of the integration values. Then, the FPGA may send the results of these integrations to the signal identifier 260 on a separate processor, so that the actions of the signal identifier 260 in extracting the various signal parameters from the integral results may be performed with a minimum of computational load.

A number of implementations have been described. Nevertheless, it will be understood that various modifications may be made. Accordingly, other implementations are within the scope of the following claims.

What is claimed is:

1. A method comprising:
   passing a fluid through a flowtube having at least two natural modes of vibration, the modes of vibration having different periods of oscillation;
   applying a drive signal to the flowtube such that the flowtube vibrates;
   receiving a first sensor signal from a first sensor that is operable to sense a vibration of the flowtube, the first sensor signal comprising a first major signal component associated with a first one of the modes of vibration, and a first minor signal component associated with a second one of the modes of vibration;
   receiving a second sensor signal from a second sensor that is operable to sense a vibration of the flowtube, the second sensor signal comprising a second major signal component associated with the first mode of vibration, and a second minor signal component associated with the second mode of vibration;
   analyzing the first received sensor signal over a time period that is defined with respect to the period of oscillation of one of the modes of vibration of the flowtube;
   analyzing the second received sensor signal over a time period that is defined with respect to the period of oscillation of one of the modes of vibration of the flowtube; and
   determining a difference between a phase of the first sensor signal and the second sensor signal based on the analysis of the first received sensor signal and the analysis of the second received sensor signal.

2. The method of claim 1, wherein:
   analyzing the first received signal over a time period that is defined with respect to the period of oscillation of one of the modes of vibration comprises analyzing the first received sensor signal over a time period that is defined with respect to the period of oscillation of the second mode of vibration; and
   analyzing the second received signal over a time period that is defined with respect to the period of oscillation of one of the modes of vibration comprises analyzing the second received sensor signal over a time period that is defined with respect to the period of oscillation of the second mode of vibration.

3. The method of claim 1, wherein:
   analyzing the first received signal over a time period that is defined with respect to the period of oscillation of one of the modes of vibration comprises analyzing the first received sensor signal over a time period that is defined with respect to the period of oscillation of the first mode of vibration; and
   analyzing the second received signal over a time period that is defined with respect to the period of oscillation of one of the modes of vibration comprises analyzing the second received sensor signal over a time period that is defined with respect to the period of oscillation of the first mode of vibration.

4. The method of claim 1, wherein the first mode of vibration comprises a mode of vibration associated with applying the drive signal to the flowtube, and the second mode of vibration comprises a mode of vibration associated with a contaminant.

5. The method of claim 1, wherein the second mode of vibration comprises a mode of vibration excited by an external disturbance applied to the flowtube.

6. The method of claim 5, wherein the external disturbance comprises a change in a flowrate of the fluid passing through the flowtube.

7. The method of claim 1 further comprising determining a mass flowrate of the fluid based on the determined difference between the phase of the first sensor signal and the phase of the second sensor signal.

8. The method of claim 1, wherein the first major signal component has a major amplitude, and the first minor signal component has a minor amplitude, and further comprising determining a value of the major amplitude based on the analysis of the first received sensor signal.

9. The method of claim 8, further comprising:
generating an updated drive signal based on the determined value of the major amplitude; and
applying the updated drive signal to the flowtube.

10. The method of claim 1, wherein the first minor signal component is related to a coriolis mode signal that is present in the sensor signal.

11. The method of claim 1, further comprising:
determining, based on the analysis of the first received sensor signal, a first timing offset between a zero-crossing of the first major signal component and a zero-crossing of the first received sensor signal, the first offset caused at least in part by a presence of the first minor signal component.

12. A method comprising:
passing a fluid through a flowtube having at least two natural modes of vibration, the modes of vibration having different periods of oscillation;
applying a drive signal to the flowtube such that the flowtube vibrates;
receiving a first sensor signal from a first sensor that is operable to sense a vibration of the flowtube, the first sensor signal comprising a first major signal component associated with a first one of the modes of vibration, and a first minor signal component associated with a second one of the modes of vibration;
analyzing the first received sensor signal over a time period that is defined with respect to the period of oscillation of one of the modes of vibration of the flowtube; and
determining a representation of a phase of the first major signal component based on the analysis of the first received sensor signal.

13. The method of claim 12, wherein analyzing the first received sensor signal over a time period that is defined with respect to the period of oscillation of one of the modes of vibration of the flowtube comprises analyzing the first received sensor signal over a time period that is defined with respect to the second mode of vibration.

14. The method of claim 12 further comprising:
receiving a second sensor signal from a second sensor that is operable to sense a vibration of the flowtube, the second sensor signal comprising a second major signal component associated with the first mode of vibration, and a second minor signal component associated with the second mode of vibration;
analyzing the second received sensor signal over a time period that is defined with respect to the period of oscillation of one of the modes of vibration;
determining a representation of a phase of the second major signal component based on analyzing the second received sensor signal; and
determining a difference between the representation of the phase of the first major signal component and the representation of the phase of the second major signal component based on the analysis of the first received sensor signal and the analysis of the second received sensor signal.

15. The method of claim 14 further comprising determining a mass flowrate of the fluid based on the difference between the representation of the phase of the first major signal component and the representation of the phase of the second major signal component.

16. The method of claim 12, wherein the first major signal component has a major amplitude, and the first minor signal component has a minor amplitude, and further comprising determining a value of the major amplitude based on the analysis of the first received sensor signal.

17. The method of claim 16, further comprising:
generating an updated drive signal based on the determined value of the major amplitude; and
applying the updated drive signal to the flowtube.

18. The method of claim 12, wherein the first minor signal component is related to a coriolis mode signal that is present in the sensor signal.

19. The method of claim 12, wherein the first mode of vibration comprises a mode of vibration associated with applying the drive signal to the flowtube, and the second mode of vibration comprises a mode of vibration associated with a contaminant.

20. The method of claim 12, further comprising:
determining, based on the analysis of the first received sensor signal, a first timing offset between a first zero-crossing of the first major signal component and a second zero-crossing of the first received sensor signal, the first timing offset caused at least in part by a presence of the first minor signal component.

21. The method of claim 20 further comprising determining characteristics of the second mode of vibration based on the timing offset, the characteristics comprising one or more of an amplitude, a phase, and a frequency associated with the second mode of vibration.

22. The method of claim 12 further comprising:
determining a frequency of the first received sensor signal; and
determining a density of the fluid based on the determined frequency.

23. A flowmeter transmitter comprising:
at least one processing device; and
a storage device, the storage device storing instructions for causing the at least one processing device to:
induce motion in a flowtube by applying a drive signal to the flowtube, the flowtube having at least two natural modes of vibration, the modes of vibration having different periods of oscillation;
receive a first sensor signal from a first sensor that is operable to sense a vibration of the flowtube, the first sensor signal comprising a first major signal component associated with a first one of the modes of vibration, and a first minor signal component associated with a second one of the modes of vibration;
receive a second sensor signal from a second sensor that is operable to sense a vibration of the flowtube, the second sensor signal comprising a second major signal component associated with the first mode of vibration, and a second minor signal component associated with the second mode of vibration;
analyze the first received sensor signal over a time period that is defined with respect to the period of oscillation of one of the modes of vibration of the flowtube;
analyze the second received sensor signal over a time period that is defined with respect to the period of oscillation of one of the modes of vibration of the flowtube; and determine a difference between a phase of the first sensor signal and the second sensor signal based on the analysis of the first received sensor signal and the analysis of the second received sensor signal.

24. The flowmeter transmitter of claim 23, wherein:
to analyze the first received sensor signal over a time period that is defined with respect to the period of oscillation of one of the modes of vibration, the instructions further include instructions for causing the at least one processing device to analyze the first received sensor signal over a time period that is defined with respect to the period of oscillation of the second mode of vibration, and
to analyze the second received sensor signal over a time period that is defined with respect to the period of oscillation of one of the modes of vibration, the instructions further include instructions for causing the at least one processing device to analyze the second received sensor signal over the time period that is defined with respect to the period of oscillation of the second mode of vibration.

25. The flowmeter transmitter of claim 23, wherein:
to analyze the first received sensor signal over a time period that is defined with respect to the period of oscillation of one of the modes of vibration, the instructions further include instructions for causing the at least one processing device to analyze the first received sensor signal over the time period that is defined with respect to a period of oscillation of the first mode of vibration, and
to analyze the second received sensor signal over a time period that is defined with respect to the period of oscillation of one of the modes of vibration, the instructions further include instructions for causing the at least one processing device to analyze the second received sensor signal over the time period that is defined with respect to a period of oscillation of the first mode of vibration.

26. A flowmeter transmitter comprising:
at least one processing device; and
a storage device, the storage device storing instructions for causing the at least one processing device to:
induce motion in a flowtube by applying a drive signal to the flowtube, the flowtube having at least two natural modes of vibration, which have modes of vibration having different periods of oscillation, the flowtube being configured to pass fluid by applying a drive signal to the flowtube;
receive a sensor signal from a sensor that is operable to sense a vibration of the flowtube, the sensor signal comprising a major signal component associated with a one of the modes of vibration, and a minor signal component associated with a second one of the modes of vibration;
analyze the received sensor signal over a time period that is defined with respect to the period of oscillation of one of the modes of vibration of the flowtube; and
determine a representation of a phase of the major signal component based on the analysis of the received signal.

27. The flowmeter transmitter of claim 26, wherein to analyze the received sensor signal over a time period that is defined with respect to the period of oscillation of one of the modes of vibration of the flowtube, the instructions further include instructions for causing the at least one processing device to analyze the received sensor signal over a time period that is defined with respect to the second one of the modes of vibration.

28. The flowmeter transmitter of claim 26, wherein the storage device further stores instructions to cause the at least one processing device to:

receive a second sensor signal from a second sensor that is operable to sense a vibration of the flowtube, the second sensor signal comprising a second major signal component associated with the one of the modes of vibration, and a second minor signal component associated with the second one of the modes of vibration;
analyze the second received sensor signal over a time period that is defined with respect to the period of oscillation of one of the modes of vibration;
determine a representation of a phase of the second major signal component based on analyzing the second received sensor signal; and
determine a difference between the representation of the phase of the major signal component and the representation of the phase of the second major signal component based on the analysis of the received sensor signal and the analysis of the second received sensor signal.

29. The flowmeter transmitter of claim 28, wherein the storage device further stores instructions for causing the at least one processing device to determine a mass flowrate of the fluid based on the difference between the representation of the phase of the major signal component and the representation of the phase of the second major signal component.

30. The flowmeter transmitter of claim 26, wherein the major signal component has a major amplitude, and the minor signal component has a minor amplitude, and the storage device further stores instructions to cause the at least one processing device to determine a value of the major amplitude based on the analysis of the received sensor signal.

31. The flowmeter transmitter of claim 30, wherein the storage device further stores instructions to cause the at least one processor to:
generate an updated drive signal based on the determined value of the major amplitude; and
apply the updated drive signal to the flowtube.

32. The flowmeter transmitter of claim 26, wherein the minor signal component is related to a coriolis mode signal that is present in the sensor signal.

33. The flowmeter transmitter of claim 26, wherein the one of the modes of vibration comprises a mode of vibration associated with applying the drive signal to the flowtube, and the second one of the modes of vibration comprises a mode of vibration associated with a contaminant.

34. The flowmeter transmitter of claim 26, wherein the storage device further stores instructions for causing the at least one processing device to:
determine, based on the analysis of the received sensor signal, a first timing offset between a first zero-crossing of the major signal component and a second zero-crossing of the received sensor signal, the first timing offset caused at least in part by a presence of the minor signal component.

35. The flowmeter transmitter of claim 34, wherein the storage device further stores instructions for causing the at least one processing device to determine characteristics of the second one of the modes of vibration based on the timing offset, the characteristics comprising one or more of an amplitude, a phase, and a frequency associated with the second one of the modes of vibration.

36. The flowmeter transmitter of claim 26, wherein the storage device further stores instructions for causing the at least one processing device to:
determine a frequency of the received sensor signal; and
determine a density of the fluid based on the determined frequency.

* * * * *